US012594342B2

(12) United States Patent
Achmatowicz et al.

(10) Patent No.: US 12,594,342 B2
(45) Date of Patent: Apr. 7, 2026

(54) METHOD OF CONJUGATION OF CYS-MABS

(71) Applicant: AMGEN INC., Thousand Oaks, CA (US)

(72) Inventors: Michal Achmatowicz, Simi Valley, CA (US); Dante Romanini, Sherman Oaks, CA (US); James R. Falsey, Moorpark, CA (US); Bradley J. Herberich, Newbury Park, CA (US); Oliver R. Thiel, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 100 days.

(21) Appl. No.: 16/636,325

(22) PCT Filed: Aug. 3, 2018

(86) PCT No.: PCT/US2018/045212
§ 371 (c)(1),
(2) Date: Feb. 3, 2020

(87) PCT Pub. No.: WO2019/028382
PCT Pub. Date: Feb. 7, 2019

(65) Prior Publication Data
US 2021/0346513 A1 Nov. 11, 2021

Related U.S. Application Data

(60) Provisional application No. 62/541,522, filed on Aug. 4, 2017.

(51) Int. Cl.
*A61K 47/68* (2017.01)
*C07K 14/605* (2006.01)
*C07K 16/28* (2006.01)

(52) U.S. Cl.
CPC ...... *A61K 47/6859* (2017.08); *A61K 47/6811* (2017.08); *A61K 47/6889* (2017.08); *C07K 14/605* (2013.01); *C07K 16/2869* (2013.01); *C07K 2317/40* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 4,946,778 | A | 8/1990 | Ladner et al. |
| 4,965,195 | A | 10/1990 | Namen et al. |
| 4,968,607 | A | 11/1990 | Dower et al. |
| 5,011,912 | A | 4/1991 | Hopp et al. |
| 5,260,203 | A | 11/1993 | Ladner et al. |
| 5,292,658 | A | 3/1994 | Cormier et al. |
| 5,418,155 | A | 5/1995 | Cormier et al. |
| 5,530,101 | A | 6/1996 | Queen et al. |
| 5,545,806 | A | 8/1996 | Lonberg et al. |
| 5,545,807 | A | 8/1996 | Surami et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,683,888 | A | 11/1997 | Campbell |
| 5,693,761 | A | 12/1997 | Queen et al. |
| 5,693,762 | A | 12/1997 | Queen et al. |
| 5,714,142 | A | 2/1998 | Blaney et al. |
| 5,741,668 | A | 4/1998 | Ward et al. |
| 5,770,429 | A | 6/1998 | Lonberg et al. |
| 5,777,079 | A | 7/1998 | Tsien et al. |
| 5,789,650 | A | 8/1998 | Lonberg et al. |
| 5,804,387 | A | 9/1998 | Cormack et al. |
| 5,814,318 | A | 9/1998 | Lonberg et al. |
| 5,874,299 | A | 2/1999 | Lonberg et al. |
| 5,874,304 | A | 2/1999 | Zolotukhin et al. |
| 5,876,995 | A | 3/1999 | Bryan |
| 5,877,397 | A | 3/1999 | Lonberg et al. |
| 5,925,558 | A | 7/1999 | Tsien et al. |
| 6,162,963 | A | 12/2000 | Kucherlapati et al. |
| 6,180,370 | B1 | 1/2001 | Queen et al. |
| 6,255,458 | B1 | 7/2001 | Lonberg et al. |
| 6,270,964 | B1 | 8/2001 | Michnick et al. |
| 6,300,129 | B1 | 10/2001 | Lonberg et al. |
| 6,342,225 | B1 | 1/2002 | Jones et al. |
| 6,660,843 | B1 | 12/2003 | Feige et al. |
| 6,673,986 | B1 | 1/2004 | Kucherlapati et al. |

(Continued)

FOREIGN PATENT DOCUMENTS

| | | | |
|---|---|---|---|
| EP | 367566 | A1 | 5/1990 |
| EP | 460846 | A1 | 12/1991 |

(Continued)

OTHER PUBLICATIONS

Junutula et al., Nat. Biotechnol. 26:925-932 (2008) (Year: 2008).*
"Protein Purification by Ion-Exchange Chromatography", available online at http://www.reachdevices.com/Protein/ProteinPurification.html, 10 pages (first available 2010) (Year: 2010).*
Strohl, WR, BioDrugs 29:215-239 (2015) (Year: 2015).*
PubChem, "Cysteamine", NIH: Natl. Library of Medicine, available online at https://pubchem.ncbi.nlm.nih.gov/compound/Cysteamine, 82 pages (first available 2004) (Year: 2004).*
Ausubel et al., Current Protocols in Molecular Biology, Greene Publishing Associates (1992), Table of Contents Only.
Ausubel, F. M. et al., eds., "Hybridization with Radioactive Probes, Using DNA Fragments as Probes," *Current Protocols in Molecular Biology*, John Wiley & Sons, Inc., NY, Section II, Supplements Unit 6.3, pp. 6.3.1-6.3.6 (1989).
Ausubel, F. M. et al., eds., Duby, Allan, Jacobs, Kenneth A., Celeste, Anthony, Contributors, "Hybridization With Radioactive Probes, Using Synthetic Oligonucleotides as Probes," *Current Protocols in Molecular Biology*, John Wiley and Sons, Inc., Chapter 6, Section II, Supplements 2, 13,and 9, Unit 6.4 (6.4.1-6.4.9) (1993), Copyright (2000).

(Continued)

*Primary Examiner* — Thea D' Ambrosio
(74) *Attorney, Agent, or Firm* — Carissa R. Childs

(57) ABSTRACT

The present disclosure relates to a method of capping, reducing, and oxidizing cys-mAbs in order to provide homogenous material for subsequent conjugation reactions. The present method demonstrates robust ways to manufacture conjugates of cysteine-engineered antibodies that offer high yield and consistent product quality.

24 Claims, 6 Drawing Sheets

Specification includes a Sequence Listing.

(56) References Cited

U.S. PATENT DOCUMENTS

| | | | | | |
|---|---|---|---|---|---|
| 6,713,610 | B1 | 3/2004 | Kucherlapati et al. | | |
| 6,887,470 | B1 | 5/2005 | Bridon et al. | | |
| 6,926,898 | B2 | 8/2005 | Rosen et al. | | |
| 2003/0069395 | A1 | 4/2003 | Sato et al. | | |
| 2003/0191056 | A1 | 10/2003 | Walker et al. | | |
| 2003/0195154 | A1 | 10/2003 | Walker et al. | | |
| 2005/0054051 | A1 | 3/2005 | Rosen et al. | | |
| 2012/0213705 | A1* | 8/2012 | Dimasi | A61P 37/02 | 435/69.6 |
| 2016/0130358 | A1* | 5/2016 | Bhakta | C07K 16/32 | 530/391.5 |

FOREIGN PATENT DOCUMENTS

| | | | | |
|---|---|---|---|---|
| EP | 546073 | A1 | 9/1997 | |
| EP | 546073 | B1 | 9/1997 | |
| JP | 2010526821 | A | 8/2010 | |
| WO | 88/01649 | A1 | 3/1988 | |
| WO | 90/04036 | A1 | 4/1990 | |
| WO | 91/10741 | A1 | 7/1991 | |
| WO | 92/03918 | A1 | 3/1992 | |
| WO | 92/15673 | A1 | 9/1992 | |
| WO | 92/22646 | A1 | 12/1992 | |
| WO | 93/1227 | A1 | 1/1993 | |
| WO | 94/02602 | A1 | 2/1994 | |
| WO | 95/07463 | A1 | 3/1995 | |
| WO | 96/33735 | A1 | 10/1996 | |
| WO | 98/14605 | A1 | 4/1998 | |
| WO | 98/24893 | A1 | 6/1998 | |
| WO | 98/26277 | A2 | 6/1998 | |
| WO | 99/10494 | A1 | 3/1999 | |
| WO | 99/49019 | A2 | 9/1999 | |
| WO | 2005084390 | A2 | 9/2005 | |
| WO | 2006/134173 | A2 | 12/2006 | |
| WO | 2006/134174 | A2 | 12/2006 | |
| WO | 2008141044 | A2 | 11/2008 | |
| WO | 2009012256 | A1 | 1/2009 | |
| WO | 2012/010516 | A1 | 1/2012 | |
| WO | 2015086853 | A1 | 6/2015 | |
| WO | 2015123265 | A1 | 8/2015 | |
| WO | 2016067013 | A1 | 5/2016 | |
| WO | 2016/103146 | A1 | 6/2016 | |
| WO | 2017/025897 | A2 | 2/2017 | |
| WO | WO-2017055582 | A1 * | 4/2017 | A61K 38/27 |
| WO | WO-2017112824 | A2 * | 6/2017 | A61P 3/10 |
| WO | 2017137628 | A1 | 8/2017 | |
| WO | 2018/039647 | A1 | 3/2018 | |
| WO | WO-2018136440 | A1 * | 7/2018 | A61K 38/22 |
| WO | 2019028382 | A1 | 2/2019 | |

OTHER PUBLICATIONS

Ausubel, F. M. et al., eds., Strauss, William M., Contributor, "Hybridization With Radioactive Probes, Using DNA Fragments as Probes," *Current Protocols in Molecular Biology*, John Wiley and Sons, Inc., Chapter 6, Section II, Supplements 24, 13, and 2, Unit 6.3 (6.3.1-6.3.6) (1993), Copyright (2000).

Behrens, C. R. et al., "Methods for site-specific drug conjugation to antibodies," *MABS*, 6(1):46-53 (2014).

Bianchi, A. A. and McGrew, J. T., "High-Level Expression of Full-Length Antibodies Using Trans-Complementing Expression Vectors," *Biotech Biotechnol. Bioeng.*, 84:439-444 (2003).

Bong, D. T. et al., Chemoselective Pd(0)-catelyzed peptide coupling in water, *Organic Letters*, 3(16):2509-2511 (2001).

Bootcov, M. R. et al., "MIC-1, a novel macrophage inhibitory cytokind, is a divergent member of the TGF-β superfamily," *Proc. Natl. Acad. Sci. USA*, 94:11514-11519 (1997).

Bruggermann, M. et al., "Design Mice: The Production of Human Antibody Repertoires in Transgenic Animals," *Year in Immunol.*, 7:33-40 (1993).

Carrillo, H. et al., "The Multiple Sequence Alignment Problem in Biology," *SIAM J. Applied Math*, Society for Industrial and Applied Mathematics, 48(5):1073-1082 (1988).

Chalfie, M. et al., "Green Fluorescent Protein as a Marker for Gene Expression," *Science*, 263:802-805 (1994).

Chen, J. et al., "Immunoglobulin gene rearrangement in B cell deficient mice generated by targeted deletion of the $J_H$ locus," *International Immunology*, 5(6):647-656 (1993).

Cheung, R. C. et al., "Epitope-Specific Antibody Response to the Surface Antigen of Duck Hepatitis B Virus in Infected Ducks," *Virology*, 176:546-552 (1990).

Chothia, C. and Lesk, A. M., "Canonical Structures for the Hypervariable Regions of Immunoglobulins," *J. Mol. Biol.*, 196:901-917 (1987).

Chothia, C. et al., "Conformations of immunoglobulin hypervariable regions," *Nature*, 342:877-883 (1989).

Cosman, D. et al., "Cloning, sequence and expression of human interleukin-2 receptor," *Nature*, 312:768-771 (1984).

Creighton, T. E., Ed., *Proteins: Structures and Molecular Principles*, $2^{nd}$ ed., W. H. Freeman and Company, New York (1984) (Table of Contents Only).

Dayhoff, M. O. et al., *Atlas of Protein Sequence and Structure*, Chapter 22, a Model of Evolutionary Change in Proteins, 5(3):345-352 (1979).

DeVasher et al., Aqueous-phase, palladium-catalyzed cross-coupling of aryl bromides under mild conditions, using water-soluble, sterically demanding alkylphosphines, J. Org. Chem. 69:7919-27 (2004).

Devereux, J. et al., "A comprehensive set of sequence analysis programs for the VAX," *Nucl. Acid Res.*, Laboratory of Genetics, University of Wisconsin, Madison, WI, 12(1):387-395 (1984).

Dibowski, H. et al., Bioconjugation of peptides by palladium-catalyzed C—C cross-coupling in water, *Angew. Chem. Int. Ed.*, 37(4):476-478 (1998).

Fairlie, W. D., "Expression of a TGF-β superfamily protein, macrophage inhibitory cytokine-1, in the yeast Pichia pastoris," *Gene*, 254:67-76 (2000).

Fishwild, D. M. et al., "High-avidity human IgGκ monoclonal antibodies from a novel strain of minilocus transgenic mice," *Nature Biotechnology*, 14:845-851 (1996).

Genbank Accession No. U55762, "Cloning vector pEGFP-N1, complete sequence, enhanced green fluorescent protein (egfp) and neomycin phosphotransferase genes, complete cds," Clontech Labs, Inc., Kitts, P. A., (2003).

Goeddel, D. V., Contributor., Methods in Enzymology, Gene Expression Technology, vol. 185, New York: Academic Press, Inc. (1990) (Table of Contents Only).

Gribskov, M. and Devereux, J., eds., Sequence Analysis Primer, New York: M. Stockton Press, (1991) (Table of Contents Only).

Griffin, A. M. and Griffin, H. G., eds., Computer Analysis of Sequence Data, Part I, Humana Press, Totowa, New Jersey (1994) (Table of Contents Only).

Harding, F. A. and Lonberg, N., "Class Switching in Human Immunoglobulin Transgenic Mice," *Ann. NY Acad. Sci.*, 765:536-546 (1995).

Harlow, E. and Lane, D., Antibodies: A Laboratory Manual, Cold Spring Harbor Laboratory Press, Cold Spring Harbor, NY (1988) (Table of Contents Only).

Heim, R. et al., "Engineering green fluorescent protein for improved brightness, longer wavelengths and fluorescence resonance energy transfer," *Current Biology*, 6:178-182 (1996).

Henikoff, S. et al., "Amino acid substitution matrices from protein blocks," *Proc. Natl. Acad. Sci. USA*, 89:10915-10919 (1992).

Hoogenboom et al., "By-passing Immunisation Human Antibodies from Synthetic Repertoires of Germline $V_H$ Gene Segments Rearranged in Vitro," *J. Mol. Biol.*, 227:381-388 (1991).

Hopp, T. P. et al., "A Short Polypeptide Marker Sequence Useful for Recombinant Protein Identification and Purification," *Bio/Technology*, 6:1204-1210 (1988).

Ichiki, T. et al., "Regulation of the expression of human C epsilon germline transcript. Identification of a novel IL-4 responsive element," *The Journal of Immunology*, 150:5408-5417 (1993).

Jagath R Junutula et al: "Site-specific conjugation of a cytotoxic drug to an antibody improves the therapeutic index," *Nature Biotechnology*, 26(8):925-932 (2008).

(56) References Cited

OTHER PUBLICATIONS

Jakobovits, A. et al., "Analysis of homozygous mutant chimeric mice: deletion of the immunoglobulin heavy-chain joining region blocks B-cell development and antibody production," *Proc. Natl. Acad. Sci. USA*, 90:2551-2555 (1993).
Jakobovits, A. et al., "Germ-line transmission and expression of a human-derived yeast artificial chromosome," *Nature*, 362:255-258 (1993).
Jones, P. T. et al., "Replacing the complementarity-determining regions in a human antibody with those from a mouse," *Nature*, 321:522-525 (1986).
Kabat, E. A. et al., Sequences of Proteins of Immunological Interest, 5th ed., U.S. Dept. of Health and Human Services, PHS, NIH, Bethesda, MD (1987 and 1991) (Table of Contents Only).
Kabat, E. A. et al., Sequences of Proteins of Immunological Interest, 5th ed., U.S. Dept. of Health and Human Services, PHS, NIH, NIH Publication No. 91-3242, Bethesda, MD (1991) (Table of Contents Only).
Kennett, R. H. et al., eds., Monoclonal Antibodies, Hybridomas: A New Dimension in Biological Analyses, Plenum Press, New York (1980) (Table of Contents Only).
Kirkland, T. N. et al., "Analysis of the Fine Specificity and Cross-Reactivity of Monoclonal Anti-Lipid A Antibodies," *The Journal of Immunology*, 137(11):3614-3619 (1986).
Kostelny, S. A. et al., "Formation of a Bispecific Antibody by the Use of Leucine Zippers," The Journal of Immunology, 148(5):1547-1553 (1992).
Lesk, A. M., ed., Computational Molecular Biology, Sources and Methods for Sequence Analysis, New York: Oxford University Press, Oxford New York Tokyo (1988) (Table of Contents Only).
Lonberg, N. and Huszar, D., "Human Antibodies from Transgenic Mice," *Intern. Rev. Immunol.*, 13:65-93 (1995).
Lonberg, N. et al., "Antigen-specific human antibodies from mice comprising four distinct genetic modifications," *Nature*, 368:856-859 (1994).
Lonberg, N. et al., *The Pharmacology of Monoclonal Antibodies*—Chapter 3: "Transgenic Approaches to Human Monoclonal Antibodies," *Handbook of Exp. Pharmacology*, 113:49-101 (1994).
Lyon Robert P et al: "Chapter 6: Conjugation of Anticancer Drugs Endogenous Monoclonal Antibody Cysteine Residues," Methods in Enzymo, Academic Press, US, 502(1):123-138 (2012).
Maniatis, T. et al., "Regulation of Inducible and Tissue-Specific Gene Expression," Science, 236:1237-1244 (1987).
Marks, J. D. et al., "By-passing Immunization: Human Antibodies and V-gene Libraries Displayed on Phage," J. Mol. Biol., 222:581-597 (1991).
Mendez, M. J. et al., "Functional transplant of megabase human immunoglobulin loci recapitulates human antibody response in mice," Nature Genetics, 15:146-156 (1997).
Moldenhauer, G. et al., "Identity of HML-1 Antigen on Intestinal Intraepithelial T Cells and of B-ly7 Antigen on Hairy Cell Leukaemia," Scand. J. Immunol., 32:77-82 (1990).
Morel, G. A. et al., "Monoclonal Antibodies to Bovine Serum Albumin: Affinity and Specificity Determinations," Molecular Immunology, 25(1):7-15 (1988).
Morrison, S. L. et al., "Chimeric human antibody molecules: Mouse antigen-binding domains with human constant region domains," Proc. Natl. Acad. Sci. USA, 81:6851-6855 (1984).
Needleman, S. B. et al., Algorithm, "A General Method Applicable to the Search for Similarities in the Amino Acid Sequence of Two Proteins," J. Mol. Biol., 48:443-453 (1970).
Nolan, G. P. et al., "Flourescence-activated cell analysis and sorting of viable mammalian cells based on beta-D-galactosidase activity after transduction of *Escherichia coli* lacZ," Proc. Natl. Acad. Sci. USA, 85:2603-2607 (1988).
Paul, W. E. et al., *Fundamental Immunology*, 2nd ed., Chapter 7: Evolution of the Immune System, pp. 139-165, Raven Press, New York (1989).
Prescher, J. A., and Bertozzi, C. R., Chemistry in living systems, Nature Chemical Biology, 1(1):13-21 (2005).
Riechmann, L.et al., "Reshaping human antibodies for therapy," Nature, 332(24):323-327 (1988).
Sambrook, J. et al., *Molecular Cloning: A Laboratory Manual*, 2nd ed., Cold Spring Harbor Laboratory Press (1989) (Table of Contents Only).
Sambrook, J. et al., *Molecular Cloning: A Laboratory Manual*, 3rd ed., Cold Spring Harbor Laboratory Press, Cold Spring Harbor, NY (2001) (Table of Contents Only).
Shaugnessy et al., "Efficient One-Step Suzuki Arylation of Unprotected Halonucleosides, Using Water-Soluble Palladium Catalysts," *J.Org. Chem*, 68, 6767-6774 (2003).
Smith, D. W., ed., *Biocomputing Informatics and Genome Projects*, New York: Academic Press (1994) (Table of Contents Only).
Songsivilai, S. and Lachmann, P. J., "Bispecific antibody: a tool for diagnosis and treatment of disease," *Clin. Exp. Immunol.*, 79:315-321 (1990).
Stahli, C. et al., "Distinction of Epitopes by Monoclonal Antibodies," *Methods in Enzymology*, 92:242-253 (1983).
Stauber, R. H., "Developments and Applications of Enhanced Green Fluorescent Protein Mutants," *BioTechniques*, 24(3):462-471 (1998).
Taylor, L. D. et al., "A Transgenic mouse that expresses a diversity of human sequence heavy and light chain immunoglobulins," *Nucleic Acids Research*, 20(23):6287-6295 (1992).
Taylor, L. D. et al., "Human immunoglobulin transgenes undergo rearrangement, somatic mutation and class switching in mice that lack endogenous IgM," *International Immunology*, 6(4):579-591 (1994).
Tuaillon, N. et al., "Biased utilization of DHQ52 and JH4 gene segments in a human Ig transgenic minilocus is independent of antigenic selection," *The Journal of Immunology*, 152:2912-2920 (1994).
Van Heeke, G. & Schuster, S. M., "Expression of Human Asparagine Synthetase in *Escherichia coli," The Journal of Biological Chemistry*, 264(10):5503-5509 (1989).
Verhoeyen, M. et al., "Reshaping Human Antibodies: Grafting an Antilysozyme Activity," Science, 239:1534-1536 (1988).
Von Heinje, G., Sequence Analysis in Molecular Biology, Academic Press, Inc., New York (1987) (Table of Contents Only).
Voss, S. D. et al., "The role of enhancers in the regulation of cell-type-specific transcriptional control," TIBS, 11:287 (1986).
Chen et al., "Charge-based analysis of antibodies with engineered cysteines: from multiple peaks to a single main peak," mAbs, vol. 1(6), pp. 563-571 (2009).
European Patent Office, Notice of Opposition Against EP 3661562, Jun. 30, 2025, 25 pages.
Reply of the patent proprietor to the notice of opposition issued in Patent No. EP 3661562, filed Nov. 14, 2025.
Supplemental reply and affidavit of the patent proprietor to the notice of opposition issued in Patent No. EP 3661562, filed Dec. 23, 2025.
U.S. Appl. No. 62/380,216, filed Aug. 26, 2016 including prosecution history.

* cited by examiner

SEQUENCE LISTING

```
<160> NUMBER OF SEQ ID NOS: 165

<210> SEQ ID NO 1
<211> LENGTH: 324
<212> TYPE: DNA
<213> ORGANISM: Artificial Sequence
<220> FEATURE:
<223> OTHER INFORMATION: ANTIBODY OR ANTIBODY PORTION

<400> SEQUENCE: 1

gacatccagc tgacccagtc tccatcctcc ctgtctgcat ctgtaggaga cagagtcact     60

atcacttgcc gggcaagtca gaccattagc aggtttttaa attggtatca gcagaaacct    120

gggaaagccc ctgagctcct gatctatgtt gcatccagtt tgcaaagtgg ggtcccatca    180

agattcagtg gcagtggttc tgggacagat ttcactctca ccatcagcag tctgcaacct    240

gaagattttg caacttacta ctgtcaacag agttacagta ccctgatcag ttttggccag    300

gggaccaagc tggagatcac acga                                           324


<210> SEQ ID NO 2
<211> LENGTH: 363
<212> TYPE: DNA
<213> ORGANISM: Artificial Sequence
<220> FEATURE:
<223> OTHER INFORMATION: ANTIBODY OR ANTIBODY PORTION

<400> SEQUENCE: 2

caggtgcagt tggtggagtc tgggggaggc gtggtccagc ctgggaggtc cctgagactc     60

tcctgtacag cgtctggatt caccttcagt agctatggca tacactgggt ccgccaggct    120

ccaggcaagg ggctggagtg ggtggcagtt atatggtatg atggaagtaa taagttccat    180

gcagactccg tgaagggccg attcaccatc tccagagaca attccaagaa cacgctgtat    240

ctgcaaatga acagcctgag agccgaggac tcggctatgt acttctgtgc gagaggaaaa    300

gtggctggta tgcctgaagc ttttgaaatc tggggccaag ggacaaaggt caccgtctct    360

tca                                                                  363


<210> SEQ ID NO 3
<211> LENGTH: 108
<212> TYPE: PRT
```

<213> ORGANISM: Artificial Sequence
<220> FEATURE:
<223> OTHER INFORMATION: ANTIBODY OR ANTIBODY PORTION

<400> SEQUENCE: 3

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Ile Ser Arg Phe
            20                  25                  30

Leu Asn Trp Tyr Gln Gln Lys Pro Gly Lys Ala Pro Glu Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Ile
                85                  90                  95

Ser Phe Gly Gln Gly Thr Lys Leu Glu Ile Thr Arg
            100                 105
```

<210> SEQ ID NO 4
<211> LENGTH: 121
<212> TYPE: PRT
<213> ORGANISM: Artificial Sequence
<220> FEATURE:
<223> OTHER INFORMATION: ANTIBODY OR ANTIBODY PORTION

<400> SEQUENCE: 4

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Phe His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Met Tyr Phe Cys
                85                  90                  95

Ala Arg Gly Lys Val Ala Gly Met Pro Glu Ala Phe Glu Ile Trp Gly
            100                 105                 110

Gln Gly Thr Lys Val Thr Val Ser Ser
        115                 120
```

<210> SEQ ID NO 5
<211> LENGTH: 642
<212> TYPE: DNA
<213> ORGANISM: Artificial Sequence
<220> FEATURE:
<223> OTHER INFORMATION: ANTIBODY OR ANTIBODY PORTION

<400> SEQUENCE: 5

```
gacatccagc tgacccagtc tccatcctcc ctgtctgcat ctgtaggaga cagagtcact      60

atcacttgcc gggcaagtca gaccattagc aggtttttaa attggtatca gcagaaacct     120

gggaaagccc ctgagctcct gatctatgtt gcatccagtt tgcaaagtgg ggtcccatca     180

agattcagtg gcagtggttc tgggacagat ttcactctca ccatcagcag tctgcaacct     240
```

-continued

```
gaagattttg caacttacta ctgtcaacag agttacagta ccctgatcag ttttggccag    300

gggaccaagc tggagatcac acgaacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 6
<211> LENGTH: 1353
<212> TYPE: DNA
<213> ORGANISM: Artificial Sequence
<220> FEATURE:
<223> OTHER INFORMATION: ANTIBODY OR ANTIBODY PORTION

<400> SEQUENCE: 6

```
caggtgcagt tggtggagtc tgggggaggc gtggtccagc ctgggaggtc cctgagactc     60

tcctgtacag cgtctggatt caccttcagt agctatggca tacactgggt ccgccaggct    120

ccaggcaagg ggctggagtg ggtggcagtt atatggtatg atggaagtaa taagttccat    180

gcagactccg tgaagggccg attcaccatc tccagagaca attccaagaa cacgctgtat    240

ctgcaaatga acagcctgag agccgaggac tcggctatgt acttctgtgc gagaggaaaa    300

gtggctggta tgcctgaagc ttttgaaatc tggggccaag ggacaaaggt caccgtctct    360

tcagcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgtgtga ggagcagtac    900

ggcagcacgt accgttgtgt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggag   1080

gagatgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tatagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaa                                1353
```

<210> SEQ ID NO 7
<211> LENGTH: 214
<212> TYPE: PRT
<213> ORGANISM: Artificial Sequence
<220> FEATURE:
<223> OTHER INFORMATION: ANTIBODY OR ANTIBODY PORTION

<400> SEQUENCE: 7

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Thr Ile Ser Arg Phe
            20                  25                  30

Leu Asn Trp Tyr Gln Gln Lys Pro Gly Lys Ala Pro Glu Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Ile
                85                  90                  95

Ser Phe Gly Gln Gly Thr Lys Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 8
<211> LENGTH: 451
<212> TYPE: PRT
<213> ORGANISM: Artificial Sequence
<220> FEATURE:
<223> OTHER INFORMATION: ANTIBODY OR ANTIBODY PORTION

<400> SEQUENCE: 8

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Phe His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Met Tyr Phe Cys
                85                  90                  95

Ala Arg Gly Lys Val Ala Gly Met Pro Glu Ala Phe Glu Ile Trp Gly
            100                 105                 110

Gln Gly Thr Lys Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

-continued

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Cys Glu Glu Gln Tyr Gly Ser Thr Tyr
    290                 295                 300

Arg Cys Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 9
<211> LENGTH: 33
<212> TYPE: DNA
<213> ORGANISM: Artificial Sequence
<220> FEATURE:
<223> OTHER INFORMATION: ANTIBODY OR ANTIBODY PORTION

<400> SEQUENCE: 9
cgggcaagtc agaccattag caggttttta aat 33

<210> SEQ ID NO 10
<211> LENGTH: 21
<212> TYPE: DNA
<213> ORGANISM: Artificial Sequence
<220> FEATURE:

<223> OTHER INFORMATION: ANTIBODY OR ANTIBODY PORTION

<400> SEQUENCE: 10
gttgcatcca gtttgcaaag t 21

<210> SEQ ID NO 11
<211> LENGTH: 27
<212> TYPE: DNA
<213> ORGANISM: Artificial Sequence
<220> FEATURE:
<223> OTHER INFORMATION: ANTIBODY OR ANTIBODY PORTION

<400> SEQUENCE: 11
caacagagtt acagtaccct gatcagt 27

<210> SEQ ID NO 12
<211> LENGTH: 11
<212> TYPE: PRT
<213> ORGANISM: Artificial Sequence
<220> FEATURE:
<223> OTHER INFORMATION: ANTIBODY OR ANTIBODY PORTION

<400> SEQUENCE: 12

Arg Ala Ser Gln Thr Ile Ser Arg Phe Leu Asn
1 5 10

<210> SEQ ID NO 13
<211> LENGTH: 7
<212> TYPE: PRT
<213> ORGANISM: Artificial Sequence
<220> FEATURE:
<223> OTHER INFORMATION: ANTIBODY OR ANTIBODY PORTION

<400> SEQUENCE: 13

Val Ala Ser Ser Leu Gln Ser
1 5

<210> SEQ ID NO 14
<211> LENGTH: 9
<212> TYPE: PRT
<213> ORGANISM: Artificial Sequence
<220> FEATURE:
<223> OTHER INFORMATION: ANTIBODY OR ANTIBODY PORTION

<400> SEQUENCE: 14

Gln Gln Ser Tyr Ser Thr Leu Ile Ser
1 5

<210> SEQ ID NO 15
<211> LENGTH: 15
<212> TYPE: DNA
<213> ORGANISM: Artificial Sequence
<220> FEATURE:
<223> OTHER INFORMATION: ANTIBODY OR ANTIBODY PORTION

<400> SEQUENCE: 15
agctatggca tacac 15

<210> SEQ ID NO 16
<211> LENGTH: 51
<212> TYPE: DNA
<213> ORGANISM: Artificial Sequence
<220> FEATURE:
<223> OTHER INFORMATION: ANTIBODY OR ANTIBODY PORTION

<400> SEQUENCE: 16
gttatatggt atgatggaag taataagttc catgcagact ccgtgaaggg c 51

<210> SEQ ID NO 17
<211> LENGTH: 36
<212> TYPE: DNA
<213> ORGANISM: Artificial Sequence
<220> FEATURE:
<223> OTHER INFORMATION: ANTIBODY OR ANTIBODY PORTION

<400> SEQUENCE: 17
ggaaaagtgg ctggtatgcc tgaagctttt gaaatc 36

<210> SEQ ID NO 18
<211> LENGTH: 5
<212> TYPE: PRT
<213> ORGANISM: Artificial Sequence
<220> FEATURE:
<223> OTHER INFORMATION: ANTIBODY OR ANTIBODY PORTION

<400> SEQUENCE: 18

Ser Tyr Gly Ile His
1 5

<210> SEQ ID NO 19
<211> LENGTH: 17
<212> TYPE: PRT
<213> ORGANISM: Artificial Sequence
<220> FEATURE:
<223> OTHER INFORMATION: ANTIBODY OR ANTIBODY PORTION

<400> SEQUENCE: 19

Val Ile Trp Tyr Asp Gly Ser Asn Lys Phe His Ala Asp Ser Val Lys
1 5 10 15

Gly

<210> SEQ ID NO 20
<211> LENGTH: 12
<212> TYPE: PRT
<213> ORGANISM: Artificial Sequence
<220> FEATURE:
<223> OTHER INFORMATION: ANTIBODY OR ANTIBODY PORTION

<400> SEQUENCE: 20

Gly Lys Val Ala Gly Met Pro Glu Ala Phe Glu Ile
1 5 10

<210> SEQ ID NO 21
<211> LENGTH: 22
<212> TYPE: PRT
<213> ORGANISM: Artificial Sequence
<220> FEATURE:
<223> OTHER INFORMATION: LEADER SEQUENCE

<400> SEQUENCE: 21

Met Asp Met Arg Val Pro Ala Gln Leu Leu Gly Leu Leu Leu Leu Trp
1 5 10 15

Leu Arg Gly Ala Arg Cys
20

<210> SEQ ID NO 22
<211> LENGTH: 66
<212> TYPE: DNA
<213> ORGANISM: Artificial Sequence
<220> FEATURE:
<223> OTHER INFORMATION: LEADER SEQUENCE

<400> SEQUENCE: 22
atggacatga gagtgcctgc acagctgctg ggcctgctgc tgctgtggct gagaggcgcc 60
agatgc 66

<210> SEQ ID NO 23
<211> LENGTH: 19
<212> TYPE: PRT
<213> ORGANISM: Artificial Sequence
<220> FEATURE:
<223> OTHER INFORMATION: LEADER SEQUENCE

<400> SEQUENCE: 23

Met Ala Trp Ala Leu Leu Leu Leu Thr Leu Leu Thr Gln Gly Thr Gly
1 5 10 15

Ser Trp Ala

<210> SEQ ID NO 24
<211> LENGTH: 57
<212> TYPE: DNA
<213> ORGANISM: Artificial Sequence
<220> FEATURE:
<223> OTHER INFORMATION: LEADER SEQUENCE

<400> SEQUENCE: 24
atggcctggg ctctgctgct cctcaccctc ctcactcagg gcacagggtc ctgggcc 57

<210> SEQ ID NO 25
<211> LENGTH: 6
<212> TYPE: PRT
<213> ORGANISM: Artificial Sequence
<220> FEATURE:
<223> OTHER INFORMATION: LINKER SEQUENCE
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 25

Xaa Xaa Asn Xaa Xaa Gly
1 5

<210> SEQ ID NO 26
<211> LENGTH: 8
<212> TYPE: PRT
<213> ORGANISM: Artificial Sequence
<220> FEATURE:
<223> OTHER INFORMATION: LINKER SEQUENCE

<400> SEQUENCE: 26

Gly Gly Gly Gly Gly Gly Gly Gly
1 5

<210> SEQ ID NO 27
<211> LENGTH: 5
<212> TYPE: PRT
<213> ORGANISM: Artificial Sequence
<220> FEATURE:
<223> OTHER INFORMATION: LINKER SEQUENCE

<400> SEQUENCE: 27

Gly Gly Gly Gly Gly
1 5

-continued

<210> SEQ ID NO 28
<211> LENGTH: 7
<212> TYPE: PRT
<213> ORGANISM: Artificial Sequence
<220> FEATURE:
<223> OTHER INFORMATION: LINKER SEQUENCE

<400> SEQUENCE: 28

Gly Gly Gly Gly Gly Gly Gly
1 5

<210> SEQ ID NO 29
<211> LENGTH: 15
<212> TYPE: PRT
<213> ORGANISM: Artificial Sequence
<220> FEATURE:
<223> OTHER INFORMATION: LINKER SEQUENCE

<400> SEQUENCE: 29

Gly Gly Gly Gly Ser Gly Gly Gly Gly Ser Gly Gly Gly Gly Ser
1 5 10 15

<210> SEQ ID NO 30
<211> LENGTH: 6
<212> TYPE: PRT
<213> ORGANISM: Artificial Sequence
<220> FEATURE:
<223> OTHER INFORMATION: LINKER SEQUENCE

<400> SEQUENCE: 30

Gly Gly Gly Gly Gly Lys
1 5

<210> SEQ ID NO 31
<211> LENGTH: 7
<212> TYPE: PRT
<213> ORGANISM: Artificial Sequence
<220> FEATURE:
<223> OTHER INFORMATION: LINKER SEQUENCE

<400> SEQUENCE: 31

Gly Gly Gly Gly Gly Lys Arg
1 5

<210> SEQ ID NO 32
<211> LENGTH: 8
<212> TYPE: PRT
<213> ORGANISM: Artificial Sequence
<220> FEATURE:
<223> OTHER INFORMATION: LINKER SEQUENCE

<400> SEQUENCE: 32

Gly Gly Gly Lys Gly Gly Gly Gly
1 5

<210> SEQ ID NO 33
<211> LENGTH: 8
<212> TYPE: PRT
<213> ORGANISM: Artificial Sequence
<220> FEATURE:
<223> OTHER INFORMATION: LINKER SEQUENCE

<400> SEQUENCE: 33

Gly Gly Gly Asn Gly Ser Gly Gly
1 5

<210> SEQ ID NO 34
<211> LENGTH: 8
<212> TYPE: PRT
<213> ORGANISM: Artificial Sequence
<220> FEATURE:
<223> OTHER INFORMATION: LINKER SEQUENCE

<400> SEQUENCE: 34

Gly Gly Gly Cys Gly Gly Gly Gly
1               5

<210> SEQ ID NO 35
<211> LENGTH: 5
<212> TYPE: PRT
<213> ORGANISM: Artificial Sequence
<220> FEATURE:
<223> OTHER INFORMATION: LINKER SEQUENCE

<400> SEQUENCE: 35

Gly Pro Asn Gly Gly
1               5

<210> SEQ ID NO 36
<211> LENGTH: 8
<212> TYPE: PRT
<213> ORGANISM: Artificial Sequence
<220> FEATURE:
<223> OTHER INFORMATION: LINKER SEQUENCE

<400> SEQUENCE: 36

Gly Gly Gly Lys Gly Gly Gly Gly
1               5

<210> SEQ ID NO 37
<211> LENGTH: 5
<212> TYPE: PRT
<213> ORGANISM: Artificial Sequence
<220> FEATURE:
<223> OTHER INFORMATION: LINKER SEQUENCE

<400> SEQUENCE: 37

Gly Gly Gly Gly Ser
1               5

<210> SEQ ID NO 38
<211> LENGTH: 10
<212> TYPE: PRT
<213> ORGANISM: Artificial Sequence
<220> FEATURE:
<223> OTHER INFORMATION: LINKER SEQUENCE

<400> SEQUENCE: 38

Gly Gly Gly Gly Ser Gly Gly Gly Gly Ser
1               5                   10

<210> SEQ ID NO 39
<211> LENGTH: 20
<212> TYPE: PRT
<213> ORGANISM: Artificial Sequence
<220> FEATURE:
<223> OTHER INFORMATION: LINKER SEQUENCE

<400> SEQUENCE: 39

Gly Gly Gly Gly Ser Gly Gly Gly Gly Ser Gly Gly Gly Gly Ser Gly
1               5                   10                  15

Gly Gly Gly Ser

```
            20


<210> SEQ ID NO 40
<211> LENGTH: 25
<212> TYPE: PRT
<213> ORGANISM: Artificial Sequence
<220> FEATURE:
<223> OTHER INFORMATION: LINKER SEQUENCE

<400> SEQUENCE: 40

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 41
<211> LENGTH: 6
<212> TYPE: PRT
<213> ORGANISM: Artificial Sequence
<220> FEATURE:
<223> OTHER INFORMATION: LINKER SEQUENCE

<400> SEQUENCE: 41

Gly Gly Glu Gly Gly Gly
1               5


<210> SEQ ID NO 42
<211> LENGTH: 8
<212> TYPE: PRT
<213> ORGANISM: Artificial Sequence
<220> FEATURE:
<223> OTHER INFORMATION: LINKER SEQUENCE

<400> SEQUENCE: 42

Gly Gly Glu Glu Glu Gly Gly Gly
1               5


<210> SEQ ID NO 43
<211> LENGTH: 5
<212> TYPE: PRT
<213> ORGANISM: Artificial Sequence
<220> FEATURE:
<223> OTHER INFORMATION: LINKER SEQUENCE

<400> SEQUENCE: 43

Gly Glu Glu Glu Gly
1               5


<210> SEQ ID NO 44
<211> LENGTH: 4
<212> TYPE: PRT
<213> ORGANISM: Artificial Sequence
<220> FEATURE:
<223> OTHER INFORMATION: LINKER SEQUENCE

<400> SEQUENCE: 44

Gly Glu Glu Glu
1


<210> SEQ ID NO 45
<211> LENGTH: 6
<212> TYPE: PRT
<213> ORGANISM: Artificial Sequence
<220> FEATURE:
<223> OTHER INFORMATION: LINKER SEQUENCE

<400> SEQUENCE: 45
```

```
Gly Gly Asp Gly Gly Gly
1               5


<210> SEQ ID NO 46
<211> LENGTH: 7
<212> TYPE: PRT
<213> ORGANISM: Artificial Sequence
<220> FEATURE:
<223> OTHER INFORMATION: LINKER SEQUENCE

<400> SEQUENCE: 46

Gly Gly Asp Asp Asp Gly Gly
1               5


<210> SEQ ID NO 47
<211> LENGTH: 5
<212> TYPE: PRT
<213> ORGANISM: Artificial Sequence
<220> FEATURE:
<223> OTHER INFORMATION: LINKER SEQUENCE

<400> SEQUENCE: 47

Gly Asp Asp Asp Gly
1               5


<210> SEQ ID NO 48
<211> LENGTH: 4
<212> TYPE: PRT
<213> ORGANISM: Artificial Sequence
<220> FEATURE:
<223> OTHER INFORMATION: LINKER SEQUENCE

<400> SEQUENCE: 48

Gly Asp Asp Asp
1


<210> SEQ ID NO 49
<211> LENGTH: 21
<212> TYPE: PRT
<213> ORGANISM: Artificial Sequence
<220> FEATURE:
<223> OTHER INFORMATION: LINKER SEQUENCE

<400> SEQUENCE: 49

Gly Gly Gly Gly Ser Asp Asp Ser Asp Glu Gly Ser Asp Gly Glu Asp
1               5                   10                  15

Gly Gly Gly Gly Ser
            20


<210> SEQ ID NO 50
<211> LENGTH: 5
<212> TYPE: PRT
<213> ORGANISM: Artificial Sequence
<220> FEATURE:
<223> OTHER INFORMATION: LINKER SEQUENCE

<400> SEQUENCE: 50

Trp Glu Trp Glu Trp
1               5


<210> SEQ ID NO 51
<211> LENGTH: 5
<212> TYPE: PRT
<213> ORGANISM: Artificial Sequence
<220> FEATURE:
<223> OTHER INFORMATION: LINKER SEQUENCE
```

<400> SEQUENCE: 51

Phe Glu Phe Glu Phe
1 5

<210> SEQ ID NO 52
<211> LENGTH: 6
<212> TYPE: PRT
<213> ORGANISM: Artificial Sequence
<220> FEATURE:
<223> OTHER INFORMATION: LINKER SEQUENCE

<400> SEQUENCE: 52

Glu Glu Glu Trp Trp Trp
1 5

<210> SEQ ID NO 53
<211> LENGTH: 6
<212> TYPE: PRT
<213> ORGANISM: Artificial Sequence
<220> FEATURE:
<223> OTHER INFORMATION: LINKER SEQUENCE

<400> SEQUENCE: 53

Glu Glu Glu Phe Phe Phe
1 5

<210> SEQ ID NO 54
<211> LENGTH: 7
<212> TYPE: PRT
<213> ORGANISM: Artificial Sequence
<220> FEATURE:
<223> OTHER INFORMATION: LINKER SEQUENCE

<400> SEQUENCE: 54

Trp Trp Glu Glu Glu Trp Trp
1 5

<210> SEQ ID NO 55
<211> LENGTH: 7
<212> TYPE: PRT
<213> ORGANISM: Artificial Sequence
<220> FEATURE:
<223> OTHER INFORMATION: LINKER SEQUENCE

<400> SEQUENCE: 55

Phe Phe Glu Glu Glu Phe Phe
1 5

<210> SEQ ID NO 56
<211> LENGTH: 6
<212> TYPE: PRT
<213> ORGANISM: Artificial Sequence
<220> FEATURE:
<223> OTHER INFORMATION: LINKER SEQUENCE
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 56

Xaa Xaa Tyr Xaa Xaa Gly
1 5

<210> SEQ ID NO 57
<211> LENGTH: 6
<212> TYPE: PRT
<213> ORGANISM: Artificial Sequence
<220> FEATURE:
<223> OTHER INFORMATION: LINKER SEQUENCE
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 57

Xaa Xaa Ser Xaa Xaa Gly
1 5

<210> SEQ ID NO 58
<211> LENGTH: 6
<212> TYPE: PRT
<213> ORGANISM: Artificial Sequence
<220> FEATURE:
<223> OTHER INFORMATION: LINKER SEQUENCE
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 58

Xaa Xaa Thr Xaa Xaa Gly
1 5

<210> SEQ ID NO 59
<211> LENGTH: 22
<212> TYPE: PRT
<213> ORGANISM: Artificial Sequence
<220> FEATURE:
<223> OTHER INFORMATION: LINKER SEQUENCE

<400> SEQUENCE: 59

Gly Ser Gly Ser Ala Thr Gly Gly Ser Gly Ser Thr Ala Ser Ser Gly
1 5 10 15

Ser Gly Ser Ala Thr His
20

<210> SEQ ID NO 60
<211> LENGTH: 22
<212> TYPE: PRT
<213> ORGANISM: Artificial Sequence
<220> FEATURE:
<223> OTHER INFORMATION: LINKER SEQUENCE

<400> SEQUENCE: 60

His Gly Ser Gly Ser Ala Thr Gly Gly Ser Gly Ser Thr Ala Ser Ser
1 5 10 15

Gly Ser Gly Ser Ala Thr
20

<210> SEQ ID NO 61
<211> LENGTH: 19
<212> TYPE: PRT
<213> ORGANISM: Artificial Sequence

<220> FEATURE:
<223> OTHER INFORMATION: LINKER SEQUENCE

<400> SEQUENCE: 61

Ala Glu Ala Ala Ala Lys Glu Ala Ala Ala Lys Glu Ala Ala Ala Lys
1               5                   10                  15

Ala Gly Gly

<210> SEQ ID NO 62
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 62

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 63

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 64

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 65
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 65

His Gly Glu Gly Thr Phe Thr Ser Asp Leu Ser Lys Gln Leu Glu Glu
1               5                   10                  15

```
Glu Ala Val Arg Leu Phe Ile Glu Phe Leu Lys Asn Gly Gly Pro Ser
            20                  25                  30

Ser Gly Ala Pro Pro Pro Ser
        35


<210> SEQ ID NO 66
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 66

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly Pro Ser
            20                  25                  30

Ser Gly Ala Pro Pro Pro Ser
        35


<210> SEQ ID NO 67
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 67

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30


<210> SEQ ID NO 68
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 68

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly
            20                  25                  30


<210> SEQ ID NO 69
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 69

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30


<210> SEQ ID NO 70
<211> LENGTH: 30
<212> TYPE: PRT
<213> ORGANISM: Artificial Sequence
```

```
<220> FEATURE:
<223> OTHER INFORMATION: GLP-1 OR GLP-1 ANALOG

<400> SEQUENCE: 70

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly
            20                  25                  30


<210> SEQ ID NO 71
<211> LENGTH: 28
<212> TYPE: PRT
<213> ORGANISM: Artificial Sequence
<220> FEATURE:
<223> OTHER INFORMATION: GLP-1 OR GLP-1 ANALOG

<400> SEQUENCE: 71

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25


<210> SEQ ID NO 72
<211> LENGTH: 28
<212> TYPE: PRT
<213> ORGANISM: Artificial Sequence
<220> FEATURE:
<223> OTHER INFORMATION: GLP-1 OR GLP-1 ANALOG

<400> SEQUENCE: 72

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25


<210> SEQ ID NO 73
<211> LENGTH: 28
<212> TYPE: PRT
<213> ORGANISM: Artificial Sequence
<220> FEATURE:
<223> OTHER INFORMATION: GLP-1 OR GLP-1 ANALOG

<400> SEQUENCE: 73

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25


<210> SEQ ID NO 74
<211> LENGTH: 28
<212> TYPE: PRT
<213> ORGANISM: Artificial Sequence
<220> FEATURE:
<223> OTHER INFORMATION: GLP-1 OR GLP-1 ANALOG

<400> SEQUENCE: 74

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25


<210> SEQ ID NO 75
<211> LENGTH: 39
<212> TYPE: PRT
```

```
<213> ORGANISM: Artificial Sequence
<220> FEATURE:
<223> OTHER INFORMATION: GLP-1 OR GLP-1 ANALOG

<400> SEQUENCE: 75

His Gly Glu Gly Thr Phe Thr Ser Asp Leu Ser Lys Gln Leu Glu Glu
1               5                   10                  15

Lys Ala Ala Lys Glu Phe Ile Glu Phe Leu Lys Gln Gly Gly Pro Ser
            20                  25                  30

Ser Gly Ala Pro Pro Pro Ser
        35


<210> SEQ ID NO 76
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 76

His Gly Glu Gly Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35


<210> SEQ ID NO 77
<211> LENGTH: 39
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (14)..(14)
<223> OTHER INFORMATION: X at position 13 is octylG

<400> SEQUENCE: 77

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35


<210> SEQ ID NO 78
<211> LENGTH: 39
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (34)..(34)
<223> OTHER INFORMATION: X at position 34 is octylG

<400> SEQUENCE: 78

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Ser Xaa Ala Pro Pro Pro Ser
        35
```

-continued

<210> SEQ ID NO 79
<211> LENGTH: 37
<212> TYPE: PRT
<213> ORGANISM: Artificial Sequence
<220> FEATURE:
<223> OTHER INFORMATION: GLP-1 OR GLP-1 ANALOG

<400> SEQUENCE: 79

```
His Gly Glu Phe Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35
```

<210> SEQ ID NO 80
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 80

```
His Gly Glu Phe Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35
```

<210> SEQ ID NO 81
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 81

```
His Gly Glu Gly Thr Phe Thr Ser Asp Leu Val Lys Ile Leu Glu Ala
1               5                   10                  15

Glu Ala Val Arg Lys Phe Ile Glu Phe Leu Lys Asn Gly Gly Pro Ser
            20                  25                  30

Ser Gly Ala Pro Pro Pro Ser
        35
```

<210> SEQ ID NO 82
<211> LENGTH: 40
<212> TYPE: PRT
<213> ORGANISM: Artificial Sequence
<220> FEATURE:
<223> OTHER INFORMATION: GLP-1 OR GLP-1 ANALOG

<400> SEQUENCE: 82

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40
```

<210> SEQ ID NO 83

<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 83

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 84
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 84

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg
20 25 30

<210> SEQ ID NO 85
<211> LENGTH: 30
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (29)..(29)
<223> OTHER INFORMATION: Xaa at Position 29 is Aib

<400> SEQUENCE: 85

His Xaa Glu Gly Thr Phe Thr Ser Asp Val Ser Ser Tyr Leu Glu Gly
1 5 10 15

Gln Ala Ala Arg Glu Phe Ile Ala Phe Leu Val Arg Xaa Arg
20 25 30

<210> SEQ ID NO 86
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at position 2 is A, V, or G
<220> FEATURE:
<221> NAME/KEY: MISC_FEATURE
<222> LOCATION: (16)..(16)
<223> OTHER INFORMATION: Xaa at position 16 is G, K, or E
<220> FEATURE:
<221> NAME/KEY: MISC_FEATURE
<222> LOCATION: (17)..(17)
<223> OTHER INFORMATION: Xaa at position 17 is Q or K
<220> FEATURE:
<221> NAME/KEY: MISC_FEATURE
<222> LOCATION: (24)..(24)
<223> OTHER INFORMATION: Xaa at position 24 is A or E
<220> FEATURE:
<221> NAME/KEY: MISC_FEATURE
<222> LOCATION: (27)..(27)
<223> OTHER INFORMATION: Xaa at position 27 is V or K
<220> FEATURE:
<221> NAME/KEY: MISC_FEATURE
<222> LOCATION: (28)..(28)
<223> OTHER INFORMATION: Xaa at position 28 is K, N, or R
<220> FEATURE:
<221> NAME/KEY: MISC_FEATURE
<222> LOCATION: (30)..(30)
<223> OTHER INFORMATION: Xaa at position 30 is R or G
<220> FEATURE:
<221> NAME/KEY: MISC_FEATURE
<222> LOCATION: (31)..(31)
<223> OTHER INFORMATION: Xaa at position 31 is G, H, P, or Absent

<400> SEQUENCE: 86

```
His Xaa Glu Gly Thr Phe Thr Ser Asp Val Ser Ser Tyr Leu Glu Xaa
1               5                   10                  15

Xaa Ala Ala Lys Glu Phe Ile Xaa Trp Leu Xaa Xaa Gly Xaa Xaa
            20                  25                  30
```

<210> SEQ ID NO 87
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 87

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

<210> SEQ ID NO 88
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 88

```
His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30
```

<210> SEQ ID NO 89
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 89

```
His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30
```

<210> SEQ ID NO 90
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 90

His Gly Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly Gly
20 25 30

<210> SEQ ID NO 91
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 91

His Val Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly Gly
20 25 30

<210> SEQ ID NO 92
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 92

His Gly Glu Gly Thr Phe Thr Ser Asp Val Ser Ser Tyr Leu Glu Glu
1 5 10 15

Gln Ala Ala Lys Glu Phe Ile Ala Trp Leu Lys Asn Gly Gly Gly
20 25 30

<210> SEQ ID NO 93
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 93

His Val Glu Gly Thr Phe Thr Ser Asp Val Ser Ser Tyr Leu Glu Glu
1 5 10 15

Gln Ala Ala Lys Glu Phe Ile Ala Trp Leu Lys Asn Gly Gly Gly
20 25 30

<210> SEQ ID NO 94
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 94

His Gly Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly Pro
20 25 30

<210> SEQ ID NO 95
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 95

His Val Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly Pro
20 25 30

<210> SEQ ID NO 96
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 96

His Gly Glu Gly Thr Phe Thr Ser Asp Val Ser Ser Tyr Leu Glu Glu
1 5 10 15

Gln Ala Ala Lys Glu Phe Ile Ala Trp Leu Lys Asn Gly Gly Pro
20 25 30

<210> SEQ ID NO 97
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 97

His Val Glu Gly Thr Phe Thr Ser Asp Val Ser Ser Tyr Leu Glu Glu
1 5 10 15

Gln Ala Ala Lys Glu Phe Ile Ala Trp Leu Lys Asn Gly Gly Pro
20 25 30

<210> SEQ ID NO 98
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 98

His Gly Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly
20 25 30

<210> SEQ ID NO 99
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 99

His Val Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly
20 25 30

<210> SEQ ID NO 100
<211> LENGTH: 30
<212> TYPE: PRT
<213> ORGANISM: Artificial Sequence
<220> FEATURE:

<223> OTHER INFORMATION: GLP-1 OR GLP-1 ANALOG

<400> SEQUENCE: 100

His Val Glu Gly Thr Phe Thr Ser Asp Val Ser Ser Tyr Leu Glu Glu
1 5 10 15

Gln Ala Ala Lys Glu Phe Ile Ala Trp Leu Val Asn Gly Gly
20 25 30

<210> SEQ ID NO 101
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 101

His Gly Glu Gly Thr Phe Thr Ser Asp Val Ser Ser Tyr Leu Glu Glu
1 5 10 15

Gln Ala Ala Lys Glu Phe Ile Ala Trp Leu Val Asn Gly Gly
20 25 30

<210> SEQ ID NO 102
<211> LENGTH: 40
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is D-Ala, G, V, L, I, S or T
<220> FEATURE:
<221> NAME/KEY: MISC_FEATURE
<222> LOCATION: (16)..(16)
<223> OTHER INFORMATION: Xaa at Position 16 is G, E, D or K
<220> FEATURE:
<221> NAME/KEY: MISC_FEATURE
<222> LOCATION: (27)..(27)
<223> OTHER INFORMATION: Xaa at Position 27 is V or I

<400> SEQUENCE: 102

His Xaa Glu Gly Thr Phe Thr Ser Asp Val Ser Ser Tyr Leu Glu Xaa
1 5 10 15

Gln Ala Ala Lys Glu Phe Ile Ala Trp Leu Xaa Lys Gly Gly Pro Ser
20 25 30

Ser Gly Ala Pro Pro Pro Cys Cys
35 40

<210> SEQ ID NO 103
<211> LENGTH: 40
<212> TYPE: PRT
<213> ORGANISM: Artificial Sequence
<220> FEATURE:
<223> OTHER INFORMATION: GLP-1 OR GLP-1 ANALOG

<400> SEQUENCE: 103

His Val Glu Gly Thr Phe Thr Ser Asp Val Ser Ser Tyr Leu Glu Glu
1 5 10 15

Gln Ala Ala Lys Glu Phe Ile Ala Trp Leu Ile Lys Gly Gly Pro Ser
20 25 30

Ser Gly Ala Pro Pro Pro Cys Cys
35 40

<210> SEQ ID NO 104
<211> LENGTH: 39

<212> TYPE: PRT
<213> ORGANISM: Artificial Sequence
<220> FEATURE:
<223> OTHER INFORMATION: GLP-1 OR GLP-1 ANALOG

<400> SEQUENCE: 104

```
His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35
```

<210> SEQ ID NO 105
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 105

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Lys
            20                  25                  30

Ser Gly Ala Pro Pro Pro Ser
        35
```

<210> SEQ ID NO 106
<211> LENGTH: 38
<212> TYPE: PRT
<213> ORGANISM: Artificial Sequence
<220> FEATURE:
<223> OTHER INFORMATION: GLP-1 OR GLP-1 ANALOG

<400> SEQUENCE: 106

```
Gly Glu Gly Thr Phe Thr Ser Asp Leu Ser Lys Gln Met Glu Glu Glu
1               5                   10                  15

Ala Val Lys Leu Phe Ile Glu Trp Leu Lys Asn Gly Gly Pro Ser Ser
            20                  25                  30

Gly Ala Pro Pro Pro Ser
        35
```

<210> SEQ ID NO 107
<211> LENGTH: 39
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (14)..(14)
<223> OTHER INFORMATION: X at Position 14 is NorLe

<400> SEQUENCE: 107

```
His Gly Glu Gly Thr Phe Thr Ser Asp Leu Ser Arg Gln Xaa Glu Glu
1               5                   10                  15

Glu Ala Val Arg Leu Phe Ile Glu Trp Leu Arg Asn Gly Gly Pro Lys
            20                  25                  30

Ser Gly Ala Pro Pro Pro Ser
        35
```

<210> SEQ ID NO 108

<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 108

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 109
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 109

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 110
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 110

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 111
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 111

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 112
<211> LENGTH: 40
<212> TYPE: PRT
<213> ORGANISM: Artificial Sequence

```
<220> FEATURE:
<223> OTHER INFORMATION: GLP-1 OR GLP-1 ANALOG

<400> SEQUENCE: 112

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40


<210> SEQ ID NO 113
<211> LENGTH: 40
<212> TYPE: PRT
<213> ORGANISM: Artificial Sequence
<220> FEATURE:
<223> OTHER INFORMATION: GLP-1 OR GLP-1 ANALOG

<400> SEQUENCE: 113

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40


<210> SEQ ID NO 114
<211> LENGTH: 40
<212> TYPE: PRT
<213> ORGANISM: Artificial Sequence
<220> FEATURE:
<223> OTHER INFORMATION: GLP-1 OR GLP-1 ANALOG

<400> SEQUENCE: 114

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40


<210> SEQ ID NO 115
<211> LENGTH: 40
<212> TYPE: PRT
<213> ORGANISM: Artificial Sequence
<220> FEATURE:
<223> OTHER INFORMATION: GLP-1 OR GLP-1 ANALOG

<400> SEQUENCE: 115

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40


<210> SEQ ID NO 116
<211> LENGTH: 40
<212> TYPE: PRT
<213> ORGANISM: Artificial Sequence
<220> FEATURE:
<223> OTHER INFORMATION: GLP-1 OR GLP-1 ANALOG
```

<400> SEQUENCE: 116

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 117
<211> LENGTH: 40
<212> TYPE: PRT
<213> ORGANISM: Artificial Sequence
<220> FEATURE:
<223> OTHER INFORMATION: GLP-1 OR GLP-1 ANALOG

<400> SEQUENCE: 117

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 118
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 118

Ala Glu Gly Thr Phe Thr Ser Asp Val Ser Ser Tyr Leu Glu Gly Gln
1               5                   10                  15

Ala Ala Arg Glu Phe Ile Ala Trp Leu Val Lys Gly Arg Gly
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: GLP-1 OR GLP-1 ANALOG

<400> SEQUENCE: 119

Ala Glu Gly Thr Phe Thr Ser Asp Val Ser Ser Tyr Leu Glu Gly Gln
1               5                   10                  15

Ala Ala Arg Glu Phe Ile Ala Trp Leu Val Lys Gly Arg Gly
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: GLP-1 OR GLP-1 ANALOG

<400> SEQUENCE: 120

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: GLP-1 OR GLP-1 ANALOG

<400> SEQUENCE: 121

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Arg Gly Lys
            20                  25                  30

<210> SEQ ID NO 122
<211> LENGTH: 33
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib
<220> FEATURE:
<221> NAME/KEY: MISC_FEATURE
<222> LOCATION: (31)..(32)
<223> OTHER INFORMATION: Xaa at Position 31 and 32 is Aeea

<400> SEQUENCE: 122

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Lys Asn Gly Gly Xaa Xaa
            20                  25                  30

Lys

<210> SEQ ID NO 123
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Postiion 2 is Aib
<220> FEATURE:
<221> NAME/KEY: MISC_FEATURE
<222> LOCATION: (16)..(16)
<223> OTHER INFORMATION: Xaa at Postiion 2 is Aib

<400> SEQUENCE: 123

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Gly Gly
            20                  25                  30

<210> SEQ ID NO 124
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)

```
<223> OTHER INFORMATION: Xaa at Position 2 is Aib

<400> SEQUENCE: 124

His Xaa Glu Gly Thr Phe Thr Ser Asp Val Ser Ser Tyr Leu Glu Gly
1               5                   10                  15

Glu Ala Ala Lys Lys Phe Ile Ala Trp Leu Val Lys Gly Gly Gly
            20                  25                  30


<210> SEQ ID NO 125
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at position 2 is Aib

<400> SEQUENCE: 125

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Lys
            20                  25                  30


<210> SEQ ID NO 126
<211> LENGTH: 39
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 126

His Xaa Glu Gly Thr Phe Thr Ser Asp Val Ser Ser Tyr Leu Glu Xaa
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35


<210> SEQ ID NO 127
<211> LENGTH: 31
<212> TYPE: PRT
<213> ORGANISM: Artificial Sequence
<220> FEATURE:
<223> OTHER INFORMATION: GLP-1 OR GLP-1 ANALOG

<400> SEQUENCE: 127

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30


<210> SEQ ID NO 128
<211> LENGTH: 31
<212> TYPE: PRT
<213> ORGANISM: Artificial Sequence
<220> FEATURE:
```

```
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib

<400> SEQUENCE: 128

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30


<210> SEQ ID NO 129
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib

<400> SEQUENCE: 129

His Xaa Glu Gly Thr Phe Thr Ser Asp Tyr Ser Ser Tyr Leu Glu Glu
1               5                   10                  15

Gln Ala Ala Lys Glu Phe Ile Ala Trp Leu Val Lys Gly Gly Gly
            20                  25                  30


<210> SEQ ID NO 130
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib

<400> SEQUENCE: 130

His Xaa Glu Gly Thr Phe Thr Ser Asp Val Ser Lys Tyr Leu Glu Glu
1               5                   10                  15

Glu Ala Val Arg Leu Phe Ile Glu Trp Leu Lys Asn Gly Gly Gly
            20                  25                  30


<210> SEQ ID NO 131
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib

<400> SEQUENCE: 131

His Xaa Glu Gly Thr Phe Thr Ser Asp Val Ser Lys Tyr Leu Glu Glu
1               5                   10                  15

Glu Ala Ala Lys Leu Phe Ile Glu Trp Leu Lys Asn Gly Gly Gly
            20                  25                  30


<210> SEQ ID NO 132
<211> LENGTH: 31
<212> TYPE: PRT
<213> ORGANISM: Artificial Sequence
```

```
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib

<400> SEQUENCE: 132

His Xaa Glu Gly Thr Phe Thr Ser Asp Val Ser Lys Tyr Leu Glu Glu
1               5                   10                  15

Glu Ala Ala Lys Leu Phe Ile Glu Trp Leu Val Lys Gly Gly Gly
            20                  25                  30


<210> SEQ ID NO 133
<211> LENGTH: 30
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 133

His Xaa Ile Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Gly
            20                  25                  30


<210> SEQ ID NO 134
<211> LENGTH: 30
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 134

His Xaa Glu Gly Thr Phe Thr Ser Glu Val Ser Ser Tyr Leu Glu Xaa
1               5                   10                  15

Gln Ala Ala Lys Glu Phe Ile Ala Trp Leu Val Lys Gly Gly
            20                  25                  30


<210> SEQ ID NO 135
<211> LENGTH: 30
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib
```

<400> SEQUENCE: 135

His Xaa Ala Gly Thr Phe Thr Ser Asp Val Ser Ser Tyr Leu Glu Xaa
1 5 10 15

Gln Ala Ala Lys Glu Phe Ile Ala Trp Leu Val Lys Gly Gly
20 25 30

<210> SEQ ID NO 136
<211> LENGTH: 30
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 136

His Xaa Glu Gly Thr Phe Thr Ser Asp Val Ser Ser Tyr Leu Glu Xaa
1 5 10 15

Gln Ala Ala Lys Glu Phe Ala Ala Trp Leu Val Lys Gly Gly
20 25 30

<210> SEQ ID NO 137
<211> LENGTH: 30
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 137

His Xaa Glu Gly Thr Phe Thr Ser Asp Val Ser Ser Tyr Leu Glu Xaa
1 5 10 15

Gln Ala Ala Lys Glu Phe Ile Ala Ala Leu Val Lys Gly Gly
20 25 30

<210> SEQ ID NO 138
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 138

His Xaa Thr Gly Thr Phe Thr Ser Asp Val Ser Ser Tyr Leu Glu Xaa
1 5 10 15

Gln Ala Ala Lys Glu Phe Ile Ala Trp Leu Val Lys Gly Gly Gly
20 25 30

<210> SEQ ID NO 139
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 139

```
His Xaa Glu Gly Thr Phe Thr Ser Glu Val Ser Ser Tyr Leu Glu Xaa
1               5                   10                  15

Gln Ala Ala Lys Glu Phe Ile Ala Ala Leu Val Lys Gly Gly Gly
            20                  25                  30
```

<210> SEQ ID NO 140
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 140

```
His Xaa Glu Gly Thr Phe Thr Ser Asp Val Ser Ser Tyr Leu Glu Xaa
1               5                   10                  15

Gln Ala Ala Lys Glu Phe Ile Ala Ala Leu Val Lys Gly Gly Gly
            20                  25                  30
```

<210> SEQ ID NO 141
<211> LENGTH: 39
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib

<400> SEQUENCE: 141

```
His Xaa Glu Gly Thr Phe Thr Ser Asp Val Ser Ser Tyr Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 142
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 142

His Xaa Glu Gly Thr Phe Thr Ser Asp Tyr Ser Ser Tyr Leu Glu Xaa
1               5                   10                  15

Gln Ala Ala Lys Glu Phe Ile Ala Trp Leu Val Lys Gly Gly Gly
            20                  25                  30

<210> SEQ ID NO 143
<211> LENGTH: 31
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (2)..(2)
<223> OTHER INFORMATION: Xaa at Position 2 is Aib
<220> FEATURE:
<221> NAME/KEY: MISC_FEATURE
<222> LOCATION: (16)..(16)
<223> OTHER INFORMATION: Xaa at Position 16 is Aib

<400> SEQUENCE: 143

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Gly Gly
            20                  25                  30

<210> SEQ ID NO 144
<211> LENGTH: 29
<212> TYPE: PRT
<213> ORGANISM: Artificial Sequence
<220> FEATURE:
<223> OTHER INFORMATION: GLP-1 OR GLP-1 ANALOG
<220> FEATURE:
<221> NAME/KEY: MISC_FEATURE
<222> LOCATION: (1)..(1)
<223> OTHER INFORMATION: Xaa at Position 1 is dimethyl imidazole acetic
      acid (Dmia)

<400> SEQUENCE: 144

Xaa Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr
            20                  25

<210> SEQ ID NO 145
<211> LENGTH: 324
<212> TYPE: DNA
<213> ORGANISM: Artificial Sequence
<220> FEATURE:
<223> OTHER INFORMATION: ANTIBODY OR ANTIBODY PORTION

<400> SEQUENCE: 145
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcagccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctctcac tttcggcgga 300
gggaccaagg tggagatcaa acga 324

<210> SEQ ID NO 146
<211> LENGTH: 360
<212> TYPE: DNA
<213> ORGANISM: Artificial Sequence
<220> FEATURE:
<223> OTHER INFORMATION: ANTIBODY OR ANTIBODY PORTION

<400> SEQUENCE: 146
caggtgcagc tggtggagtc tgggggaggc gtggtccagc ctgggaggtc cctgagactc 60
tcctgtgcag catctggatt caccttcagt aactatggca tgcactgggt ccgccaggct 120
ccaggcgagg ggctggagtg ggtggcagct atatggtttg atgcaagtga taaatactat 180
gcagacgccg tgaagggccg attcaccatc tccagagaca actccaagaa cacgctgtat 240
ctgcaaatga acagcctgag agccgaggac acggctgtgt attactgtgc gagagatcag 300
gcgatttttg gagtggtccc cgactactgg ggccagggaa ccctggtcac cgtctcctca 360

<210> SEQ ID NO 147
<211> LENGTH: 108
<212> TYPE: PRT
<213> ORGANISM: Artificial Sequence
<220> FEATURE:
<223> OTHER INFORMATION: ANTIBODY OR ANTIBODY PORTION

<400> SEQUENCE: 147

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg
            100                 105

<210> SEQ ID NO 148
<211> LENGTH: 120
<212> TYPE: PRT
<213> ORGANISM: Artificial Sequence
<220> FEATURE:
<223> OTHER INFORMATION: ANTIBODY OR ANTIBODY PORTION

<400> SEQUENCE: 148

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
    50                  55                  60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser
        115                 120


<210> SEQ ID NO 149
<211> LENGTH: 642
<212> TYPE: DNA
<213> ORGANISM: Artificial Sequence
<220> FEATURE:
<223> OTHER INFORMATION: ANTIBODY OR ANTIBODY PORTION

<400> SEQUENCE: 149

gaaatagtga tgacgcagtc tccagccacc ctgtctgtgt ctccagggga aagagccacc      60

ctctcctgca gggccagtca gagtgttagc agcaacttag cctggtacca gcagaaacct     120

ggccaggctc ccaggctcct catctatggt gcagccacca gggccactgg tatcccagcc     180

aggttcagtg gcagtgggtc tgggacagag ttcactctca ccatcagcag cctgcagtct     240

gaagattttg cagtttatta ctgtcagcag tataataact ggcctctcac tttcggcgga     300

gggaccaagg tggagatcaa acgaacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 150
<211> LENGTH: 1350
<212> TYPE: DNA
<213> ORGANISM: Artificial Sequence
<220> FEATURE:
<223> OTHER INFORMATION: ANTIBODY OR ANTIBODY PORTION

<400> SEQUENCE: 150

caggtgcagc tggtggagtc tgggggaggc gtggtccagc ctgggaggtc cctgagactc      60

tcctgtgcag catctggatt caccttcagt aactatggca tgcactgggt ccgccaggct     120

ccaggcgagg ggctggagtg ggtggcagct atatggtttg atgcaagtga taaatactat     180

gcagacgccg tgaagggccg attcaccatc tccagagaca actccaagaa cacgctgtat     240

ctgcaaatga acagcctgag agccgaggac acggctgtgt attactgtgc gagagatcag     300

gcgatttttg gagtggtccc cgactactgg ggccagggaa ccctggtcac cgtctcctca     360

gcctccacca agggcccatc ggtcttcccc ctggcaccct cctccaagag cacctctggg     420

ggcacagcgg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgacc gtgccctcca gcagcttggg cacccagacc     600

tacatctgca acgtgaatca caagcccagc aacaccaagg tggacaagaa agttgagccc     660

aaatcttgtg acaaaactca cacatgccca ccgtgcccag cacctgaact cctgggggga     720
```

-continued

```
ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgtgtgagga gcagtacggc    900

agcacgtacc gttgtgtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggaggag   1080

atgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctat agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350


<210> SEQ ID NO 151
<211> LENGTH: 215
<212> TYPE: PRT
<213> ORGANISM: Artificial Sequence
<220> FEATURE:
<223> OTHER INFORMATION: ANTIBODY OR ANTIBODY PORTION

<400> SEQUENCE: 151

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Leu Asn Arg Gly Glu Cys
    210                 215


<210> SEQ ID NO 152
<211> LENGTH: 450
<212> TYPE: PRT
<213> ORGANISM: Artificial Sequence
```

<220> FEATURE:
<223> OTHER INFORMATION: ANTIBODY OR ANTIBODY PORTION

<400> SEQUENCE: 152

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

-continued

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 153
<211> LENGTH: 33
<212> TYPE: DNA
<213> ORGANISM: Artificial Sequence
<220> FEATURE:
<223> OTHER INFORMATION: ANTIBODY OR ANTIBODY PORTION

<400> SEQUENCE: 153
agggccagtc agagtgttag cagcaactta gcc 33

<210> SEQ ID NO 154
<211> LENGTH: 21
<212> TYPE: DNA
<213> ORGANISM: Artificial Sequence
<220> FEATURE:
<223> OTHER INFORMATION: ANTIBODY OR ANTIBODY PORTION

<400> SEQUENCE: 154
ggtgcagcca ccagggccac t 21

<210> SEQ ID NO 155
<211> LENGTH: 27
<212> TYPE: DNA
<213> ORGANISM: Artificial Sequence
<220> FEATURE:
<223> OTHER INFORMATION: ANTIBODY OR ANTIBODY PORTION

<400> SEQUENCE: 155
cagcagtata ataactggcc tctcact 27

<210> SEQ ID NO 156
<211> LENGTH: 11
<212> TYPE: PRT
<213> ORGANISM: Artificial Sequence
<220> FEATURE:
<223> OTHER INFORMATION: ANTIBODY OR ANTIBODY PORTION

<400> SEQUENCE: 156

```
Arg Ala Ser Gln Ser Val Ser Ser Asn Leu Ala
1               5                   10
```

<210> SEQ ID NO 157
<211> LENGTH: 7
<212> TYPE: PRT
<213> ORGANISM: Artificial Sequence
<220> FEATURE:
<223> OTHER INFORMATION: ANTIBODY OR ANTIBODY PORTION

<400> SEQUENCE: 157

```
Gly Ala Ala Thr Arg Ala Thr
1               5
```

<210> SEQ ID NO 158
<211> LENGTH: 9
<212> TYPE: PRT

<213> ORGANISM: Artificial Sequence
<220> FEATURE:
<223> OTHER INFORMATION: ANTIBODY OR ANTIBODY PORTION

<400> SEQUENCE: 158

Gln Gln Tyr Asn Asn Trp Pro Leu Thr
1 5

<210> SEQ ID NO 159
<211> LENGTH: 15
<212> TYPE: DNA
<213> ORGANISM: Artificial Sequence
<220> FEATURE:
<223> OTHER INFORMATION: ANTIBODY OR ANTIBODY PORTION

<400> SEQUENCE: 159
aactatggca tgcac 15

<210> SEQ ID NO 160
<211> LENGTH: 51
<212> TYPE: DNA
<213> ORGANISM: Artificial Sequence
<220> FEATURE:
<223> OTHER INFORMATION: ANTIBODY OR ANTIBODY PORTION

<400> SEQUENCE: 160
gctatatggt ttgatgcaag tgataaatac tatgcagacg ccgtgaaggg c 51

<210> SEQ ID NO 161
<211> LENGTH: 33
<212> TYPE: DNA
<213> ORGANISM: Artificial Sequence
<220> FEATURE:
<223> OTHER INFORMATION: ANTIBODY OR ANTIBODY PORTION

<400> SEQUENCE: 161
gatcaggcga tttttggagt ggtccccgac tac 33

<210> SEQ ID NO 162
<211> LENGTH: 5
<212> TYPE: PRT
<213> ORGANISM: Artificial Sequence
<220> FEATURE:
<223> OTHER INFORMATION: ANTIBODY OR ANTIBODY PORTION

<400> SEQUENCE: 162

Asn Tyr Gly Met His
1 5

<210> SEQ ID NO 163
<211> LENGTH: 17
<212> TYPE: PRT
<213> ORGANISM: Artificial Sequence
<220> FEATURE:
<223> OTHER INFORMATION: ANTIBODY OR ANTIBODY PORTION

<400> SEQUENCE: 163

Ala Ile Trp Phe Asp Ala Ser Asp Lys Tyr Tyr Ala Asp Ala Val Lys
1 5 10 15

Gly

<210> SEQ ID NO 164
<211> LENGTH: 11
<212> TYPE: PRT
<213> ORGANISM: Artificial Sequence
<220> FEATURE:

-continued

```
<223> OTHER INFORMATION: ANTIBODY OR ANTIBODY PORTION

<400> SEQUENCE: 164

Asp Gln Ala Ile Phe Gly Val Val Pro Asp Tyr
1               5                   10


<210> SEQ ID NO 165
<211> LENGTH: 39
<212> TYPE: PRT
<213> ORGANISM: Artificial Sequence
<220> FEATURE:
<223> OTHER INFORMATION: GLP-1 OR GLP-1 ANALOG

<400> SEQUENCE: 165

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

METHOD OF CONJUGATION OF CYS-MABS

CROSS-REFERENCE TO RELATED APPLICATIONS

This application is a national stage application under 35 U.S.C. § 371 of International Application No. PCT/US2018/0345212, having an international filing date of Aug. 3, 2018, which claims the benefit of U.S. Provisional Patent Application No. 62/541,522, filed Aug. 4, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 2, 2018, is named A-2188-US-PCT_SeqList080218_st25.txt and is 76 kilobytes in size.

FIELD OF THE INVENTION

The present disclosure relates to a method of capping, reducing, and oxidizing cys-mAbs in order to provide homogenous material for subsequent conjugation reactions.

BACKGROUND OF THE INVENTION

Conjugated biomolecules are a diverse array of substances that comprise multiple precursor molecules, at least one of which is derived from a biological system. Most often, the biologically derived component(s) are produced using recombinant DNA techniques. In the pharmaceutical industry, conjugated biomolecules have been investigated as treatments for a variety of medical conditions. In these cases, the conjugate can provide a number of therapeutic benefits by combining useful properties of two or more precursor molecules into a single entity.

One particularly successful class of pharmaceutical bioconjugates are antibody conjugates, also called antibody-drug conjugates. These molecules consist of an antibody, typically derived from mammalian cell culture, and a synthetic molecule with biologic or pharmacologic activity. Several antibody-drug conjugates have been approved as cancer therapies, and many more are in clinical and preclinical development. All of the antibody-drug conjugates that have been approved to date are manufactured using non-specific chemistry that produces a mixture of conjugated molecules.

Pharmaceuticals based on site-specific antibody conjugates, where a synthetic molecule is attached at defined sites in the antibody molecule, can provide therapeutic benefits as well as improved quality control and/or shelf life. Numerous efforts have therefore been undertaken to develop methods for producing site-specific conjugates of antibodies. A common approach to site-specific conjugation is the use of a cysteine mutant antibody (Cys-mAb or Thiomab), in which a new cysteine amino acid is introduced into the antibody primary structure. This engineered cysteine can be used as a site for conjugating a synthetic molecule.

Site-specific conjugation with a Cys-mAb protein requires the engineered cysteine side chain in the reduced thiol form. However, when antibodies are isolated from mammalian cell culture, the engineered cysteine is generally "capped" as a mixed disulfide with a cytoplasmic thiol such as glutathione. Thus directly adding the reactive synthetic molecule will not produce the conjugate since the side chain of the engineered cysteine is not available to react.

A single step selective reduction to remove the cap would be highly desirable, but is currently not feasible due to the chemical similarity between the mixed disulfide and the structural disulfides in the antibody. When a reducing agent is added to the Cys-mAb to remove the caps, some portion of the other disulfides in the antibody will also be reduced, and the resulting thiols can react to form conjugates at undesired locations.

Accordingly, there remains a need for efficient, robust ways to manufacture conjugates of cysteine-engineered antibodies that offer high yield and consistent product quality.

SUMMARY OF THE INVENTION

In one aspect, the present disclosure provides a method for preparing an antibody conjugate or antibody fragment conjugate, the method comprising the steps of: a) obtaining a composition comprising an antibody or antibody fragment; b) exposing the antibody or antibody fragment to a cysteine blocking agent, wherein the cysteine blocking agent forms a stable mixed-disulfide with at least one cysteine residue of the antibody or antibody fragment; c) adding a reducing agent to the composition to form a reduction mix and allowing a reduction reaction to occur such that the reduction mix comprises a reduced antibody or reduced antibody fragment; d) adding an oxidizing agent to the reduction mix to form an oxidized mix and allowing an oxidizing reaction to occur such that the oxidizing mix comprises an oxidized antibody or oxidized antibody fragment; and e) adding an activated chemical moiety to the oxidized mix to form a conjugation mix and allowing a conjugation reaction to occur such that an antibody conjugate or antibody fragment conjugate is formed.

In one aspect, following step b) and before step c) cation exchange chromatography is performed to remove excess cysteine blocking agent. In one aspect, following step c) and before step d) a buffer exchange step is performed to remove the reducing agent. In one embodiment, the buffer exchange step is ultrafiltration/diafiltration. In one aspect, following step e), a purification step is performed to remove the activated chemical moiety. In one embodiment, the purification step includes hydrophobic interaction chromatography ("HIC"), ultrafiltration/diafiltration, or hydrophobic interaction chromatography ("HIC") followed by ultrafiltration/diafiltration.

In another aspect, the present disclosure provides a method for preparing an antibody conjugate or antibody fragment conjugate, the method comprising the steps of: a) obtaining a composition comprising a mixed disulfide comprising an antibody or antibody fragment; b) adding a reducing agent to the composition to form a reduction mix and allowing a reduction reaction to occur such that the reduction mix comprises a reduced antibody or reduced antibody fragment; c) adding an oxidizing agent to the reduction mix to form an oxidized mix and allowing an oxidizing reaction to occur such that the oxidizing mix comprises an oxidized antibody or oxidized antibody fragment; and d) adding an activated chemical moiety to the oxidized mix to form a conjugation mix and allowing a conjugation reaction to occur such that an antibody conjugate or antibody fragment conjugate is formed.

In one aspect, following step a) and before step b) cation exchange chromatography is performed to remove excess cysteine blocking agent. In one aspect, following step b) and before step c) a buffer exchange step is performed to remove the reducing agent. In one embodiment, the buffer exchange step is ultrafiltration/diafiltration. In one aspect, following step d), a purification step is performed to remove the activated chemical moiety. In one embodiment, the purification step includes hydrophobic interaction chromatography ("HIC"), ultrafiltration/diafiltration, or hydrophobic interaction chromatography ("HIC") followed by ultrafiltration/diafiltration.

In another aspect, the present disclosure provides a method for preparing an antibody conjugate or antibody fragment conjugate, the method comprising the steps of: a) obtaining a composition comprising a mixed disulfide comprising an antibody or antibody fragment; b) adding a reducing agent to the composition to form a reduction mix and allowing a reduction reaction to occur such that the reduction mix comprises a reduced antibody or reduced antibody fragment; c) adding an oxidizing agent to the reduction mix to form an oxidized mix and allowing an oxidizing reaction to occur such that the oxidizing mix comprises an oxidized antibody or oxidized antibody fragment; and d) adding an activated chemical moiety to the oxidized mix to form a conjugation mix and allowing a conjugation reaction to occur such that an antibody conjugate or antibody fragment conjugate is formed.

In one aspect, following step a) and before step b) a buffer exchange step is performed to remove the reducing agent. In one aspect, following step c), a purification step is performed to remove the activated chemical moiety. In one embodiment, the buffer exchange step is ultrafiltration/diafiltration. In one embodiment, the purification step includes hydrophobic interaction chromatography ("HIC"), ultrafiltration/diafiltration, or hydrophobic interaction chromatography ("HIC") followed by ultrafiltration/diafiltration.

In one embodiment, the mixed disulfide is an antibody or antibody fragment with a capped free cysteine. In one embodiment, the antibody or antibody fragment with a capped free cysteine comprises a cap selected from the group consisting of cysteine, cysteamine, cystamine, and glutathione. In one embodiment, the reducing agent is selected from the group consisting of triphenylphosphine-3,3',3"-trisulfonate ("TPPTS"), tris(2-carboxyethyl)phosphine ("TCEP"), and triphenylphosphine-3,3'-disulfonate ("TPPDS"). In one embodiment, the ratio of reducing agent to antibody or antibody fragment is 2 to 4:1 (mole/mole)."). In one embodiment, the oxidizing agent is dehydroascorbic acid ("DHAA")."). In one embodiment, the ratio of oxidizing agent to antibody or antibody fragment is 3 to 6:1 (mole/mole)."). In one embodiment, the activated chemical moiety is a peptide comprising a halogen, wherein the halogen is selected from the group consisting of Br, I, and Cl."). In one embodiment, the ratio of activated chemical moiety to antibody or antibody fragment is 2 to 3:1 (mole/mole).

In one embodiment, the antibody or antibody fragment comprises a cysteine residue at a position selected from the group consisting of D70 of the antibody light chain relative to reference sequence SEQ ID NO: 7; E276 of the antibody heavy chain relative to reference sequence SEQ ID NO: 8; and T363 of the antibody heavy chain relative to reference sequence SEQ ID NO: 8.

DETAILED DESCRIPTION OF THE INVENTION

Figure 1:
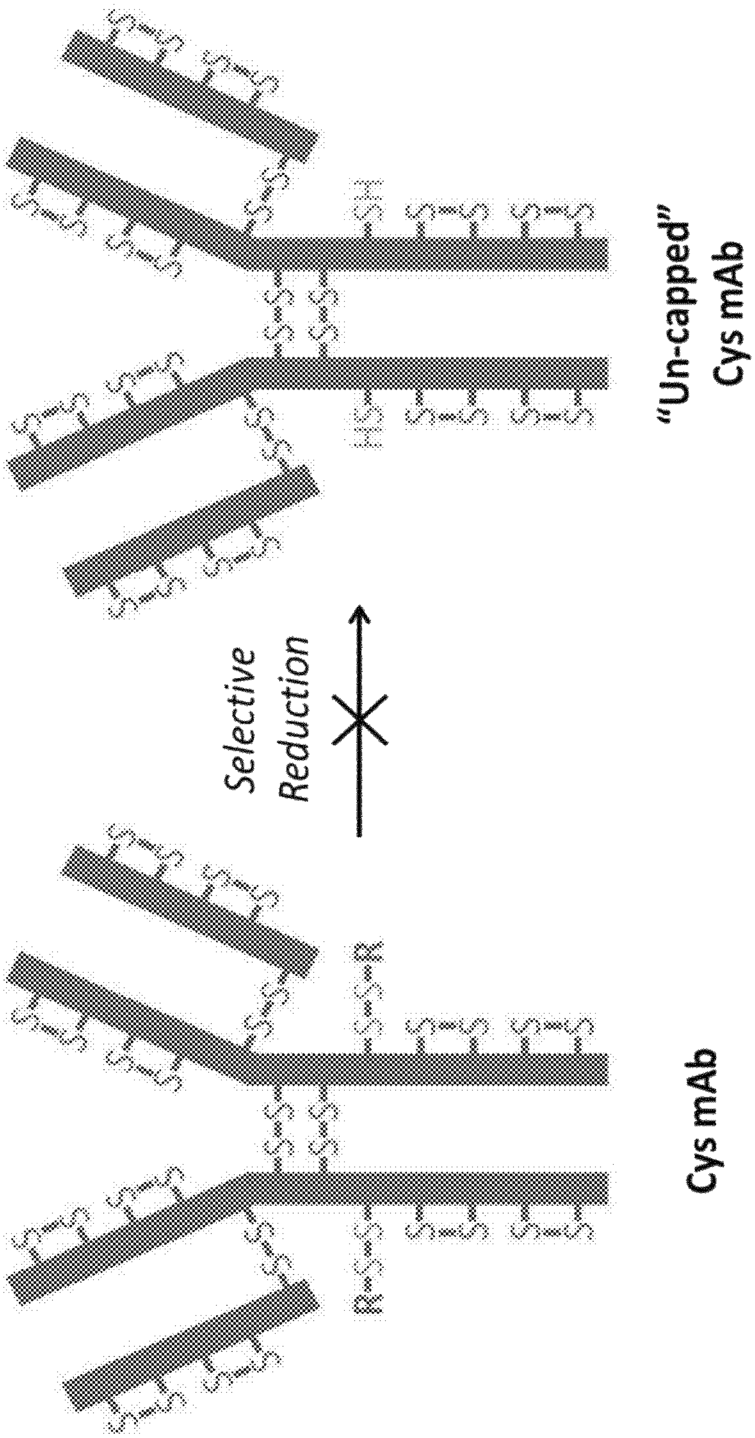
FIG. 1. Typical Cys mAb (IgG1) consisting of four polypeptide chains (two Light Chains, two Heavy Chains) held together by 16 native disulfide bonds (shown in green). Additional cysteines engineered into the antibody carry two additional disulfides (shown in orange). Selective reduction of the engineered disulfides in the presence of other 16 native disulfides would be highly desirable, but is not feasible (in a single step).

The present disclosure provides a method of capping, reducing, and oxidizing cys-mAbs in order to provide homogenous material for subsequent conjugation reactions. The present method demonstrates robust ways to manufacture conjugates of cysteine-engineered antibodies that offer high yield and consistent product quality.

"Free cysteines" have been found to be suitable attachment points for conjugations of various property modifying groups. A free cysteine herein refers to a cysteine residue that is not engaged in an ordinary di-sulfide bond between two cysteine's of one or two polypeptides. Usually a free cysteine will be a cysteine that has been introduced in a polypeptide sequence of interest by site-selective mutagenesis, but some proteins may alternatively include a cysteine in a suitable position. As described in the background, an added cysteine may be a suitable attachment point for a property modifying group to a protein. By introducing a cysteine residue a free cysteine is usually obtained as no partner for forming a di-sulfide bond is present in the protein.

In one aspect, the present disclosure provides a method for preparing an antibody conjugate or antibody fragment conjugate, the method comprising the steps of: a) obtaining a composition comprising an antibody or antibody fragment; b) exposing the antibody or antibody fragment to a cysteine blocking agent, wherein the cysteine blocking agent forms a stable mixed-disulfide with at least one cysteine residue of the antibody or antibody fragment; c) adding a reducing agent to the composition to form a reduction mix and allowing a reduction reaction to occur such that the reduction mix comprises a reduced antibody or reduced antibody fragment; d) adding an oxidizing agent to the reduction mix to form an oxidized mix and allowing an oxidizing reaction to occur such that the oxidizing mix comprises an oxidized antibody or oxidized antibody fragment; and e) adding an activated chemical moiety to the oxidized mix to form a conjugation mix and allowing a conjugation reaction to occur such that an antibody conjugate or antibody fragment conjugate is formed.

In one aspect, following step b) and before step c) cation exchange chromatography is performed to upgrade antibody homogeneity and to remove excess cysteine blocking agent. In one aspect, following step c) and before step d) a buffer exchange step is performed to remove the released caps (thiols) and to remove the reducing agent. In one embodiment, the buffer exchange step is ultrafiltration/diafiltration. In one aspect, following step e), a purification step is performed to remove any excess of the activated chemical moiety and upgrade purity of the antibody or antibody fragment conjugate. In one embodiment, the purification step includes hydrophobic interaction chromatography ("HIC"), ultrafiltration/diafiltration, or hydrophobic interaction chromatography ("HIC") followed by ultrafiltration/diafiltration.

In another aspect, the present disclosure provides a method for preparing an antibody conjugate or antibody fragment conjugate, the method comprising the steps of: a) obtaining a composition comprising a mixed disulfide comprising an antibody or antibody fragment; b) adding a reducing agent to the composition to form a reduction mix and allowing a reduction reaction to occur such that the reduction mix comprises a reduced antibody or reduced antibody fragment; c) adding an oxidizing agent to the reduction mix to form an oxidized mix and allowing an oxidizing reaction to occur such that the oxidizing mix comprises an oxidized antibody or oxidized antibody fragment; and d) adding an activated chemical moiety to the oxidized mix to form a conjugation mix and allowing a conjugation reaction to occur such that an antibody conjugate or antibody fragment conjugate is formed.

In one aspect, following step a) and before step b) cation exchange chromatography is performed to remove excess cysteine blocking agent. In one aspect, following step b) and before step c) a buffer exchange step is performed to remove caps and to remove excess of the reducing agent. In one embodiment, the buffer exchange step is ultrafiltration/diafiltration. In one aspect, following step d), a purification step is performed to remove the activated chemical moiety. In one embodiment, the purification step includes hydrophobic interaction chromatography ("HIC"), ultrafiltration/diafiltration, or hydrophobic interaction chromatography ("HIC") followed by ultrafiltration/diafiltration.

In another aspect, the present disclosure provides a method for preparing an antibody conjugate or antibody fragment conjugate, the method comprising the steps of: a) obtaining a composition comprising a mixed disulfide comprising an antibody or antibody fragment; b) adding a reducing agent to the composition to form a reduction mix and allowing a reduction reaction to occur such that the reduction mix comprises a reduced antibody or reduced antibody fragment; c) adding an oxidizing agent to the reduction mix to form an oxidized mix and allowing an oxidizing reaction to occur such that the oxidizing mix comprises an oxidized antibody or oxidized antibody fragment; and d) adding an activated chemical moiety to the oxidized mix to form a conjugation mix and allowing a conjugation reaction to occur such that an antibody conjugate or antibody fragment conjugate is formed.

In one aspect, following step a) and before step b) a buffer exchange step is performed to remove the reducing agent. In one aspect, following step c), a purification step is performed to remove the activated chemical moiety. In one embodiment, the buffer exchange step is ultrafiltration/diafiltration. In one embodiment, the purification step includes hydrophobic interaction chromatography ("HIC"), ultrafiltration/diafiltration, or hydrophobic interaction chromatography ("HIC") followed by ultrafiltration/diafiltration.

In one embodiment, the mixed disulfide is an antibody or antibody fragment with a capped free cysteine. In one embodiment, the antibody or antibody fragment with a capped free cysteine comprises a cap selected from the group consisting of cysteine, cysteamine, cystamine, and glutathione. In one embodiment, the reducing agent is selected from the group consisting of triphenylphosphine-3,3',3"-trisulfonate ("TPPTS"), tris(2-carboxyethyl)phosphine ("TCEP"), and triphenylphosphine-3,3'-disulfonate ("TPPDS"). In one embodiment, the ratio of reducing agent to antibody or antibody fragment is 2 to 4:1 (mole/mole)."). In one embodiment, the oxidizing agent is dehydroascorbic acid ("DHAA")."). In one embodiment, the ratio of oxidizing agent to antibody or antibody fragment is 3 to 6:1 (mole/mole)."). In one embodiment, the activated chemical moiety is a peptide comprising a halogen, wherein the halogen is selected from the group consisting of Br, I, and Cl."). In one embodiment, the ratio of activated chemical moiety to antibody or antibody fragment is 2 to 3:1 (mole/mole).

In one embodiment, the antibody or antibody fragment comprises a cysteine residue at a position selected from the group consisting of D70 of the antibody light chain relative to reference sequence SEQ ID NO: 7; E276 of the antibody heavy chain relative to reference sequence SEQ ID NO: 8; and T363 of the antibody heavy chain relative to reference sequence SEQ ID NO: 8.

A conjugation site being "amenable to conjugation" means that the side chain of the amino acid residue at the selected conjugation site will react with the additional functional moiety of interest (or with a linker covalently attached to the additional functional moiety), under the defined chemical conditions, resulting in covalent binding of the additional functional moiety (directly or via the linker) to the side chain as a major reaction product.

Disulfides are covalent bindings of two sulfur atoms which may be present in different (or the same) molecules. In proteins, cysteine residues may be linked via a disulfide bond also called a cystine.

In order to be an effective target of a conjugation reaction the free cysteine must be in the reduced form. A protein with a free cysteine, may for the same reason, be difficult to produce, and is thus frequently obtained as a mixed disulfide including a small organic moiety. Mixed disulfides are molecules including a di-sulfide, similar to the di-sulfide bond between two cysteine amino acid residues, each included in a polypeptides sequence (which may be the same or not). The small organic moiety is herein referred to as a Cap and the mixed disulfide is thus a protein-S—S-Cap molecule. In the present application the term "mixed disulfides" is used for molecules which comprise a disulfide bond linking two different entities which are not both polypeptides, although the molecules may additionally include "ordinary" disulfides bonds in addition to the mixed disulfide.

In one embodiment the method of the invention includes a step of reduction of a protein-S—S-Cap molecule as the protein subject to conjugation is obtained in the form of a composition of protein-S—S-Cap molecule.

As described above, the Cap is usually derived from a small organic moiety, including at least one sulfur atom that is part of the disulfide bond of the mixed di-sulfide. Such organic moieties can exist as monomers in the reduced form or as dimers in the oxidised form. In the mixed disulfide, —S-Cap is thus the oxidised form of the monomer or half a dimer. In one embodiment the —S-Cap is derived from cysteine/cystine, cysteamine/cystamine (which is a decarboxylated cystine) or glutathione (G-SH)/glutathione disulfide (GS-SG), and the mixed disulfide is thus in an embodiment selected from Protein-S—S-cys, Protein-S—S-cyst or Protein-S—S-G, where cys refers to half of a cystine, cyst refers to half of cystamine and G refers to half of glutathione disulfide. In other words, in one embodiment the Cap of protein-S—S-Cap is derived from cysteine, cysteamine or glutathione.

In certain embodiments, the cap is selected from the group consisting of (Cys)

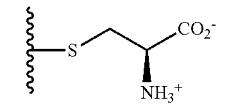

(MNB)

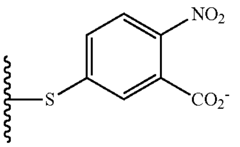

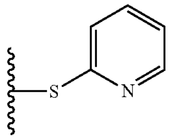

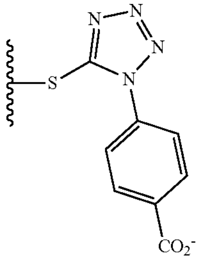

(CA)

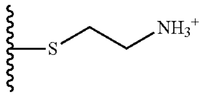

(MES)

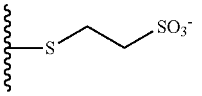

(MPA)

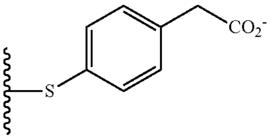

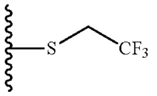

-continued

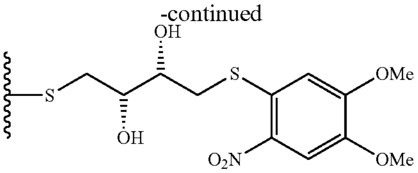

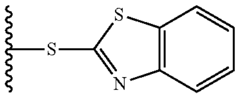

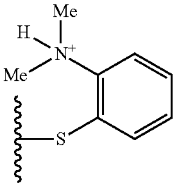

(GS)

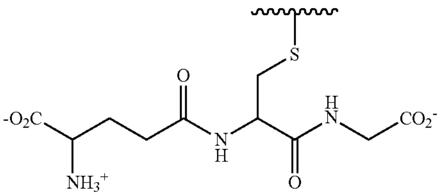

As described above the aim of the reduction is to obtain a molecule with a free reduced cysteine (—SH) that is reactive in a conjugation reaction.

In one embodiment the mixed disulfide is a protein-S—S-Cap molecule wherein the protein-S is derived from a protein comprising a free cysteine.

In order to obtain a protein with a reactive sulfur atom a reducing agent is added to the mixed disulfide composition, and the mixture is incubated to allow the reduction to occur to obtain a protein with a reactive sulfur atom e.g. a reduced protein of the format: protein-S—H. The steps described are a) obtaining a composition of a mixed di-sulfide comprising the protein, b) adding a reducing agent to said protein composition, c) allowing reduction to occur and obtaining a solution comprising a reduced protein (P—SH).

The reducing agent may be chosen between a plurality of available reducing agents and only a few are mentioned herein, knowing that the person skilled in the art will be able to choose from a much larger repertoire of reducing agents.

In one embodiment the reducing agent is a redox buffer selected from the group of gluthathione, gama-glytamylcysteine, cysteinylglycin, cysteine, N-actylcystein, cysteamine and lipamide. In one embodiment a thiol disulfide redox catalyst is included, such as an enzyme, such as a glutaredoxin. In one embodiment the reducing agent is selected from a small molecule reducing agents such as DTT. In one embodiment the reducing agent is a phosphine, such as an aromatic phosphine, such as a triarylphosphine, such as a substituted triarylphosphine, such as tris(2-carboxyethyl) phosphine ("TCEP"), trisodium triphenylphosphine-3,3',3"-trisulfonate (TPPTS) or such as disodium triphenylphosphine-3,3'-disulfonate (TPPDS).

Once the mixed di-sulfide has been reduced a solution comprising a reduced protein (P—SH) has been obtained. Before the subsequent conjugation it may be beneficial to remove the reducing agent and/or the released Cap molecule. In one embodiment, an optional step of removing small molecules, such as molecules with a molecular weight below 10 kDa from the solution comprising the reduced protein (P—SH) may be included. In one embodiment molecules with a molecular weight below 10 kDa are removed from the solution comprising the reduced protein by diafiltration.

In a conjugation reaction a chemical moiety is covalently bonded to the sulfur atom of the free cysteine of the reduced protein (protein-SH). The chemical moiety may be any moiety suitable for conjugation to a protein, such as a property modifying moiety. The property modifying moiety may be a chemical moiety capable of altering one of more features of the protein of interest. In one embodiment the chemical moiety is a property-modifying group, such as a chemical moiety capable of stabilizing the protein, increasing the circulatory half-life or increasing potency. In one embodiment the chemical moiety is a protracting agent. In order for the conjugation to occur effectively, the chemical moiety may be used in an activated form. In the method according to the invention as described herein above, an activated chemical moiety is added to the solution comprising the reduced protein and the conjugation of the chemical moiety to the reduced protein results in preparation of a conjugated protein. Thus, the method according to the invention includes the further steps of: adding an activated chemical moiety to the solution comprising the reduced protein, allowing conjugation reaction to occur and obtaining a preparation of said conjugated protein.

The chemical moiety may be any moiety suitable for conjugation to a protein, such as a property modifying moiety. The property modifying moiety may be a chemical moiety capable of altering one of more features of the protein of interest. In one embodiment, the chemical moiety is a peptide and/or ligand with or without a linker sequence. In one embodiment the chemical moiety is a property-modifying group, such as a chemical moiety capable of stabilizing the protein, increasing the circulatory half-life or increasing potency. In one embodiment the chemical moiety is an albumin binder. In order for the conjugation to occur effectively, the chemical moiety may be used in an activated form. In the method according to the invention as described herein above, an activated chemical moiety is combined with the reduced protein and the conjugation of the chemical moiety to the reduced protein results in preparation of a conjugated protein via a sulfur atom.

The chemical moiety is preferably an activated chemical moiety, which means a moiety which is capable of reacting with the protein-SH forming a protein-S-chemical moiety molecule. Such activated chemical moieties may include soft electrophilic alkylation reagents including a maleimide or haloacetyl groups, which are known in the art.

In one embodiment the activated chemical moiety is a halogenated chemical moiety, such as a halogenated peptide ligand. The halogenated chemical moiety may include Br, I or Cl.

In one embodiment the activated chemical moiety is a halogenated albumin binder (AB-halo).

In order to have an effective reduction of the mixed di-sulfide an excess of the reducing agent in molar concentrations is usually applied. By addition of the reducing agent to the composition of the mixed disulfide a reduction mix is obtained. The amount of reducing agent may be expressed in equivalents of the amount of the mixed di-sulfide, such that in the case where the amount of reducing agent is 1 equivalent of the amount of the mixed di-sulfide, the molar concentrations of the mixed di-sulfide and the reducing agent in the mixture are equal.

In one embodiment the amount of the reducing agent added from about 2 molar equivalents to about 4 molar equivalents of the molar amount of the mixed di-sulfide.

In order to reduce the amount of over-reduction of the antibody or antibody fragment, it is advantageous to reduce the amount required, which as described herein is possible if the process steps are optimized. An effective reduction reaction using lower amounts of the reducing agent requires that remaining reaction conditions are carefully selected as is provided by the present invention.

The reduction of the mixed di-sulfide may, depending on the conditions, take minutes or hours. The skilled person will know that different conditions will result in different efficacy and thus the time and conditions needed to obtain complete or almost complete reduction of the mixed-di-sulfide are described in more detailed in the Examples below.

The reducing agent may be added as concentrate or simply by adding the agent as a solid powder to the mixed di-sulfide composition. The reducing agent is mixed with the mixed di-sulfide composition to initiate reduction. The mix maybe termed the reduction mix.

In order to have a sufficiently effective process the reduction should result in at least an 80% reduction, such as at least 90% reduction of the total amount of mixed disulfide. In such cases the reduction is considered satisfactory when the amount of the mixed di-sulfide is at most 20%, such as at most 10% of the amount of the mixed di-sulfide in the reduction mix. In preferred embodiments a reduction of around 95% of the mixed di-sulfide may be obtained leaving around 5% non-reduced mixed di-sulfide in the solution comprising the reduced protein. In a further embodiment an efficient process leaves at most 2% mixed disulfide within a suitable time.

The reduction may occur during a period of at least 15 minutes, such as at least 30 minutes or such as at least 1 hour. In one embodiment the reduction mix is left for 2-10 hours, such as 3-6 hours or around 3-4 hours after addition of the reducing agent.

In one embodiment the reduction is performed for up to 24 hours, such as for up to 12 hours, such as for up to 8 hours, such as for up to 6 hours such as for up to 4 hours.

The reduction may in one embodiment take place at 1-50° C., such as at room temperature, such as at 18-25° C. In alternative embodiments the reduction may be performed at a colder temperature, such as below 10° C., such as around 4-6° C.

Before proceeding with the conjugation step the reduced protein may be separated from the reduction mix, such as from excess reducing agent and/or the small organic molecule of the mixed di-sulfide e.g. the H—S-Cap of the protein with a capped free cysteine. This optional step may be a step of removing molecules with a low molecular weight, such as molecules with a molecular weight below 10 kDa.

The skilled person will know of various methods for removing small molecular weight compounds, such as by filtration using a suitable membrane. In one embodiment the method comprises a step of buffer exchange (ultrafiltration/diafiltration).

The efficacy of a diafiltration step e.g. the amount of small molecules and excipients which are removed, is related to the filtrate volume generated, relative to the retentate volume. It is also noted that the word "remove" in this context should be read as "reducing the concentration of" as residual amounts of low molecular weight molecules and excipients will usually be present after a diafiltration step (or an alternative process steps) "removing" molecules with a low molecular weight.

Before proceeding with the conjugation step the reduced protein is oxidized in order to decrease the amount of over-reduced antibody or antibody fragment.

In order to have an effective oxidation of the over-reduced antibody or antibody fragment an excess of the oxidizing agent in molar concentrations is usually applied. By addition of the oxidizing agent to the composition of the over-reduced antibody or antibody fragment an oxidized mix is obtained. The amount of oxidizing agent may be expressed in equivalents of the amount of the over-reduced antibody or antibody fragment, such that in the case where the amount of oxidizing agent is 1 equivalent of the amount of the mixed di-sulfide, the molar concentrations of the mixed di-sulfide and the reducing agent in the mixture are equal.

In one embodiment the amount of the oxidizing agent added from about 3 molar equivalents to about 6 molar equivalents of the molar amount of the over-reduced antibody or antibody fragment.

The oxidation of the over-reduced antibody or antibody fragment may, depending on the conditions, take minutes or hours. The skilled person will know that different conditions will result in different efficacy and thus the time and conditions needed to obtain complete or almost complete oxidation of the over-reduced antibody or antibody fragment are described in more detailed in the Examples below.

The oxidizing agent may be added as concentrate or simply by adding the agent as a solid powder to the over-reduced antibody or antibody fragment composition. The oxidizing agent is mixed with the over-reduced antibody or antibody fragment composition to initiate oxidation. The mix may be termed the oxidation mix.

In order to have a sufficiently effective process the oxidation should result in at least an 80% oxidation, such as at least 90% oxidation of the total amount of over-reduced antibody or antibody fragment. In such cases the oxidation is considered satisfactory when the amount of the over-reduced antibody or antibody fragment is at most 20%, such as at most 10% of the amount of the over-reduced antibody or antibody fragment in the oxidation mix. In preferred embodiments an oxidation of around 95% of the over-reduced antibody or antibody fragment may be obtained leaving around 5% over-reduced antibody or antibody fragment in the solution comprising the oxidized protein. In a further embodiment an efficient process leaves at most 2% over-reduced antibody or antibody fragment within a suitable time.

The oxidation may occur during a period of at least 15 minutes, such as at least 30 minutes or such as at least 1 hour. In one embodiment the oxidation mix is left for 2-10 hours, such as 3-6 hours or around 3-4 hours after addition of the oxidation agent.

In one embodiment the oxidation is performed for up to 24 hours, such as for up to 12 hours, such as for up to 8 hours, such as for up to 6 hours such as for up to 4 hours.

The oxidation may in one embodiment take place at 1-50° C., such as at room temperature, such as at 18-25° C. In alternative embodiments the reduction may be performed at a colder temperature, such as below 10° C., such as around 2-8° C. In one embodiment the oxidizing agent is dehydroascorbic acid.

As described above the conjugation is according to the method performed by adding an activated chemical moiety to the solution comprising the reduced protein.

If the prior reduction is not complete the ratio of reduced protein to mixed di-sulfide may prevent a high yielding conjugation reaction. Furthermore the presence of excess reduction agent and released Cap molecules may interfere with the conjugation reaction.

Again the relative ratio of the reactants e.g. the reduced protein and the activated chemical moiety influences the effectiveness of the reaction.

In one embodiment the molar concentration of the activated chemical moiety is at least equal or may be twice the molar concentration of the protein to be conjugated. This may also be expressed in equivalents e.g. at least 10, such as 8, such as 6, such as 4, such as 2 or such as at least one (1) equivalent(s) of the activated chemical moiety relative to the protein to be conjugated may be used. As the activated chemical moiety may be a costly resource it is advantageous to reduce the amount required, which as described herein is possible if the previous steps are optimized. An effective conjugation reaction using reduced amounts of the activated chemical moiety requires that remaining reaction conditions are carefully selected as is provided by the present invention. In one embodiment the amount of activated chemical moiety is at most 8 equivalents of the protein, such as at most 6, such as at most 4, such as at most 3, such as at most 2.5, such as at most 2, such as at most 1.5 equivalents of the protein to be conjugated.

The conjugation of the oxidized protein with the chemical moiety may, depending on the conditions, take minutes or hours. The skilled person will know that different conditions will result in different efficacy and thus the time needed to obtain complete or almost complete conjugation will vary based on the conditions as will be described more detailed herein below. According to the present method the conjugation reaction is considered satisfactory when the amount of the starting material e.g. the reduced protein reached 10%, such as 5% or preferably 2% or less.

The activated chemical moiety may be added as concentrate or simply by adding the agent as a solid powder to the solution comprising the oxidized protein. In one embodiment the activated chemical moiety is dissolved in a suitable solution prior to adding the activated chemical moiety to the solution comprising the oxidized protein. It may also be that the chemical moiety is activated in a solution prior to the conjugation reaction.

The term "half-life extending moiety refers to a pharmaceutically acceptable moiety, domain, or "vehicle" covalently linked or conjugated to the Fc domain and/or a pharmaceutically active moiety, that prevents or mitigates in vivo proteolytic degradation or other activity-diminishing chemical modification of the pharmaceutically active moiety, increases half-life or other pharmacokinetic properties such as but not limited to increasing the rate of absorption, reduces toxicity, improves solubility, increases biological activity and/or target selectivity of the pharmaceutically active moiety with respect to a target of interest, increases manufacturability, and/or reduces immunogenicity of the pharmaceutically active moiety (e.g., a peptide or non-peptide moiety), compared to an unconjugated form of the pharmaceutically active moiety. Polyethylene glycol (PEG) is an example of a useful half-life extending moiety. Other examples of the half-life extending moiety, in accordance with the invention, include a copolymer of ethylene glycol, a copolymer of propylene glycol, a carboxymethylcellulose, a polyvinyl pyrrolidone, a poly-1,3-dioxolane, a poly-1,3,6-trioxane, an ethylene maleic anhydride copolymer, a polyaminoacid (e.g., polylysine), a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group, an immunoglobulin $F_c$ domain (see, e.g., Feige et al., Modified peptides as therapeutic agents, U.S. Pat. No. 6,660,843), an albumin (e.g., human serum albumin; see, e.g., Rosen et al., Albumin fusion proteins, U.S. Pat. No. 6,926,898 and US 2005/0054051; Bridon et al., Protection of endogenous therapeutic peptides from peptidase activity through conjugation to blood components, U.S. Pat. No. 6,887,470), a transthyretin (TTR; see, e.g., Walker et al., Use of transthyretin peptide/protein fusions to increase the serum half-life of pharmacologically active peptides/proteins, US 2003/0195154 A1; 2003/0191056 A1), or a thyroxine-binding globulin (TBG).

Other embodiments of the useful half-life extending moiety, in accordance with the invention, include peptide ligands or small (non-peptide organic) molecule ligands that have binding affinity for a long half-life serum protein under physiological conditions of temperature, pH, and ionic strength. Examples include an albumin-binding peptide or small molecule ligand, a transthyretin-binding peptide or small molecule ligand, a thyroxine-binding globulin-binding peptide or small molecule ligand, an antibody-binding peptide or small molecule ligand, or another peptide or small molecule that has an affinity for a long half-life serum protein. (See, e.g., Blaney et al., Method and compositions for increasing the serum half-life of pharmacologically active agents by binding to transthyretin-selective ligands, U.S. Pat. No. 5,714,142; Sato et al., Serum albumin binding moieties, US 2003/0069395 A1; Jones et al., Pharmaceutical active conjugates, U.S. Pat. No. 6,342,225). A "long half-life serum protein" is one of the hundreds of different proteins dissolved in mammalian blood plasma, including so-called "carrier proteins" (such as albumin, transferrin and haptoglobin), fibrinogen and other blood coagulation factors, complement components, immunoglobulins, enzyme inhibitors, precursors of substances such as angiotensin and bradykinin and many other types of proteins. The invention encompasses the use of any single species of pharmaceutically acceptable half-life extending moiety, such as, but not limited to, those described herein, or the use of a combination of two or more different half-life extending moieties.

Recombinant polypeptide and nucleic acid methods used herein, including in the Examples, are generally those set forth in Sambrook et al., Molecular Cloning: A Laboratory Manual (Cold Spring Harbor Laboratory Press, 1989) or Current Protocols in Molecular Biology (Ausubel et al., eds., Green Publishers Inc. and Wiley and Sons 1994), both of which are incorporated herein by reference for any purpose.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean$\pm$1%.

Following convention, as used herein "a" and "an" mean "one or more" unless specifically indicated otherwise.

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

A "naturally occurring amino acid" is an amino acid that is encoded by the genetic code, as well as those amino acids that are encoded by the genetic code that are modified after synthesis, e.g., hydroxyproline, γ-carboxyglutamate, and O-phosphoserine. An amino acid analog is a compound that has the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but will retain the same basic chemical structure as a naturally occurring amino acid.

An "amino acid mimetic" is a chemical compound that has a structure that is different from the general chemical structure of an amino acid, but that functions in a manner similar to a naturally occurring amino acid. Examples include a methacryloyl or acryloyl derivative of an amide, β-, γ-, δ-imino acids (such as piperidine-4-carboxylic acid) and the like.

A "non-naturally occurring amino acid" is a compound that has the same basic chemical structure as a naturally occurring amino acid, but is not incorporated into a growing polypeptide chain by the translation complex. "Non-naturally occurring amino acid" also includes, but is not limited to, amino acids that occur by modification (e.g., posttranslational modifications) of a naturally encoded amino acid (including but not limited to, the 20 common amino acids)

but are not themselves naturally incorporated into a growing polypeptide chain by the translation complex. A non-limiting lists of examples of non-naturally occurring amino acids that can be inserted into a polypeptide sequence or substituted for a wild-type residue in polypeptide sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl)alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α, β-diaminopropionoic acid (Dpr), a, γ-diaminobutyric acid (Dab), diaminopropionic acid (Dap), cyclohexylalanine (Cha), 4-methyl-phenylalanine (MePhe), β, β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, Ω-methylarginine, 4-Amino-O-Phthalic Acid (4APA), and other similar amino acids, and derivatized forms of any of those specifically listed.

The term "isolated nucleic acid molecule" refers to a single or double-stranded polymer of deoxyribonucleotide or ribonucleotide bases read from the 5' to the 3' end, or an analog thereof, that has been separated from at least about 50 percent of polypeptides, peptides, lipids, carbohydrates, polynucleotides or other materials with which the nucleic acid is naturally found when total nucleic acid is isolated from the source cells. Preferably, an isolated nucleic acid molecule is substantially free from any other contaminating nucleic acid molecules or other molecules that are found in the natural environment of the nucleic acid that would interfere with its use in polypeptide production or its therapeutic, diagnostic, prophylactic or research use.

The term "isolated polypeptide" refers to a polypeptide that has been separated from at least about 50 percent of polypeptides, peptides, lipids, carbohydrates, polynucleotides, or other materials with which the polypeptide is naturally found when isolated from a source cell. Preferably, the isolated polypeptide is substantially free from any other contaminating polypeptides or other contaminants that are found in its natural environment that would interfere with its therapeutic, diagnostic, prophylactic or research use.

A composition of the present invention that includes a drug or peptide linked, attached, or bound, either directly or indirectly through a linker moiety, to another an antibody or antibody fragment is a "conjugate" or "conjugated" molecule.

The term "encoding" refers to a polynucleotide sequence encoding one or more amino acids. The term does not require a start or stop codon.

The terms "identical" and percent "identity," in the context of two or more nucleic acids or polypeptide sequences, refer to two or more sequences or subsequences that are the same. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) SIAM J. Applied Math. 48:1073.

In calculating percent identity, the sequences being compared are aligned in a way that gives the largest match between the sequences. The computer program used to determine percent identity is the GCG program package, which includes GAP (Devereux et al., (1984) Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program are the following:

- Algorithm: Needleman et al., 1970, J. Mol. Biol. 48:443-453;
- Comparison matrix: BLOSUM 62 from Henikoff et al., 1992, supra;
- Gap Penalty: 12 (but with no penalty for end gaps)
- Gap Length Penalty: 4
- Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

An "antigen binding protein" as used herein means any protein that specifically binds a specified target antigen. The term encompasses intact antibodies that comprise at least two full-length heavy chains and two full-length light chains, as well as derivatives, variants, fragments, and mutations thereof. Examples of antibody fragments include Fab, Fab', $F(ab')_2$, and Fv fragments. An antigen binding protein also includes domain antibodies such as nanobodies and scFvs as described further below.

In general, an antigen binding protein is said to "specifically bind" its target antigen when the antigen binding protein exhibits essentially background binding to non-target molecules. An antigen binding protein that specifically binds to a target may, however, cross-react with target antigens from different species. Typically, a antigen binding protein specifically binds to target when the dissociation constant (KD) is $\leq 10^{-7}$ M as measured via a surface plasma resonance technique (e.g., BIACore, GE-Healthcare Uppsala, Sweden) or Kinetic Exclusion Assay (KinExA, Sapidyne, Boise, Id.). An antigen binding protein specifically binds target with "high affinity" when the KD is $\leq 5\times10^{-9}$M, and with "very high affinity" when the KD is $\leq 5\times10^{10}$ M, as measured using methods described.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs") of an immunoglobulin, single-chain immunoglobulin, or camelid antibody. Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

A "recombinant protein" is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" as such is a species of an antigen binding protein. An intact antibody generally will comprise at least two full-length heavy chains and two full-length light chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies.

The term "light chain" as used with respect to an antibody or fragments thereof includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" as used with respect to an antibody or fragment thereof includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope.

These biologically active fragments may be produced by recombinant DNA techniques, or may be produced by enzymatic or chemical cleavage of antigen binding proteins, including intact antibodies Immunologically functional immunoglobulin fragments include, but are not limited to, Fab, Fab', and F(abD2 fragments.

In another embodiment, Fvs, domain antibodies and scFvs, and may be derived from an antibody of the present invention.

It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

A "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

An "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')2 molecule.

An "F(ab')2 fragment" contains two light chains and two heavy chains containing a portion of the constant region between the CH1 and CH2 domains, such that an interchain disulfide bond is formed between the two heavy chains A F(ab')2 fragment thus is composed of two Fab' fragments that are held together by a disulfide bond between the two heavy chains.

The "Fv region" comprises the variable regions from both the heavy and light chains, but lacks the constant regions.

"Single chain antibodies" or "scFvs" are Fv molecules in which the heavy and light chain variable regions have been connected by a flexible linker to form a single polypeptide chain, which forms an antigen-binding region. scFvs are discussed in detail in International Patent Application Publication No. WO 88/01649 and U.S. Pat. Nos. 4,946,778 and 5,260,203, the disclosures of which are incorporated by reference.

A "domain antibody" or "single chain immunoglobulin" is an immunologically functional immunoglobulin fragment containing only the variable region of a heavy chain or the variable region of a light chain Examples of domain antibodies include Nanobodies®. In some instances, two or more VH regions are covalently joined with a peptide linker to create a bivalent domain antibody. The two VH regions of a bivalent domain antibody may target the same or different antigens.

A "bivalent antigen binding protein" or "bivalent antibody" comprises two antigen binding regions. In some instances, the two binding regions have the same antigen specificities. Bivalent antigen binding proteins and bivalent antibodies may be bispecific, see, infra.

A multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which may reside on the same or different protein targets.

The term "compete" when used in the context of antigen binding proteins (e.g., antibodies) means competition between antigen binding proteins is determined by an assay in which the antigen binding protein (e.g., antibody or immunologically functional fragment thereof) under test prevents or inhibits specific binding of a reference antigen binding protein to a common antigen. Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instances, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody. An epitope can be contiguous or non-contiguous (discontinuous) (e.g., in a polypeptide, amino acid residues that are not contiguous to one another in the polypeptide sequence but that within in context of the molecule are bound by the antigen binding protein). A conformational epitope is an epitope that exists within the conformation of an active protein but is not present in a denatured protein. In certain embodiments, epitopes may be mimetic in that they comprise a three-dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three-dimensional structural characteristics, and/or specific charge characteristics. Generally, antigen binding proteins specific for a particular target antigen will preferentially recognize an epitope on the target antigen in a complex mixture of proteins and/or macromolecules.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, 96%, 97%, 98%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term “oligonucleotide” means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

An “isolated nucleic acid molecule” means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that “a nucleic acid molecule comprising” a particular nucleotide sequence does not encompass intact chromosomes. Isolated nucleic acid molecules “comprising” specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as “upstream sequences;” sequence regions on the DNA strand having the same sequence as the RNA transcript that are 3' to the 3' end of the RNA transcript are referred to as “downstream sequences.”

The term “control sequence” refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequences. “Control sequences” can include leader sequences and/or fusion partner sequences.

The term “vector” means any molecule or entity (e.g., nucleic acid, plasmid, bacteriophage or virus) used to transfer protein coding information into a host cell.

The term “expression vector” or “expression construct” refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, “operably linked” means that the components to which the term is applied are in a relationship that allows them to carry out their inherent functions under suitable conditions. For example, a control sequence in a vector that is “operably linked” to a protein coding sequence is ligated thereto so that expression of the protein coding sequence is achieved under conditions compatible with the transcriptional activity of the control sequences.

The term “host cell” means a cell that has been transformed with a nucleic acid sequence and thereby expresses a gene of interest. The term includes the progeny of the parent cell, whether or not the progeny is identical in morphology or in genetic make-up to the original parent cell, so long as the gene of interest is present.

The terms “polypeptide” or “protein” are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms “polypeptide” and “protein” specifically encompass antigen binding proteins, antibodies, or sequences that have deletions from, additions to, and/or substitutions of one or more amino acids of an antigen-binding protein. The term “polypeptide fragment” refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains.

The term “isolated protein” means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an “isolated protein” constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A “variant” of a polypeptide (e.g., an antigen binding protein such as an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein such as an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

A "subject" or "patient" as used herein can be any mammal. In a typical embodiment, the subject or patient is a human.

A "conservative amino acid substitution" can involve a substitution of a native amino acid residue (i.e., a residue found in a given position of the wild-type polypeptide sequence) with a nonnative residue (i.e., a residue that is not found in a given position of the wild-type polypeptide sequence) such that there is little or no effect on the polarity or charge of the amino acid residue at that position. Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into classes based on common side chain properties:

(1) hydrophobic: norleucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Additional groups of amino acids can also be formulated using the principles described in, e.g., Creighton (1984) PROTEINS: STRUCTURE AND MOLECULAR PROPERTIES (2d Ed. 1993), W.H. Freeman and Company. In some instances it can be useful to further characterize substitutions based on two or more of such features (e.g., substitution with a "small polar" residue, such as a Thr residue, can represent a highly conservative substitution in an appropriate context).

Conservative substitutions can involve the exchange of a member of one of these classes for another member of the same class. Non-conservative substitutions can involve the exchange of a member of one of these classes for a member from another class.

Synthetic, rare, or modified amino acid residues having known similar physiochemical properties to those of an above-described grouping can be used as a "conservative" substitute for a particular amino acid residue in a sequence. For example, a D-Arg residue may serve as a substitute for a typical L-Arg residue. It also can be the case that a particular substitution can be described in terms of two or more of the above described classes (e.g., a substitution with a small and hydrophobic residue means substituting one amino acid with a residue(s) that is found in both of the above-described classes or other synthetic, rare, or modified residues that are known in the art to have similar physiochemical properties to such residues meeting both definitions).

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a protein in prokaryotic (e.g., *E. coli*) or eukaryotic cells (e.g., insect cells, using baculovirus expression vectors, yeast cells, or mammalian cells). In one embodiment the host cell is a mammalian, non-human host cell. Representative host cells include those hosts typically used for cloning and expression, including *Escherichia coli* strains TOP10F', TOP10, DH10B, DH5a, HB101, W3110, BL21(DE3) and BL21 (DE3)pLysS, BLUESCRIPT (Stratagene), mammalian cell lines CHO, CHO-K1, HEK293, 293-EBNA pIN vectors (Van Heeke & Schuster, J. Biol. Chem. 264: 5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

In various embodiments, the vectors comprise an operably linked nucleotide sequence which regulates the expression of a target polypeptide. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, CAG promoter), effective poly (A) termination sequences, an origin of replication for plasmid product in *E. coli*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a target polypeptide which is operatively linked to a tissue specific promoter which promotes expression of the sequence in a metabolically-relevant tissue, such as liver or pancreatic tissue is provided.

In another aspect of the instant disclosure, host cells comprising the nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments cells comprising a non-integrated nucleic acid, such as a plasmid, cosmid, phagemid, or linear expression element, which comprises a sequence coding for expression of a target polypeptide, are provided.

A vector comprising a nucleic acid sequence encoding a target polypeptide provided herein can be introduced into a host cell by transformation or by transfection. Methods of transforming a cell with an expression vector are well known.

A target-encoding nucleic acid can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

A target polypeptide expressed as described herein can be isolated using standard protein purification methods. A target polypeptide can be isolated from a cell in which is it naturally expressed or it can be isolated from a cell that has been engineered to express target polypeptide, for example a cell that does not naturally express target polypeptide.

Protein purification methods that can be employed to isolate a target polypeptide, as well as associated materials and reagents, are known in the art. Additional purification methods that may be useful for isolating a target polypeptide can be found in references such as Bootcov MR, 1997, Proc. Natl. Acad. Sci. USA 94:11514-9, Fairlie WD, 2000, Gene 254: 67-76.

The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) are achieved. Certain antigen binding proteins described herein are antibodies or are derived from antibodies. In other antigen binding proteins, the CDR sequences are embedded in a different type of protein scaffold.

In general the antigen binding proteins that are provided typically comprise one or more CDRs as described herein (e.g., 1, 2, 3, 4, 5 or 6). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In certain embodiments, the polypeptide structure of the antigen binding proteins is an antibody or is derived from an antibody. Accordingly, examples of certain antigen binding proteins that are provided include, but are not limited to, monoclonal antibodies, bispecific antibodies, minibodies, domain antibodies such as Nanobodies®, synthetic antibodies (sometimes referred to herein as "antibody mimetics"), chimeric antibodies, humanized antibodies, human antibodies, antibody fusions, and portions or fragments of each, respectively. In some instances, the antigen binding protein is an immunological fragment of a complete antibody (e.g., a Fab, a Fab', a F(ab')2). In other instances the antigen binding protein is a scFv that uses CDRs from an antibody of the present invention.

In another aspect, an antigen-binding protein is provided having a half-life of at least one day in vitro or in vivo (e.g., when administered to a human subject). In one embodiment, the antigen binding protein has a half-life of at least three days. In various other embodiments, the antigen binding protein has a half-life of 4, 5, 6, 7, 8, 9, 10, 15, 20, 25, 30, 40, 50, or 60 days or longer. In another embodiment, the antigen binding protein is derivatized or modified such that it has a longer half-life as compared to the underivatized or unmodified antibody. In another embodiment, the antigen binding protein contains point mutations to increase serum half-life. Further details regarding such mutant and derivatized forms are provided below.

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as CH1, CH2 and CH3. The antibodies that are provided can have any of these isotypes and subtypes. In certain embodiments, the antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g. Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

For the antibodies provided herein, the variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the antigen. From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342:878-883.

The present invention relates to a composition comprising an antigen binding protein having at least one internal conjugation site. The conjugation site must be amenable to conjugation of an additional functional moiety (e.g., a drug, ligand, or peptide) by a defined conjugation chemistry through the side chain of an amino acid residue at the conjugation site. Achieving highly selective, site-specific conjugation to the antigen binding protein, in accordance with the present invention, requires consideration of a diverse variety of design criteria. First, a preferred conjugation or coupling chemistry must be defined or predetermined. Functional moieties can be conjugated or coupled to the selected conjugation site of the antigen binding protein through an assortment of different conjugation chemistries known in the art. For example, a maleimide-activated conjugation partner targeting an accessible cysteine thiol on the antigen binding protein is one embodiment, but numerous conjugation or coupling chemistries targeting the side chains of either canonical or non-canonical, e.g., unnatural amino acids in the antigen binding protein sequence, can be employed in accordance with the present invention.

Chemistries for the chemoselective conjugation include: copper(I)-catalyzed azide-alkyne [3+2] dipolar cycloadditions, Staudinger ligation, other acyl transfers processes (S→N; X→N), oximations, hydrazone bonding formation and other suitable organic chemistry reactions such as cross-couplings using water-soluble palladium catalysts. (E.g., Bong et al., Chemoselective Pd(0)-catalyzed peptide coupling in water, Organic Letters 3(16):2509-11 (2001); Dibowski et al., Bioconjugation of peptides by palladium-catalyzed C—C cross-coupling in water, Angew. Chem. Int. Ed. 37(4):476-78 (1998); DeVasher et al., Aqueous-phase, palladium-catalyzed cross-coupling of aryl bromides under mild conditions, using water-soluble, sterically demanding alkylphosphines, J. Org. Chem. 69:7919-27 (2004); Shaugnessy et al., J. Org. Chem, 2003, 68, 6767-6774; Prescher, J A and Bertozzi C R, Chemistry in living system, Nature Chemical Biology 1(1); 13-21 (2005)).

As mentioned above, the conjugation (or covalent binding) to the antigen binding protein is through the side chain of an amino acid residue at the conjugation site, for example, but not limited to, a cysteinyl residue. The amino acid residue, for example, a cysteinyl residue, at the internal conjugation site that is selected can be one that occupies the same amino acid residue position in a native Fc domain sequence, or the amino acid residue can be engineered into the Fc domain sequence by substitution or insertion.

The selection of the placement of the conjugation site in the overall antigen binding protein is another important facet of selecting an internal conjugation site in accordance with the present invention. Any of the exposed amino acid residues on the antigen binding protein can be potentially useful conjugation sites and can be mutated to cysteine or some other reactive amino acid for site-selective coupling, if not already present at the selected conjugation site of the antigen binding protein sequence. However, this approach does not take into account potential steric constraints that may perturb the activity of the conjugated partner or limit the reactivity of the engineered mutation.

In one embodiment, the antigen binding protein is an antibody or functional fragment thereof. In one embodiment, the antibody or functional fragment thereof comprises a cysteine or non-canonical amino acid amino acid substitution at one or more conjugation site(s) selected from the group consisting of D70 of the antibody light chain relative to reference sequence SEQ ID NO: 7; E276 of the antibody heavy chain relative to reference sequence SEQ ID NO: 8; and T363 of the antibody heavy chain relative to reference sequence SEQ ID NO: 8. For sake of clarity, "D70 of the antibody light chain relative to reference sequence SEQ ID NO: 7" is the same substitution site as AHo position D88 of the light chain of antibody 5G12.006 and Kabat position D70 of the light chain of antibody 5G12.006; "E276 of the antibody heavy chain relative to reference sequence SEQ ID NO: 8" is the same substitution site as AHo position E384 of the heavy chain of antibody 5G12.006 and Kabat position E285 of the heavy chain of antibody 5G12.006; and "T363 of the antibody heavy chain relative to reference sequence SEQ ID NO: 8" is the same substitution site as AHo position T487 of the heavy chain of antibody 5G12.006 and Kabat position T382 of the heavy chain of antibody 5G12.006.

TABLE 1

| | | Amino acid SEQ ID NOs. | | | | | | | | | |
|---|---|---|---|---|---|---|---|---|---|---|---|
| Identifier | Construct | VL | VH | LC | HC | CDR L1 | CDR L2 | CDR L3 | CDR H1 | CDR H2 | CDR H3 |
| iPS: 336067 | 5G12.006 | 3 | 4 | 7 | 8 | 12 | 13 | 14 | 18 | 19 | 20 |

TABLE 2

| Nucleic acid SEQ ID NOs. | | | | | | | | | | | | |
|---|---|---|---|---|---|---|---|---|---|---|---|---|
| Identifier | Construct | VL | VH | LC | HC | CDR L1 | CDR L2 | CDR L3 | CDR H1 | CDR H2 | CDR H3 |
| iPS: 336067 | 5G12.006 | 1 | 2 | 5 | 6 | 9 | 10 | 11 | 15 | 16 | 17 |

TABLE 3

Variable Light and Variable Heavy Regions: Nucleic Acid ("NA") and Amino Acid ("AA") Sequences

| iPS # | Ab | Type | VL | VH |
|---|---|---|---|---|
| iPS:336067 | 5G12.006 | NA | GACATCCAGCTGACCCAGTCTCC ATCCTCCCTGTCTGCATCTGTAGG AGACAGAGTCACTATCACTTGCC GGGCAAGTCAGACCATTAGCAGG TTTTTAAATTGGTATCAGCAGAA ACCTGGGAAAGCCCCTGAGCTCC TGATCTATGTTGCATCCAGTTTGC AAAGTGGGGTCCCATCAAGATTC AGTGGCAGTGGTTCTGGGACAGA TTTCACTCTCACCATCAGCAGTCT GCAACCTGAAGATTTTGCAACTT ACTACTGTCAACAGAGTTACAGT ACCCTGATCAGTTTTGGCCAGGG GACCAAGCTGGAGATCACACGA SEQ ID NO: 1 | CAGGTGCAGTTGGTGGAGTCTGG GGGAGGCGTGGTCCAGCCTGGGA GGTCCCTGAGACTCTCCTGTACAG CGTCTGGATTCACCTTCAGTAGCT ATGGCATACACTGGGTCCGCCAG GCTCCAGGCAAGGGGCTGGAGTG GGTGGCAGTTATATGGTATGATG GAAGTAATAAGTTCCATGCAGAC TCCGTGAAGGGCCGATTCACCAT CTCCAGAGACAATTCCAAGAACA CGCTGTATCTGCAAATGAACAGC CTGAGAGCCGAGGACTCGGCTAT GTACTTCTGTGCGAGAGGAAAAG TGGCTGGTATGCCTGAAGCTTTTG AAATCTGGGGCCAAGGGACAAAG GTCACCGTCTCTTCA SEQ ID NO: 2 |
| | | AA | DIQLTQSPSSLSASVGDRVTITCRAS QTISRFLNWYQQKPGKAPELLIYV ASSLQSGVPSRFSGSGSGTDFTLTIS SLQPEDFATYYCQQSYSTLISFGQG TKLEITR SEQ ID NO: 3 | QVQLVESGGGVVQPGRSLRLSCTA SGFTFSSYGIHWVRQAPGKGLEWV AVIWYDGSNKFHADSVKGRFTISR DNSKNTLYLQMNSLRAEDSAMYF CARGKVAGMPEAFEIWGQGTKVT VSS SEQ ID NO: 4 |

TABLE 4A

CDRL1, CDRL2, and CDRL3 Nucleic Acid ("NA") and Amino Acid ("AA") Sequences

| iPS# | Ab | Type | CDRL1 | CDRL2 | CDRL3 |
|---|---|---|---|---|---|
| iPS:336067 | 5G12.006 | NA | CGGGCAAGTCAGAC CATTAGCAGGTTTTT AAAT SEQ ID NO: 9 | GTTGCATCCAGTTTG CAAAGT SEQ ID NO: 10 | CAACAGAGTTACAG TACCCTGATCAGT SEQ ID NO: 11 |
| | | AA | RASQTISRFLN SEQ ID NO: 12 | VASSLQS SEQ ID NO: 13 | QQSYSTLIS SEQ ID NO: 14 |

TABLE 4B

CDRH1, CDRH2, and CDRH3 Nucleotide and Amino Acid Sequences

| iPS# | Ab | Type | CDRL1 | CDRL2 | CDRL3 |
|---|---|---|---|---|---|
| iPS:336067 | 5G12.006 | NA | AGCTATGGCATACA C SEQ ID NO: 15 | GTTATATGGTATGAT GGAAGTAATAAGTTC CATGCAGACTCCGTG AAGGGC SEQ ID NO: 16 | GGAAAAGTGGCTGG TATGCCTGAAGCTTT TGAAATC SEQ ID NO: 17 |

TABLE 4B-continued

| CDRH1, CDRH2, and CDRH3 Nucleotide and Amino Acid Sequences | | | | | |
|---|---|---|---|---|---|
| iPS# | Ab | Type | CDRL1 | CDRL2 | CDRL3 |
| | | AA | SYGIH SEQ ID NO: 18 | VIWYDGSNKFHADSV KG SEQ ID NO: 19 | GKVAGMPEAFEI SEQ ID NO: 20 |

TABLE 5

| Light and Heavy Chain Nucleic Acid ("NA") and Amino Acid ("AA") Sequences | | | | |
|---|---|---|---|---|
| iPS# | Ab | Type | LC | HC |
| iPS:336067 | 5G12.006 | NA | GACATCCAGCTGACCCAGTCTCC ATCCTCCCTGTCTGCATCTGTAG GAGACAGAGTCACTATCACTTGC CGGGCAAGTCAGACCATTAGCA GGTTTTTAAATTGGTATCAGCAG AAACCTGGGAAAGCCCCTGAGCT CCTGATCTATGTTGCATCCAGTTT GCAAAGTGGGGTCCCATCAAGAT TCAGTGGCAGTGGTTCTGGGACA GATTTCACTCTCACCATCAGCAG TCTGCAACCTGAAGATTTTGCAA CTTACTACTGTCAACAGAGTTAC AGTACCCTGATCAGTTTTGGCCA GGGGACCAAGCTGGAGATCACA CGAACGGTGGCTGCACCATCTGT CTTCATCTTCCCGCCATCTGATG AGCAGTTGAAATCTGGAACTGCC TCTGTTGTGTGCCTGCTGAATAA CTTCTATCCCAGAGAGGCCAAAG TACAGTGGAAGGTGGATAACGC CCTCCAATCGGGTAACTCCCAGG AGAGTGTCACAGAGCAGGACAG CAAGGACAGCACCTACAGCCTCA GCAGCACCCTGACGCTGAGCAA AGCAGACTACGAGAAACACAAA GTCTACGCCTGCGAAGTCACCCA TCAGGGCCTGAGCTCGCCCGTCA CAAAGAGCTTCAACAGGGGAGA GTGT SEQ ID NO: 5 | CAGGTGCAGTTGGTGGAGTCTGG GGGAGGCGTGGTCCAGCCTGGG AGGTCCCTGAGACTCTCCTGTAC AGCGTCTGGATTCACCTTCAGTA GCTATGGCATACACTGGGTCCGC CAGGCTCCAGGCAAGGGGCTGG AGTGGGTGGCAGTTATATGGTAT GATGGAAGTAATAAGTTCCATGC AGACTCCGTGAAGGGCCGATTC ACCATCTCCAGAGACAATTCCAA GAACACGCTGTATCTGCAAATGA ACAGCCTGAGAGCCGAGGACTC GGCTATGTACTTCTGTGCGAGAG GAAAAGTGGCTGGTATGCCTGA AGCTTTTGAAATCTGGGGCCAAG GGACAAAGGTCACCGTCTCTTCA GCCTCCACCAAGGGCCCATCGGT CTTCCCCCTGGCACCCTCCTCCA AGAGCACCTCTGGGGGCACAGC GGCCCTGGGCTGCCTGGTCAAGG ACTACTTCCCCGAACCGGTGACG GTGTCGTGGAACTCAGGCGCCCT GACCAGCGGCGTGCACACCTTCC CGGCTGTCCTACAGTCCTCAGGA CTCTACTCCCTCAGCAGCGTGGT GACCGTGCCCTCCAGCAGCTTGG GCACCCAGACCTACATCTGCAAC GTGAATCACAAGCCCAGCAACA CCAAGGTGGACAAGAAAGTTGA GCCCAAATCTTGTGACAAAACTC ACACATGCCCACCGTGCCCAGCA CCTGAACTCCTGGGGGGACCGTC AGTCTTCCTCTTCCCCCCAAAAC CCAAGGACACCCTCATGATCTCC CGGACCCCTGAGGTCACATGCGT GGTGGTGGACGTGAGCCACGAA GACCCTGAGGTCAAGTTCAACTG GTACGTGGACGGCGTGGAGGTG CATAATGCCAAGACAAAGCCGT GTGAGGAGCAGTACGGCAGCAC GTACCGTTGTGTCAGCGTCCTCA CCGTCCTGCACCAGGACTGGCTG AATGGCAAGGAGTACAAGTGCA AGGTCTCCAACAAAGCCCTCCCA GCCCCCATCGAGAAAACCATCTC CAAAGCCAAAGGGCAGCCCCGA GAACCACAGGTGTACACCCTGCC CCCATCCCGGGAGGAGATGACC AAGAACCAGGTCAGCCTGACCT GCCTGGTCAAAGGCTTCTATCCC AGCGACATCGCCGTGGAGTGGG AGAGCAATGGGCAGCCGGAGAA CAACTACAAGACCACGCCTCCCG TGCTGGACTCCGACGGCTCCTTC TTCCTCTATAGCAAGCTCACCGT GGACAAGAGCAGGTGGCAGCAG GGGAACGTCTTCTCATGCTCCGT GATGCATGAGGCTCTGCACAACC ACTACACGCAGAAGAGCCTCTCC CTGTCTCCGGGTAAA SEQ ID NO: 6 |

TABLE 5-continued

Light and Heavy Chain Nucleic Acid ("NA") and Amino Acid ("AA") Sequences

| iPS# | Ab | Type | LC | HC |
|---|---|---|---|---|
| | | AA | DIQLTQSPSSLSASVGDRVTITCRA SQTISRFLNWYQQKPGKAPELLIY VASSLQSGVPSRFSGSGSGTDFTLT AAISSLQPEDFATYYCQQSYSTLISFG QGTKLEITRTVAAPSVFIFPPSDEQ LKSGTASVVCLLNNFYPREAKVQ WKVDNALQSGNSQESVTEQDSKD STYSLSSTLTLSKADYEKHKVYAC EVTHQGLSSPVTKSFNRGEC SEQ ID NO: 7 | QVQLVESGGGVVQPGRSLRLSCT ASGFTFSSYGIHWVRQAPGKGLE WVAVIWYDGSNKFHADSVKGRF TISRDNSKNTLYLQMNSLRAEDSA MYFCARGKVAGMPEAFEIWGQG TKVTVSSASTKGPSVFPLAPSSKST SGGTAALGCLVKDYFPEPVTVSW NSGALTSGVHTFPAVLQSSGLYSL SSVVTVPSSSLGTQTYICNVNHKP SNTKVDKKVEPKSCDKTHTCPPCP APELLGGPSVFLFPPKPKDTLMISR TPEVTCVVVDVSHEDPEVKFNWY VDGVEVHNAKTKPCEEQYGSTYR CVSVLTVLHQDWLNGKEYKCKV SNKALPAPIEKTISKAKGQPREPQV YTLPPSREEMTKNQVSLTCLVKGF YPSDIAVEWESNGQPENNYKTTPP VLDSDGSFFLYSKLTVDKSRWQQ GNVFSCSVMHEALHNHYTQKSLS LSPGK SEQ ID NO: 8 |

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in TABLES 4A and 4B. These CDRs use the system described by Kabat et al. as noted above.

The structure and properties of CDRs within a naturally occurring antibody has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

The antigen binding proteins that are provided include monoclonal antibodies. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 41, Sp210-Ag14, FO, NSO/U, MPC-11, MPC11-X45-GTG 1.7 and 5194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e g, a transgenic animal having human immunoglobulin sequences) with an immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a target polypeptide. Such hybridoma cell lines, and monoclonal antibodies produced by them, are aspects of the present application.

Monoclonal antibodies secreted by a hybridoma cell line can be purified using any technique known in the art. Hybridomas or mAbs may be further screened to identify mAbs with particular properties.

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855, which are hereby incorporated by reference. CDR grafting is described, for example, in U.S. Pat. Nos. 6,180,370, 5,693,762, 5,693,761, 5,585,089, and 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, *Nature* 321:522-525; Riechmann et al., 1988, *Nature* 332:323-27; Verhoeyen et al., 1988, *Science* 239: 1534-1536).

In one aspect, the CDRs of the light and heavy chain variable regions of the antibodies provided herein are grafted to framework regions (FRs) from antibodies from the same, or a different, phylogenetic species. For example, the CDRs of the heavy and light chain variable regions $V_H1$, $V_H2$, $V_H3$, $V_H4$, $V_H5$, $V_H6$, $V_H7$, $V_H8$, $V_H9$, $V_H10$, $V_H11$, $V_H12$ and/or $V_L1$, and $V_L2$ can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of antibodies are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully human antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. NY Acad. Sci.* 764:536-546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immunol.* 152:2912-2920; Lonberg et cll., 1994, *Nature* 368:856-859; Lonberg, 1994, *Handbook of Exp. Pharmacology* 113:49-101; Taylor et al., 1994, *International Immunology* 6:579-591; Lonberg and Huszar, 1995, *Intern. Rev. Immunol.* 13:65-93; Harding and Lonberg, 1995, *Ann. N.Y Acad. Sci.* 764:536-546; Fishwild et al., 1996, *Nature Biotechnology* 14:845-851; the foregoing references are hereby incorporated by reference in their entirety for all purposes. See, further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate human monoclonal antibodies against a target antigen. Further details regarding the production of human antibodies using transgenic mice are provided below.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference).

Derivatives of the antigen binding proteins that are described herein are also provided. The derivatized antigen binding proteins can comprise any molecule or substance that imparts a desired property to the antibody or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e g., human serum albumin) and polyethylene glycol (PEG). Albumin-linked and PEGylated derivatives of antigen binding proteins can be prepared using techniques well known in the art. Certain antigen binding proteins include a pegylated single chain polypeptide as described herein. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of antigen binding proteins with other proteins or polypeptides, such as by expression of recombinant fusion proteins comprising heterologous polypeptides fused to the N-terminus or C-terminus of an antigen binding protein. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of the antigen binding protein (e.g., poly-His). An antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

In some embodiments, the antigen binding protein comprises one or more labels. The term "labeling group" or "label" means any detectable label. Examples of suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a Renilla, Ptilosarcus, or Aequorea species of GFP (Chalfie et al., 1994, *Science* 263:802-805), EGFP (Clontech Labs., Inc., Genbank Accession Number U55762), blue fluorescent protein (BFP, Quantum Biotechnologies, Inc., Quebec, Canada; Stauber, 1998, Biotechniques 24:462-471; Heim et al., 1996, Curr. Biol. 6:178-182), enhanced yellow fluorescent protein (EYFP, Clontech Labs., Inc.), luciferase (Ichiki et al., 1993, J. Immunol. 150:5408-5417), β galactosidase (Nolan et al., 1988, Proc. Natl. Acad. Sci. U.S.A. 85:2603-2607) and Renilla (WO92/15673, WO95/07463, WO98/14605, WO98/26277, WO99/49019, U.S. Pat. No. 5,292,658, No. 5418155, No. 5683888, No. 5741668, No. 5777079, No. 5804387, No. 5874304, No. 5876995, No. 5925558).

Nucleic acids that encode for the antigen binding proteins described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids). Any variable region provided herein may be attached to these constant regions to form complete heavy and light chain sequences. However, it should be understood that these constant regions sequences are provided as specific examples only. In some embodiments, the variable region sequences are joined to other constant region sequences that are known in the art.

Nucleic acids encoding certain antigen binding proteins, or portions thereof (e.g., full length antibody, heavy or light chain, variable domain, or CDRH1, CDRH2, CDRH3, CDRL1, CDRL2, or CDRL3) may be isolated from B-cells of mice that have been immunized with antigen. The nucleic acid may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding proteins.

An aspect further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y., supra; and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody. In one embodiment, a nucleic acid encoding any antigen binding protein described herein can be mutated to alter the amino acid sequence using molecular biology techniques that are well-established in the art.

Another aspect provides nucleic acid molecules that are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, *Trends Biochem. Sci.* 11:287, Maniatis et al., 1987, *Science* 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Expression systems and constructs in the form of plasmids, expression vectors, transcription or expression cassettes that comprise at least one polynucleotide as described above are also provided herein, as well host cells comprising such expression systems or constructs.

The antigen binding proteins provided herein may be prepared by any of a number of conventional techniques. For example, antigen binding proteins may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; 4,912,040; 4,740,461; 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of an antigen binding protein. These nucleic acid sequences are inserted into an appropriate expression vector using standard ligation techniques. In one embodiment, the heavy or light chain constant region is appended to the C-terminus of the heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, Biotech. Biotechnol. Bioeng. 84:439-44, which is hereby incorporated by reference. Additional suitable expression vectors are discussed, for example, in Methods Enzymol., vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the antigen binding protein coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the antigen binding protein from the host cell. Affinity purification can be accomplished, for example, by column chromatography using antibodies against the tag as an affinity matrix. Optionally, the tag can subsequently be removed from the purified antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds target polypeptide. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding the antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising an antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

An enhancer sequence may be inserted into the vector to increase transcription of DNA encoding light chain or heavy chain comprising an antigen binding protein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

In one embodiment the leader sequence comprises SEQ ID NO: 21 (MDMRVPAQLL GLLLLWLRGA RC) which is encoded by SEQ ID NO: 22 (atggacatga gagtgcctgc acagctgctg ggcctgctgc tgctgtggct gagaggcgcc agatgc). In another embodiment the leader sequence comprises SEQ ID NO: 23 (MAWALLLLTL LTQGTGSWA) which is encoded by SEQ ID NO: 24 (atggcctggg ctctgctgct cctcaccctc ctcactcagg gcacagggtc ctgggcc).

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an antigen binding sequence has been inserted into the proper site of the vector, the completed vector may be inserted into a suitable host cell for amplification and/or polypeptide expression. The transformation of an expression vector for an antigen-binding protein into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In another embodiment, a cell line from the B cell lineage that does not make its own antibody but has a capacity to make and secrete a heterologous antibody can be selected.

A "linker moiety" as used herein refers to a biologically acceptable peptidyl or non-peptidyl organic group that is covalently bound to an amino acid residue of a toxin peptide analog or other polypeptide chain (e.g., an immunoglobulin HC or LC or immunoglobulin Fc domain) contained in the inventive composition, which linker moiety covalently joins or conjugates the toxin peptide analog or other polypeptide chain to another peptide or polypeptide chain in the composition, or to a half-life extending moiety. In some embodiments of the composition, a half-life extending moiety, as described herein, is conjugated, i.e., covalently bound directly to an amino acid residue of the toxin peptide analog itself, or optionally, to a peptidyl or non-peptidyl linker moiety (including but not limited to aromatic or aryl linkers) that is covalently bound to an amino acid residue of the toxin peptide analog. The presence of any linker moiety is optional. When present, its chemical structure is not critical, since it serves primarily as a spacer to position, join, connect, or optimize presentation or position of one functional moiety in relation to one or more other functional moieties of a molecule of the inventive composition. The presence of a linker moiety can be useful in optimizing pharmacological activity of some embodiments of the inventive composition. The linker, if present, can be made up of amino acids linked together by peptide bonds. The linker moiety, if present, can be independently the same or different from any other linker, or linkers, that may be present in the inventive composition. In some embodiments the linker can be a multivalent linker that facilitates multivalent display of toxin peptide analogs of the present invention; multivalent display of such biologically active compounds can increase binding affinity and/or potency through avidity. The in vivo properties of a therapeutic can be altered (i.e., specific targeting, half-life extension, distribution profile, etc.) through conjugation to a polymer or protein.

Peptidyl linkers. As stated above, the linker moiety, if present (whether within the primary amino acid sequence of the toxin peptide analog, or as a linker for attaching a half-life extending moiety to the toxin peptide analog), can be "peptidyl" in nature (i.e., made up of amino acids linked together by peptide bonds) and made up in length, preferably, of from 1 up to about 40 amino acid residues, more preferably, of from 1 up to about 20 amino acid residues, and most preferably of from 1 to about 10 amino acid residues. Preferably, but not necessarily, the amino acid residues in the linker are from among the twenty canonical amino acids, more preferably, cysteine, glycine, alanine, proline, asparagine, glutamine, and/or serine. Even more preferably, a peptidyl linker is made up of a majority of amino acids that are sterically unhindered, such as glycine, serine, and alanine linked by a peptide bond. It is also desirable that, if present, a peptidyl linker be selected that avoids rapid proteolytic turnover in circulation in vivo. Some of these amino acids may be glycosylated, as is well understood by those in the art. For example, a useful linker sequence constituting a sialylation site is $X_1X_2NX_4X_5G$ (SEQ ID NO: 25), wherein $X_1$, $X_2$, $X_4$ and $X_5$ are each independently any amino acid residue.

In other embodiments, the 1 to 40 amino acids of the peptidyl linker moiety are selected from glycine, alanine, proline, asparagine, glutamine, and lysine. Preferably, a linker is made up of a majority of amino acids that are sterically unhindered, such as glycine and alanine. Thus, preferred linkers include polyglycines, polyserines, and polyalanines, or combinations of any of these. Some exemplary peptidyl linkers are poly$(Gly)_{1-8}$, particularly $(Gly)_3$, $(Gly)_4$ (SEQ ID NO:26), $(Gly)_5$ (SEQ ID NO:27) and $(Gly)_7$ (SEQ ID NO:28), as well as, GlySer and poly$(Gly)_4$Ser, such as "L15" (GGGGSGGGGSGGGGS; SEQ ID NO:29), poly $(Gly\text{-}Ala)_{2\text{-}4}$ and poly$(Ala)_{1\text{-}8}$. Other specific examples of peptidyl linkers include $(Gly)_5$Lys (SEQ ID NO:30), and $(Gly)_5$LysArg (SEQ ID NO:31). Other examples of useful peptidyl linkers are: Other examples of useful peptidyl linkers are:

```
                              (SEQ ID NO: 32)
(Gly)3Lys(Gly)4;

                              (SEQ ID NO: 33)
(Gly)3AsnGlySer(Gly)2;

                              (SEQ ID NO: 34)
(Gly)3Cys(Gly)4;
and

                              (SEQ ID NO: 35)
GlyProAsnGlyGly.
```

To explain the above nomenclature, for example, $(Gly)_3Lys(Gly)_4$ means Gly-Gly-Gly-Lys-Gly-Gly-Gly-Gly (SEQ ID NO:36). Other combinations of Gly and Ala are also useful.

Other preferred linkers are those identified herein as "L5" (GGGGS; or "G45"; SEQ ID NO:37), "L10" (GGGGSGGGGS; SEQ ID NO:38); "L20" (GGGGSGGGGSGGGGSGGGGS; SEQ ID NO:39); "L25" (GGGGSGGGGSGGGGSGGGGSGGGGS; SEQ ID NO:40) and any linkers used in the working examples hereinafter.

In some embodiments of the compositions of this invention, which comprise a peptide linker moiety, acidic residues, for example, glutamate or aspartate residues, are placed in the amino acid sequence of the linker moiety. Examples include the following peptide linker sequences:

```
                              (SEQ ID NO: 41)
GGEGGG;

                              (SEQ ID NO: 42)
GGEEEGGG;

                              (SEQ ID NO: 43)
GEEEG;

                              (SEQ ID NO: 44)
GEEE;

                              (SEQ ID NO: 45)
GGDGGG;

                              (SEQ ID NO: 46)
GGDDDGG;

                              (SEQ ID NO: 47)
GDDDG;

                              (SEQ ID NO: 48)
GDDD;

                              (SEQ ID NO: 49)
GGGGSDDSDEGSDGEDGGGGS;

                              (SEQ ID NO: 50)
WEWEW;

                              (SEQ ID NO: 51)
FEFEF;

                              (SEQ ID NO: 52)
EEEWWW;

                              (SEQ ID NO: 53)
EEEFFF;

                              (SEQ ID NO: 54)
WWEEEWW;
or

                              (SEQ ID NO: 55)
FFEEEFF.
```

In other embodiments, the linker constitutes a phosphorylation site, e.g., $X_1X_2YX_4X_5G$ (SEQ ID NO:56), wherein $X_1$, $X_2$, $X_4$, and $X_5$ are each independently any amino acid residue; $X_1X_2SX_4X_5G$ (SEQ ID NO:57), wherein $X_1$, $X_2$, $X_4$ and $X_5$ are each independently any amino acid residue; or $X_1X_2TX_4X_5G$ (SEQ ID NO:58), wherein $X_1$, $X_2$, $X_4$ and $X_5$ are each independently any amino acid residue.

The linkers shown here are exemplary; peptidyl linkers within the scope of this invention may be much longer and may include other residues. A peptidyl linker can contain, e.g., a cysteine, another thiol, or nucleophile for conjugation with a half-life extending moiety. In another embodiment, the linker contains a cysteine or homocysteine residue, or other 2-amino-ethanethiol or 3-amino-propanethiol moiety for conjugation to maleimide, iodoacetaamide or thioester, functionalized half-life extending moiety.

Another useful peptidyl linker is a large, flexible linker comprising a random Gly/Ser/Thr sequence, for example: GSGSATGGSGSTASSGSGSATH (SEQ ID NO:59) or HGSGSATGGSGSTASSGSGSAT (SEQ ID NO:60), that is estimated to be about the size of a 1 kDa PEG molecule. Alternatively, a useful peptidyl linker may be comprised of amino acid sequences known in the art to form rigid helical structures (e.g., Rigid linker: -AEAAAKEAAAKEAAAK-AGG-//SEQ ID NO:61). Additionally, a peptidyl linker can also comprise a non-peptidyl segment such as a 6 carbon aliphatic molecule of the formula —$CH_2$—$CH_2$—$CH_2$—$CH_2$—$CH_2$—$CH_2$—. The peptidyl linkers can be altered to form derivatives as described herein.

Non-peptidyl linkers. Optionally, a non-peptidyl linker moiety is also useful for conjugating the half-life extending moiety to the peptide portion of the half-life extending moiety-conjugated toxin peptide analog. For example, alkyl linkers such as —NH—$(CH_2)_s$—C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. Exemplary non-peptidyl linkers are PEG linkers (e.g., shown below):

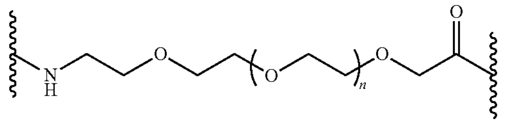

wherein n is such that the linker has a molecular weight of about 100 to about 5000 Daltons (Da), preferably about 100 to about 500 Da.

In one embodiment, the non-peptidyl linker is aryl. The linkers may be altered to form derivatives in the same manner as described herein. "Aryl" is phenyl or phenyl vicinally-fused with a saturated, partially-saturated, or unsaturated 3-, 4-, or 5 membered carbon bridge, the phenyl or bridge being substituted by 0, 1, 2 or 3 substituents selected from $C_{1-8}$ alkyl, $C_{1-4}$ haloalkyl or halo. "Heteroaryl" is an unsaturated 5, 6 or 7 membered monocyclic or partially-saturated or unsaturated 6-, 7-, 8-, 9-, 10- or 11 membered bicyclic ring, wherein at least one ring is unsaturated, the monocyclic and the bicyclic rings containing 1, 2, 3 or 4 atoms selected from N, O and S, wherein the ring is substituted by 0, 1, 2 or 3 substituents selected from $C_{1-8}$ alkyl, $C_{1-4}$ haloalkyl and halo.

Non-peptide portions of the inventive composition of matter, such as non-peptidyl linkers or non-peptide half-life extending moieties can be synthesized by conventional organic chemistry reactions.

Other embodiments of the multivalent linker comprise a rigid polyheterocyclic core of controlled length. The linkers are chemically differentiated on either end to accommodate orthogonal coupling chemistries (i.e. azide "Click", amide coupling, thioether formation by alkylation with maleimide or haloacetamide, oxime formation, reductive amination, etc.).

The above is merely illustrative and not an exhaustive treatment of the kinds of linkers that can optionally be employed in accordance with the present invention.

Example 1

Generation of Anti-GIPR/GLP-1 Peptide Conjugates

Anti-GIPR antibody 2G10_LC1.003 was engineered to have a E70C mutation in SEQ ID NO: 151 (light chain) or to have an E275C mutation in SEQ ID NO: 152 (heavy chain). Bis-cysteamine-capped anti-GIPR Cys mAb (3-12 mg/mL IgG1 in 20 mM sodium acetate, pH 5.0) was partially reduced using 2-4 equivalents of triphenylphosphine-3,3',3"-trisulfonate at RT. Cation Exchange Chromatography (CEX) was used to monitor the reaction progression (typically complete in 1-2 hours). The liberated cysteamine was purged from the partially over-reduced IgG1 by buffer exchange into 20 mM sodium acetate, pH 5.0. The resulting partially over-reduced and cysteamine-free Cys mAb (3-12 mg/mL) was reoxidized by addition of 4-7 equiv. of 4 mM dehydroascorbic acid, 0.5 M aq. $Na_2HPO_4$ to pH 7.0-7.5 followed by incubation at 2-8° C. The reoxidation progress was monitored by Reversed Phase HPLC. As soon as IgG1 was fully reformed (typically 1-3 hours) 2-3 equivalents of bromoacetyl-GLP-1 peptide (SEQ ID NO: 129) with C-terminal linker (SEQ ID NO: 29) was added and the reaction mixture was further incubated at 2-8° C. The alkylation reaction progress was monitored by LC/MS and/or CEX until the target Peptide-to-Antibody Ratio (PAR) profile is obtained (e.g. ≥95% PAR2, <5% PAR0+PAR1). The reaction mixture was quenched by adjusting the pH down to 5.0 using acetic acid. The desired PAR2 anti-GIPR/GLP-1 conjugate was purified using Hydrophobic Interaction Chromatography (HIC) followed by UF/DF formulation into 10% sodium acetate, 9% sucrose, pH 5.2.

TABLE 6

Amino acid SEQ ID NOs.

| Identifier | Construct | VL | VH | LC | HC | CDR L1 | CDR L2 | CDR L3 | CDR H1 | CDR H2 | CDR H3 |
|---|---|---|---|---|---|---|---|---|---|---|---|
| iPS: 361172 | 2G10_LC1.003 | 147 | 148 | 151 | 152 | 156 | 157 | 158 | 162 | 163 | 164 |

TABLE 7

Nucleic acid SEQ ID NOs.

| Identifier | Construct | VL | VH | LC | HC | CDR L1 | CDR L2 | CDR L3 | CDR H1 | CDR H2 | CDR H3 |
|---|---|---|---|---|---|---|---|---|---|---|---|
| iPS: 361172 | 2G10_LC1.003 | 145 | 146 | 149 | 150 | 153 | 154 | 155 | 159 | 160 | 161 |

TABLE 8

Variable Light and Variable Heavy Regions: Nucleic Acid ("NA") and Amino Acid ("AA") Sequences

| iPS# | Ab | Type | VL | VH |
|---|---|---|---|---|
| iPS:361172 | 2G10_LC1.003 | NA | GAAATAGTGATGACGCAGTCTCC<br>AGCCACCCTGTCTGTGTCTCCAG<br>GGGAAAGAGCCACCCTCTCCTGC<br>AGGGCCAGTCAGAGTGTTAGCAG<br>CAACTTAGCCTGGTACCAGCAGA<br>AACCTGGCCAGGCTCCCAGGCTC<br>CTCATCTATGGTGCAGCCACCAG<br>GGCCACTGGTATCCCAGCCAGGT<br>TCAGTGGCAGTGGGTCTGGGACA<br>GAGTTCACTCTCACCATCAGCAG<br>CCTGCAGTCTGAAGATTTTGCAG<br>TTTATTACTGTCAGCAGTATAATA<br>ACTGGCCTCTCACTTTCGGCGGA<br>GGGACCAAGGTGGAGATCAAAC<br>GA<br>SEQ ID NO: 145 | CAGGTGCAGCTGGTGGAGTCTGG<br>GGGAGGCGTGGTCCAGCCTGGGA<br>GGTCCCTGAGACTCTCCTGTGCA<br>GCATCTGGATTCACCTTCAGTAAC<br>TATGGCATGCACTGGGTCCGCCA<br>GGCTCCAGGCGAGGGGCTGGAGT<br>GGGTGGCAGCTATATGGTTTGAT<br>GCAAGTGATAAATACTATGCAGA<br>CGCCGTGAAGGGCCGATTCACCA<br>TCTCCAGAGACAACTCCAAGAAC<br>ACGCTGTATCTGCAAATGAACAG<br>CCTGAGAGCCGAGGACACGGCTG<br>TGTATTACTGTGCGAGAGATCAG<br>GCGATTTTTGGAGTGGTCCCCGA<br>CTACTGGGGCCAGGGAACCCTGG<br>TCACCGTCTCCTCA<br>SEQ ID NO: 146 |
| | | AA | EIVMTQSPATLSVSPGERATLSCRA<br>SQSVSSNLAWYQQKPGQAPRLLIY<br>GAATRATGIPARFSGSGSGTEFTLTI<br>SSLQSEDFAVYYCQQYNNWPLTFG<br>GGTKVEIKR<br>SEQ ID NO: 147 | QVQLVESGGGVVQPGRSLRLSCAA<br>SGFTFSNYGMHWVRQAPGEGLEW<br>VAAIWFDASDKYYADAVKGRFTIS<br>RDNSKNTLYLQMNSLRAEDTAVY<br>YCARDQAIFGVVPDYWGQGTLVT<br>VSS<br>SEQ ID NO: 148 |

TABLE 9A

CDRL1, CDRL2, and CDRL3 Nucleic Acid ("NA") and Amino Acid ("AA") Sequences

| iPS# | Ab | Type | CDRL1 | CDRL2 | CDRL3 |
|---|---|---|---|---|---|
| iPS:361172 | 2G10_LC1.003 | NA | AGGGCCAGTCAGAGT<br>GTTAGCAGCAACTTA<br>GCC<br>SEQ ID NO: 153 | GGTGCAGCCACCA<br>GGGCCACT<br>SEQ ID NO: 154 | CAGCAGTATAATAAC<br>TGGCCTCTCACT<br>SEQ ID NO: 155 |
| | | AA | RASQSVSSNLA<br>SEQ ID NO: 156 | GAATRAT<br>SEQ ID NO: 157 | QQYNNWPLT<br>SEQ ID NO: 158 |

TABLE 9B

CDRL1, CDRL2, and CDRL3 Nucleic Acid ("NA") and Amino Acid ("AA") Sequences

| iPS# | Ab | Type | CDRL1 | CDRL2 | CDRL3 |
|---|---|---|---|---|---|
| iPS:361172 | 2G10_LC1.003 | NA | AACTATGGCATGCAC<br>SEQ ID NO: 159 | GCTATATGGTTTG<br>ATGCAAGTGATAA<br>ATACTATGCAGAC<br>GCCGTGAAGGGC<br>SEQ ID NO: 160 | GATCAGGCGATTTTT<br>GGAGTGGTCCCCGAC<br>TAC<br>SEQ ID NO: 161 |
| | | AA | NYGMH<br>SEQ ID NO: 162 | AIWFDASDKYYAD<br>AVKG<br>SEQ ID NO: 163 | DQAIFGVVPDY<br>SEQ ID NO: 164 |

TABLE 10

Light and Heavy Chain Nucleic Acid ("NA") and Amino Acid ("AA") Sequences

| iPS# | Ab | Type | LC | HC |
|---|---|---|---|---|
| iPS:361172 | 2G10_LC1.003 | NA | GAAATAGTGATGACGCAGTCTC<br>CAGCCACCCTGTCTGTGTCTCC<br>AGGGGAAAGAGCCACCCTCTCC | CAGGTGCAGCTGGTGGAGTCTGGG<br>GGAGGCGTGGTCCAGCCTGGGAG<br>GTCCCTGAGACTCTCCTGTGCAGC |

TABLE 10-continued

Light and Heavy Chain Nucleic Acid ("NA") and Amino Acid ("AA") Sequences

| iPS# | Ab | Type | LC | HC |
|---|---|---|---|---|
| | | | TGCAGGGCCAGTCAGAGTGTTA GCAGCAACTTAGCCTGGTACCA GCAGAAACCTGGCCAGGCTCCC AGGCTCCTCATCTATGGTGCAG CCACCAGGGCCACTGGTATCCC AGCCAGGTTCAGTGGCAGTGGG TCTGGGACAGAGTTCACTCTCA CCATCAGCAGCCTGCAGTCTGA AGATTTTGCAGTTTATTACTGTC AGCAGTATAATAACTGGCCTCT CACTTTCGGCGGAGGGACCAAG GTGGAGATCAAACGAACGGTG GCTGCACCATCTGTCTTCATCTT CCCGCCATCTGATGAGCAGTTG AAATCTGGAACTGCCTCTGTTG TGTGCCTGCTGAATAACTTCTAT CCCAGAGAGGCCAAAGTACAGT GGAAGGTGGATAACGCCCTCCA ATCGGGTAACTCCCAGGAGAGT GTCACAGAGCAGGACAGCAAG GACAGCACCTACAGCCTCAGCA GCACCCTGACGCTGAGCAAAGC AGACTACGAGAAACACAAAGT CTACGCCTGCGAAGTCACCCAT CAGGGCCTGAGCTCGCCCGTCA CAAAGAGCTTCAACAGGGGAG AGTGT SEQ ID NO: 149 | ATCTGGATTCACCTTCAGTAACTA TGGCATGCACTGGGTCCGCCAGGC TCCAGGCGAGGGGCTGGAGTGGG TGGCAGCTATATGGTTTGATGCAA GTGATAAATACTATGCAGACGCCG TGAAGGGCCGATTCACCATCTCCA GAGACAACTCCAAGAACACGCTG TATCTGCAAATGAACAGCCTGAGA GCCGAGGACACGGCTGTGTATTAC TGTGCGAGAGATCAGGCGATTTTT GGAGTGGTCCCCGACTACTGGGGC CAGGGAACCCTGGTCACCGTCTCC TCAGCCTCCACCAAGGGCCCATCG GTCTTCCCCCTGGCACCCTCCTCC AAGAGCACCTCTGGGGGCACAGC GGCCCTGGGCTGCCTGGTCAAGGA CTACTTCCCCGAACCGGTGACGGT GTCGTGGAACTCAGGCGCCCTGAC CAGCGGCGTGCACACCTTCCCGGC TGTCCTACAGTCCTCAGGACTCTA CTCCCTCAGCAGCGTGGTGACCGT GCCCTCCAGCAGCTTGGGCACCCA GACCTACATCTGCAACGTGAATCA CAAGCCCAGCAACACCAAGGTGG ACAAGAAAGTTGAGCCCAAATCTT GTGACAAAACTCACACATGCCCAC CGTGCCCAGCACCTGAACTCCTGG GGGGACCGTCAGTCTTCCTCTTCC CCCCAAAACCCAAGGACACCCTCA TGATCTCCCGGACCCCTGAGGTCA CATGCGTGGTGGTGGACGTGAGCC ACGAAGACCCTGAGGTCAAGTTCA ACTGGTACGTGGACGGCGTGGAG GTGCATAATGCCAAGACAAAGCC GTGTGAGGAGCAGTACGGCAGCA CGTACCGTTGTGTCAGCGTCCTCA CCGTCCTGCACCAGGACTGGCTGA ATGGCAAGGAGTACAAGTGCAAG GTCTCCAACAAAGCCCTCCCAGCC CCCATCGAGAAAACCATCTCCAAA GCCAAAGGGCAGCCCCGAGAACC ACAGGTGTACACCCTGCCCCCATC CCGGGAGGAGATGACCAAGAACC AGGTCAGCCTGACCTGCCTGGTCA AAGGCTTCTATCCCAGCGACATCG CCGTGGAGTGGGAGAGCAATGGG CAGCCGGAGAACAACTACAAGAC CACGCCTCCCGTGCTGGACTCCGA CGGCTCCTTCTTCCTCTATAGCAA GCTCACCGTGGACAAGAGCAGGT GGCAGCAGGGGAACGTCTTCTCAT GCTCCGTGATGCATGAGGCTCTGC ACAACCACTACACGCAGAAGAGC CTCTCCCTGTCTCCGGGTAAA SEQ ID NO: 150 |
| | | AA | EIVMTQSPATLSVSPGERATLSCR ASQSVSSNLAWYQQKPGQAPRL LIYGAATRATGIPARFSGSGSGTE FTLTISSLQSEDFAVYYCQQYNN WPLTFGGGTKVEIKRTVAAPSVFI FPPSDEQLKSGTASVVCLLNNFY PREAKVQWKVDNALQSGNSQES VTEQDSKDSTYSLSSTLTLSKAD YEKHKVYACEVTHQGLSSPVTKS FINRGEC SEQ ID NO: 151 | QVQLVESGGGVVQPGRSLRLSCAA SGFTFSNYGMHWVRQAPGEGLEW VAAIWFDASDKYYADAVKGRFTIS RDNSKNTLYLQMNSLRAEDTAVYY CARDQAIFGVVPDYWGQGTLVTVS SASTKGPSVFPLAPSSKSTSGGTAAL GCLVKDYFPEPVTVSWNSGALTSG VHTFPAVLQSSGLYSLSSVVTVPSSS LGTQTYICNVNHKPSNTKVDKKVEP KSCDKTHTCPPCPAPELLGGPSVFLF PPKPKDTLMISRTPEVTCVVVDVSH EDPEVKFNWYVDGVEVHNAKTKPC EEQYGSTYRCVSVLTVLHQDWLNG KEYKCKVSNKALPAPIEKTISKAKG QPREPQVYTLPPSREEMTKNQVSLT CLVKGFYPSDIAVEWESNGQPENNY KTTPPVLDSDGSFFLYSKLTVDKSR WQQGNVFSCSVMHEALHNHYTQK SLSLSPGK SEQ ID NO: 152 |

A "GLP-1 receptor agonist" or "GLP-1 peptide" refers to compounds having GLP-1 receptor activity. Such exemplary compounds include exendins, exendin analogs, exendin agonists, GLP-1(7-37), GLP-1(7-37) analogs, GLP-1(7-37) agonists, and the like. The GLP-1 receptor agonist compounds may optionally be amidated. The terms "GLP-1 receptor agonist" and "GLP-1 receptor agonist compound" have the same meaning.

TABLE 1

Examples of GLP-1 receptor agonist Sequences

| SEQ ID NO: | Sequence |
|---|---|
| 62 | HGEGTFTSDLSKQMEEEAVRLFIEWLKNGGPSSGAPPPS |
| 63 | HSDGTFTSDLSKQMEEEAVRLFIEWLKNGGPSSGAPPPS |
| 64 | HGEGTFTSDLSKQLEEEAVRLFIEWLKNGGPSSGAPPPS |
| 65 | HGEGTFTSDLSKQLEEEAVRLFIEFLKNGGPSSGAPPPS |
| 66 | HGEGTFTSDLSKQLEEEAARLFIEFLKNGGPSSGAPPPS |
| 67 | HGEGTFTSDLSKQMEEEAVRLFIEWLKNGG |
| 68 | HGEGTFTSDLSKQLEEEAVRLFIEWLKNGG |
| 69 | HGEGTFTSDLSKQLEEEAVRLFIEFLKNGG |
| 70 | HGEGTFTSDLSKQLEEEAARLFIEFLKNGG |
| 71 | HGEGTFTSDLSKQMEEEAVRLFIEWLKN |
| 72 | HGEGTFTSDLSKQLEEEAVRLFIEWLKN |
| 73 | HGEGTFTSDLSKQLEEEAVRLFIEFLKN |
| 74 | HGEGTFTSDLSKQLEEEAARLFIEFLKN |
| 75 | HGEGTFTSDLSKQLEEKAAKEFIEFLKQGGPSSGAPPPS |
| 76 | HGEGTFTSDLSKQLEEKAAKEFIEWLKQGGPSSGAPPPS |
| 77 | HGEGTFTSDLSKQ(octylG)EEEAVRLFIEWLKQGGPSSGAPPPS |
| 78 | HGEGTFTSDLSKQLEEEAVRLFIEWLKQGGPSS(octylG)APPPS |
| 79 | HGEFTFTSDLSKQLEEEAVRLFIEWLKQGGPSKEIIS |
| 80 | HGEFTFTSDLSKQLEEKAAKEFIEWLKQGGPSSGAPPPS |
| 81 | HGEGTFTSDLVKILEAEAVRKFIEFLKNGGPSSGAPPPS |
| 82 | HGEGTFTSDLSKQMEEEAVRLFIEWLKNGGPSSGAPPPSK |
| 83 | HAEGTFTSDVSSYLEGQAAKEFIAWLVKGRG |
| 84 | HAEGTFTSDVSSYLEGQAAKEFIAWLVKGR |
| 85 | H(Aib)EGTFTSDVSSYLEGQAAREFIAFLVR(Aib)R |
| 86 | $HXaa_8EGTFTSDVSSYLEXaa_{22}Xaa_{23}AAKEFI$<br>$Xaa_{30}WLXaa_{33}Xaa_{34}GXaa_{36}Xaa_{37}$<br>wherein $Xaa_8$ is A, V, or G<br>$Xaa_{22}$ is G, K, or E<br>$Xaa_{23}$ is Q or K<br>$Xaa_{30}$ is A or E<br>$Xaa_{33}$ is V or K<br>$Xaa_{34}$ is K, N, or R<br>$Xaa_{36}$ is R or G<br>and $Xaa_{37}$ is G, H, P, or absent |
| 87 | HAEGTFTSDVSSYLEGQAAKEFIAWLVRGRG |
| 88 | HAEGTFTSDVSSYLEGQAAKEFIEWLVKGRG |
| 89 | HAEGTFTSDVSSYLEKQAAKEFIAWLVKGRG |
| 90 | HGEGTFTSDVSSYLEEQAAKEFIAWLVKGGG |
| 91 | HVEGTFTSDVSSYLEEQAAKEFIAWLVKGGG |
| 92 | HGEGTFTSDVSSYLEEQAAKEFIAWLKNGGG |

TABLE 1-continued

| Examples of GLP-1 receptor agonist Sequences | |
|---|---|
| SEQ ID NO: | Sequence |
| 93 | HVEGTFTSDVSSYLEEQAAKEFIAWLKNGGG |
| 94 | HGEGTFTSDVSSYLEEQAAKEFIAWLVKGGP |
| 95 | HVEGTFTSDVSSYLEEQAAKEFIAWLVKGGP |
| 96 | HGEGTFTSDVSSYLEEQAAKEFIAWLKNGGP |
| 97 | HVEGTFTSDVSSYLEEQAAKEFIAWLKNGGP |
| 98 | HGEGTFTSDVSSYLEEQAAKEFIAWLVKGG |
| 99 | HVEGTFTSDVSSYLEEQAAKEFIAWLVKGG |
| 100 | HVEGTFTSDVSSYLEEQAAKEFIAWLVNGG |
| 101 | HGEGTFTSDVSSYLEEQAAKEFIAWLVNGG |
| 102 | HXaa$_8$EGTFTSDVS<br>SYLEXaa$_{22}$QAAKEFIAWLXaa$_{33}$KGGPSSGAPPPC$_{45}$C$_{46}$-Z, wherein<br>Xaa$_8$ is: D-Ala, G, V, L, I, S or T<br>Xaa$_{22}$ is G, E, D or K<br>Xaa$_{33}$ is: V or I<br>and Z is OH or NH$_2$ and, optionally, wherein (i) one polyethylene glycol moiety is covalently attached to C$_{45}$, (ii) one polyethylene glycol moiety is covalently attached to C$_{46}$, or (iii) one polyethylene glycol moiety is attached to C$_{45}$ and one polyethylene glycol moiety is attached to C$_{46}$. |
| 103 | HVEGTFTSDVSSYLEEQAKEFIAWLIKGGPSSGAPPPC$_{45}$C$_{46}$-NH$_2$ and, optionally, wherein (i) one polyethylene glycol moiety is covalently attached to C$_4$, (ii) one polyethylene glycol moiety is covalently attached to C$_{46}$, or (iii) one polyethylene glycol moiety is attached to C$_{45}$ and one polyethylene glycol moiety is attached to C$_{46}$ |
| 104 | HGEGTFTSDLSKQMEEEAVKLFIEWLKNGGPSSGAPPPS |
| 105 | HGEGTFTSDLSKQMEEEAVRLFIEWLKNGGPKSGAPPPS |
| 106 | GEGTFTSDLSKQMEEEAVKLFIEWLKNGGPSSGAPPPS |
| 107 | HGEGTFTSDLSRQNorLeEEEAVRLFIEWLRNGGPKSGAPPPS |
| 108 | HGEGTFTSDLSKQMEEEAVKLFIEWLKNGGPSSGAPPPS |
| 109 | HGEGTFTSDLSKQMEEEAVKLFIEWLKNGGPSSGAPPPS |
| 110 | HGEGTFTSDLSKQMEEEAVKLFIEWLKNGGPSSGAPPPS |
| 111 | HGEGTFTSDLSKQMEEEAVKLFIEWLKNGGPSSGAPPPS |
| 112 | HGEGTFTSDLSKQMEEEAVRLFIEWLKNGGPSSGAPPPSK |
| 113 | HGEGTFTSDLSKQMEEEAVRLFIEWLKNGGPSSGAPPPSK |
| 114 | HGEGTFTSDLSKQMEEEAVRLFIEWLKNGGPSSGAPPPSK |
| 115 | HGEGTFTSDLSKQMEEEAVRLFIEWLKNGGPSSGAPPPSK |
| 116 | HGEGTFTSDLSKQMEEEAVRLFIEWLKNGGPSSGAPPPSK |
| 117 | HGEGTFTSDLSKQMEEEAVRLFIEWLKNGGPSSGAPPPSK |
| 118 | AEGTFTSDVSSYLEGQAAREFIAWLVKGRG |
| 119 | AEGTFTSDVSSYLEGQAAREFIAWLVKGRG |
| 120 | HAEGTFTSDVSSYLEGQAAREFIAWLVRGRGK |

TABLE 1-continued

| Examples of GLP-1 receptor agonist Sequences | |
|---|---|
| SEQ ID NO: | Sequence |
| 121 | HAEGTFTSDVSSYLEGQAAREFIAWLVRGRGK |
| 122 | {H2}H[Aib]EGTFTSDVSSYLE[Aib]QAAKEFIAWLKNGG[Aeea] [Aeea]K{CONH2} |
| 123 | {H2}H[Aib]EGTFTSDVSSYLE[Aib]QAAKEFIAWLVKGGG |
| 124 | {H2}H[Aib]EGTFTSDVSSYLEGEAAKKFIAWLVKGGG |
| 125 | {H2}H[Aib]EGTFTSDVSSYLEEQAAKEFIAWLVKGGK{CONH2} |
| 126 | {H2}H[Aib]EGTFTSDVSSYLE[Aib]EAVRLFIEWLKNGGPSSGAPPPS |
| 127 | {H2}HGEGTFTSDVSSYLEEQAAKEFIAWLVKGGG |
| 128 | {H2}H[Aib]EGTFTSDVSSYLEEQAAKEFIAWLVKGGG |
| 129 | {H2}H[Aib]EGTFTSDYSSYLEEQAAKEFIAWLVKGGG |
| 130 | {H2}H[Aib]EGTFTSDVSKYLEEEAVRLFIEWLKNGGG |
| 131 | {H2}H[Aib]EGTFTSDVSKYLEEEAAKLFIEWLKNGGG |
| 132 | {H2}H[Aib]EGTFTSDVSKYLEEEAAKLFIEWLVKGGG |
| 133 | {H2}H[Aib]IGTFTSDVSSYLE[Aib]QAAKEFIAWLVKGG |
| 134 | {H2}H[Aib]EGTFTSEVSSYLE[Aib]QAAKEFIAWLVKGG |
| 135 | {H2}H[Aib]AGTFTSDVSSYLE[Aib]QAAKEFIAWLVKGG |
| 136 | {H2}H[Aib]EGTFTSDVSSYLE[Aib]QAAKEFAAWLVKGG |
| 137 | {H2}H[Aib]EGTFTSDVSSYLE[Aib]QAAKEFIAALVKGG |
| 138 | {H2}H[Aib]TGTFTSDVSSYLE[Aib]QAAKEFIAWLVKGGG |
| 139 | {H2}H[Aib]EGTFTSEVSSYLE[Aib]QAAKEFIAALVKGGG |
| 140 | {H2}H[Aib]EGTFTSDVSSYLE[Aib]QAAKEFIAALVKGGG |
| 141 | {H2}H[Aib]EGTFTSDVSSYLEEEAVRLFIEWLKNGGPSSGAPPPS |
| 142 | {H2}H[Aib]EGTFTSDYSSYLE[Aib]QAAKEFIAWLVKGGG |
| 143 | {H2}H[Aib]EGTFTSDVSSYLE[Aib]QAAKEFIAWLVKGGG{CONH2} |
| 144 | {Dmia}SQGTFTSDYSKYLDERRAKDFVQWLMNT |
| 165 | {H2}HGEGTFTSDLSKQMEEEAVRLFIEWLKNGGPSSGAPPPS |

AEEA refers to [2-(2-amino)ethoxy)]acetic acid
EDA refers to ethylenediamine
MPA refers to maleimidopropionic acid.

Results and Discussion

Figure 2:
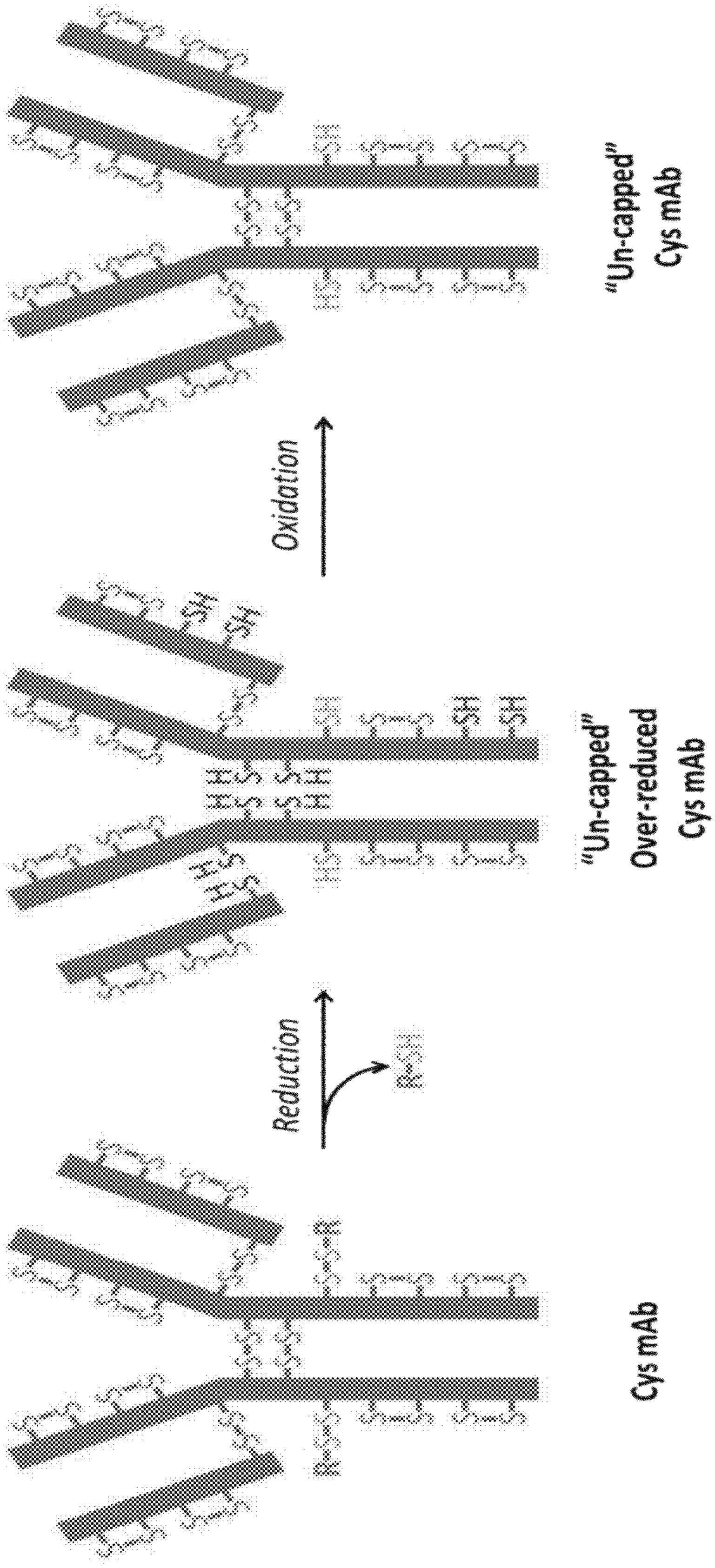
FIG. 2. Net Selective Reduction can be carried-out in two steps. (1) Reduction step ensures complete "un-capping" of the engineered disulfides—some native disulfide bonds are also cleaved. (2) Oxidation step restores the native structure of IgG1. UF/DF clearance of the thiol liberated in the Reduction step (R—SH) is required prior to the oxidation to prevent "re-capping".

A successful site-specific conjugation with Cys mAb protein (IgG1) is critically reliant on the ability to selectively reduce ("un-cap") the cysteine residues that were engineered into the disulfide-bridged IgG1 scaffold. This practically challenging process aims to reduce only the disulfide bonds of the two engineered cysteines in the presence of at least sixteen native disulfide bonds holding together the IgG1 tetramer. A single step Selective Reduction would be highly desirable, but is currently not feasible (FIG. 1). A two-step Net Selective Reduction was developed instead (FIG. 2):

Reduction Step: Cys mAb allowed to react with a reducing agent (typically a phosphine) to effect complete reduction ("un-capping") of the engineered cysteine residues. Some native disulfide bonds are also reduced. The degree of this undesirable side-reaction is highly dependent on the reaction parameters including post-translational modifications (e.g. identity of "caps") and reaction conditions (e.g. temperature, type and amount a reducing agent, reaction buffer). The result is "un-capped" and over-reduced Cys mAb.

Oxidation Step: The thiol "caps" liberated in the Reduction Step must be cleared before proceeding to prevent the undesirable "re-capping" of the Cys mAb. The native disulfide bonds are then restored in the presence of an oxidant (typically dehydroascorbic acid).

Figure 3:
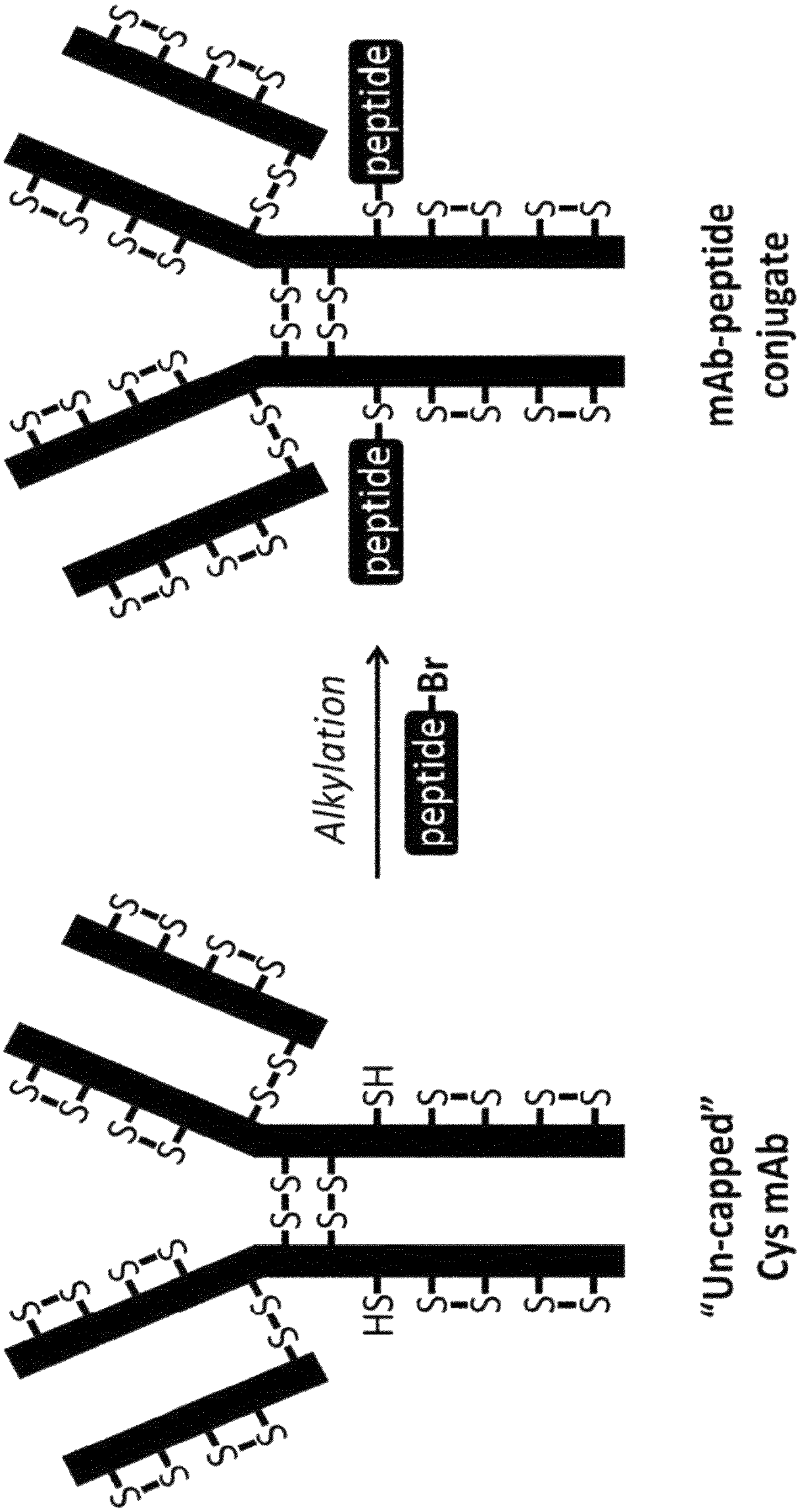
FIG. 3. "Un-capped" Cys mAb readily undergoes site-selective conjugation with alkylating agents (e.g. peptide bromoacetamide derivatives).

This two-step protocol generates "Un-capped" Cys mAb protein ready for the site-specific conjugation via S-alkylation reaction (FIG. 3).

Figure 4:
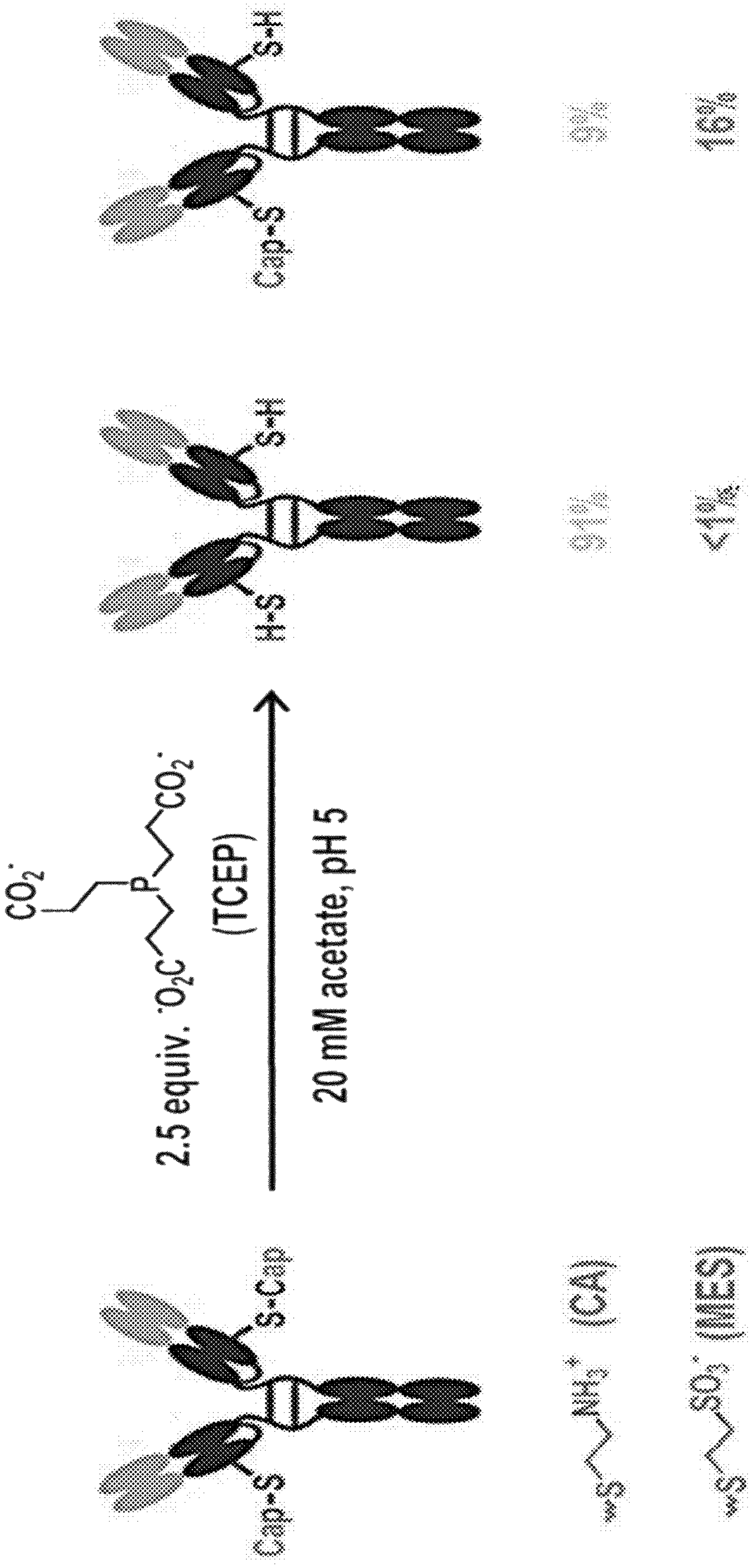
FIG. 4. Head-to-head comparison of the reduction performance of a matched pair (CA+TCEP) and mismatched pair (MES+TCEP).
Figure 5:
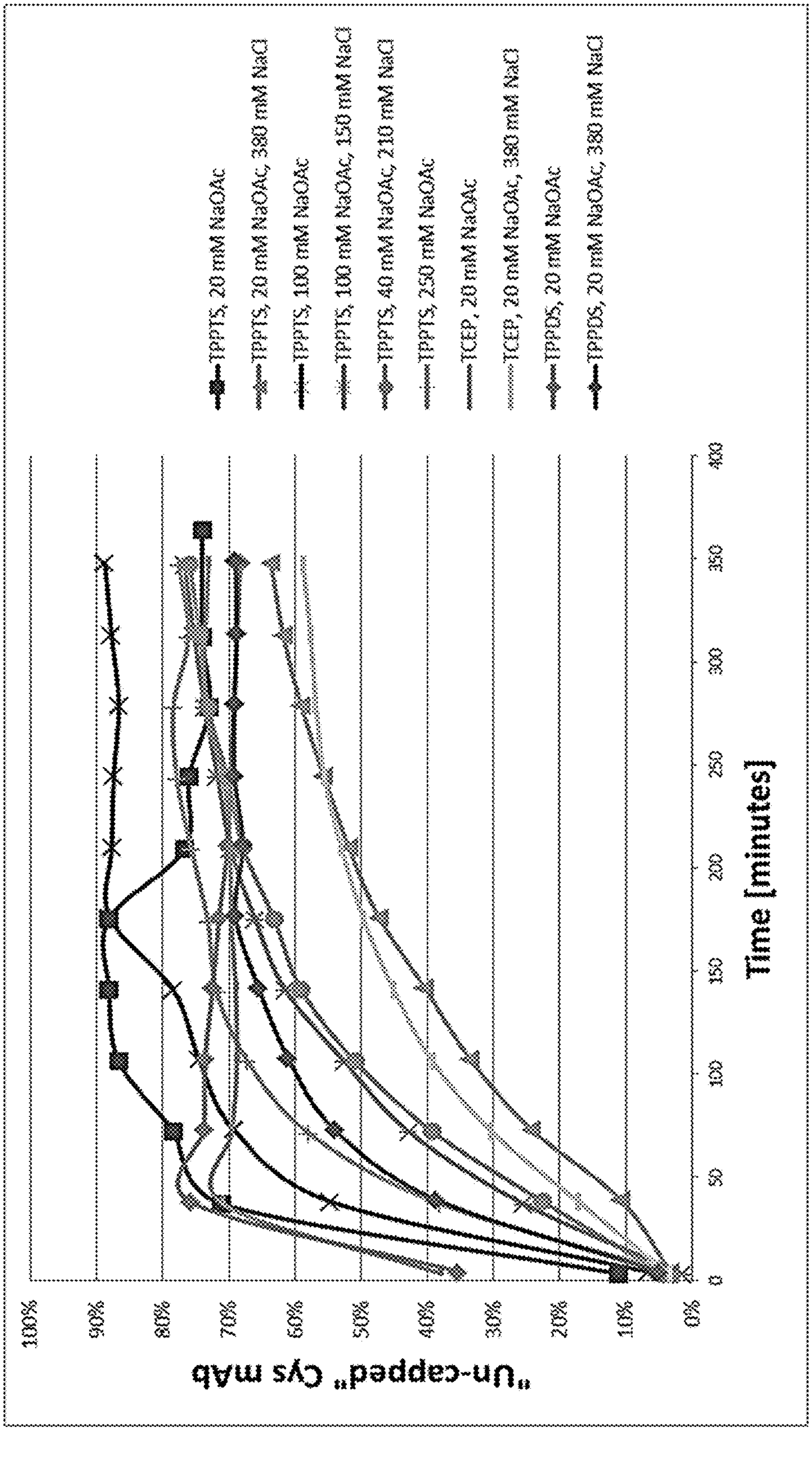
FIG. 5. Formation of "Un-capped" Cys mAb over time. Reaction Conditions: 10 g/L of Cysteamine-capped Cys mAb in the specified buffer at pH 5.0, 3.5 equiv. of phosphine (TPPTS, TPPDS, or TCEP), RT. Reaction mixture monitored by Cation Exchange Chromatography and quantified at 280 nm. Only "Un-capped" Cys mAb plotted in this figure.
Figure 6:
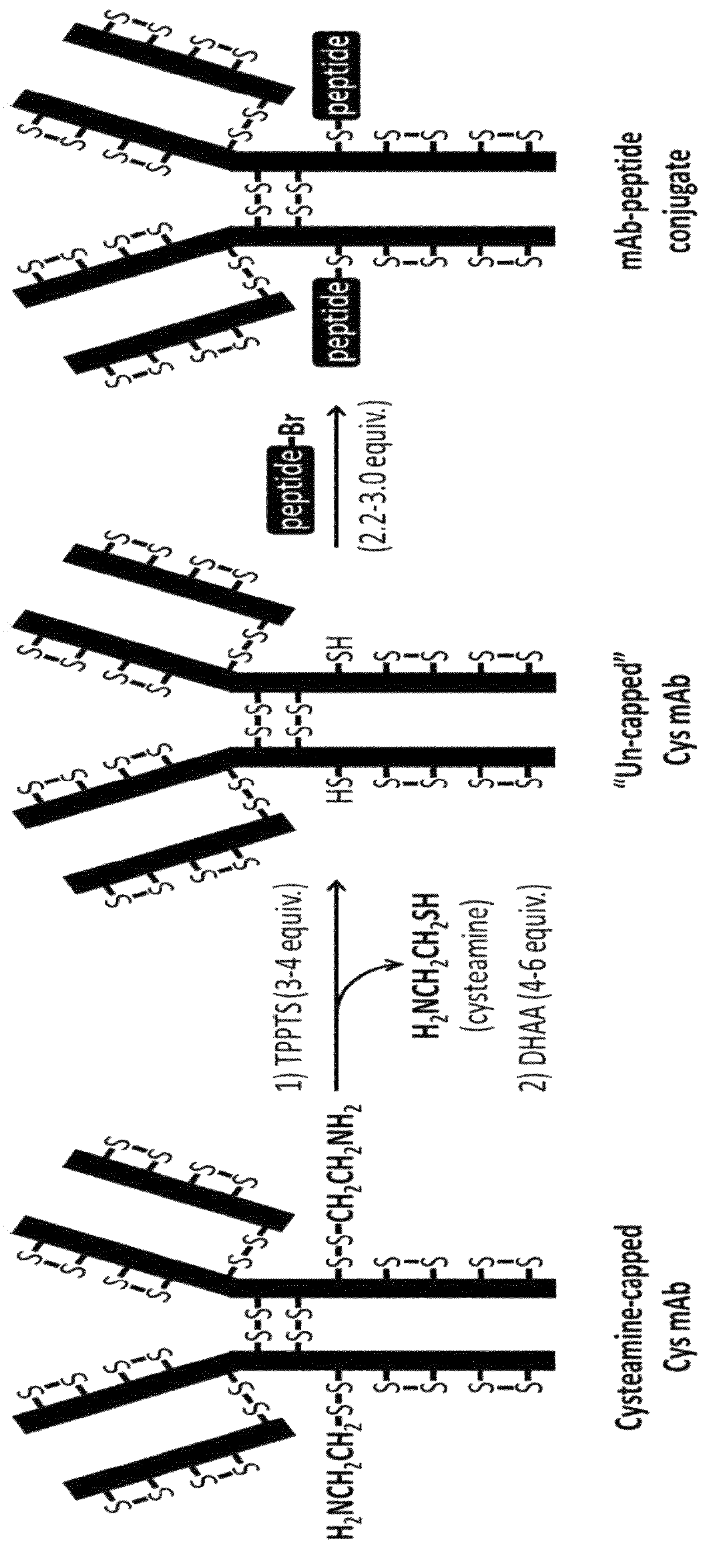
FIG. 6. Cysteamine-based conjugation process allows nearly stoichiometric amounts of reagents for the reduction, oxidation, and alkylation to afford mAb-peptide conjugate with uniform PAR2 content (e.g. ≥95%).

In order to achieve virtually homogenous Cys mAb conjugate (PAR2; Peptide-to-Antibody Ratio of 2) it is imperative to keep the over-reduction to minimum since restoration of the native disulfide bonds via oxidation is not perfect. On the other hand under-reduction is equally undesirable as it leads to under-alkylated impurities (PAR1, PAR0). The optimal reduction profile consisting of complete un-capping with minimal over-reduction requires proper combination of several parameters:

- Positively charged cysteine "cap" (e.g. cysteamine, CA) must be paired with negatively charged reducing agent. Triphenylphosphine-3,3',3"-trisulfonate (TPPTS) was found to be particularly effective. Other anionic phosphines e.g. TCEP, TPPDS were functional, but their performance was inferior to TPPTS (Fig.). Mismatched pairs e.g. mercaptoethanesulfonate (MES, negatively charged "cap") and tris(2-carboxyethyl)phosphine (TCEP, negatively charged reducing agent) led to sluggish, non-selective and/or incomplete reactions (FIG. 4).
- Reaction buffers must be of low ionic strength (e.g. 20 mM sodium acetate) to maximize the attractive Coulombic interactions between oppositely charged reaction partners (e.g. positively charged cysteamine-capped IgG1 and negatively TPPTS). Increasing ionic strength of the reaction medium make the reduction sluggish and non-selective (Fig.).
- Reaction pH must be sufficiently low (e.g. pH 5) to keep the liberated thiols ("caps") from undergoing secondary side-reactions e.g. disulfide exchange with the native disulfides of IgG1.
- Proper combination of the above variables allows for complete un-capping using only a small excess of the reducing agent (e.g. 1.5 equiv. excess, 3.5 equiv. per Cys mAb total) consequently leading to minimal over-reduction. Such minimal degree of over-reduction is readily corrected in the following Oxidation Step using dehydroascorbic acid (DHAA, e.g. 4-6 equiv.) as a mild oxidant. The resulting virtually homogenous "un-capped" Cys-mAb can be cleanly alkylated using only a small excess (e.g. 0.2 equiv. excess, 2.2 equiv. per Cys mAb total) of bromoacetamides (e.g. bromoacetamide derivatives of synthetic peptides) to afford ≥95% of PAR2 conjugate (Fig.).

What is claimed is:

1. A method for preparing an antibody conjugate, the method comprising the steps of:

a) exposing an intact antibody to cysteamine, wherein the cysteamine forms a mixed-disulfide bond with at least one cysteine residue of a heavy chain of the intact antibody, wherein the at least one cysteine residue is at the amino acid position relative to position E276 of SEQ ID NO: 8;

b) contacting the intact antibody, after step a), with trisodium triphenylphosphine-3, 3',3"-trisulfonate ("TPPTS") to reduce the mixed-disulfide bond to form a reduced intact antibody;

c) contacting the reduced intact antibody with an oxidizing agent to form an oxidized intact antibody; and d) contacting the oxidized intact antibody with an activated chemical moiety to form the antibody conjugate.

2. The method according to claim 1, wherein following step a) and before step b), cation exchange chromatography is performed to remove excess cysteamine.

3. The method according to claim 1, wherein the intact antibody is contacted with TPPTS in step b) at of TPPTS to antibody ratio of 2:1 to 4:1 (mole/mole).

4. The method according to claim 1, wherein following step b) and before step c), a buffer exchange step is performed to remove the TPPTS.

5. The method according to claim 4, wherein the buffer exchange step is ultrafiltration and/or diafiltration.

6. The method according to claim 1, wherein the oxidizing agent is dehydroascorbic acid ("DHAA").

7. The method according to claim 6, wherein the reduced intact antibody is contacted with DHAA in step c) at a DHAA to antibody ratio of 3:1 to 6:1 (mole/mole).

8. The method according to claim 1, wherein the activated chemical moiety is a peptide comprising a halogen, wherein the halogen is selected from the group consisting of Br, I, and Cl.

9. The method according to claim 8, wherein the oxidized antibody is contacted with the activated chemical moiety in step d) at an activated chemical moiety to antibody ratio of 2:1 to 3:1 (mole/mole).

10. The method according to claim 1, wherein following step d), a purification step is performed to remove the activated chemical moiety.

11. The method according to claim 10, wherein the purification step includes hydrophobic interaction chromatography ("HIC"), ultrafiltration and/or diafiltration, or hydrophobic interaction chromatography ("HIC") followed by ultrafiltration and/or diafiltration.

12. The method according to claim 1, wherein the TPPTS of step b) is in a buffer comprising about 20 to about 100 mM NaOAc.

13. The method according to claim 12, wherein the buffer does not contain NaCl.

14. The method according to claim 12, wherein the buffer has a pH of about pH 5.0.

15. The method according to claim 13, wherein the buffer has a pH of about pH 5.0.

16. The method of claim 1, wherein the intact antibody is an anti-GIPR antibody.

17. The method of claim 1, wherein the activated chemical moiety is a bromoacetylated GLP-1 receptor agonist.

18. A method for preparing an antibody-GLP-1 receptor agonist conjugate, the method comprising the steps of:

a) exposing an intact antibody to cysteamine, wherein the cysteamine forms a mixed-disulfide bond with at least one cysteine residue of a heavy chain of the intact antibody, wherein the at least one cysteine residue is at the amino acid position relative to position E276 of SEQ ID NO: 8;

b) contacting the intact antibody, after step a), with trisodium triphenylphosphine-3, 3',3"-trisulfonate ("TPPTS") to reduce the mixed-disulfide bond to form a reduced intact antibody;

c) contacting the reduced intact antibody with an oxidizing agent to form an oxidized intact antibody; and d) contacting the oxidized intact antibody with a bromoacetylated GLP-1 receptor agonist to form the antibody-GLP-1 receptor agonist conjugate.

19. A method for preparing an anti-GIPR antibody conjugate, the method comprising the steps of:

a) exposing an intact anti-GIPR antibody to cysteamine, wherein the cysteamine forms a mixed-disulfide bond with at least one cysteine residue of a heavy chain of the intact anti-GIPR antibody;

b) contacting the intact anti-GIPR antibody, after step a), with trisodium triphenylphosphine-3, 3',3''-trisulfonate ("TPPTS") to reduce the mixed-disulfide bond to form a reduced intact anti-GIPR antibody;

c) contacting the reduced intact anti-GIPR antibody with an oxidizing agent to form an oxidized intact anti-GIPR antibody; and d) contacting the oxidized intact anti-GIPR antibody with an activated chemical moiety to form the anti-GIPR antibody conjugate.

20. The method of claim 19, wherein the at least one cysteine residue of the heavy chain is at the amino acid position relative to E275 of SEQ ID NO: 152.

21. A method for preparing an anti-GIPR antibody-GLP-1 receptor agonist conjugate, the method comprising the steps of;

a) exposing an intact anti-GIPR antibody to cysteamine, wherein the cysteamine forms a mixed-disulfide bond with at least one cysteine residue of a heavy chain of the intact anti-GIPR antibody;

b) contacting the intact anti-GIPR antibody, after step a), with trisodium triphenylphosphine-3, 3',3"-trisulfonate ("TPPTS") to reduce the mixed-disulfide bond to form a reduced intact anti-GIPR antibody;

c) contacting the reduced intact anti-GIPR antibody with an oxidizing agent to form an oxidized intact anti-GIPR antibody; and d) contacting the oxidized intact anti-GIPR antibody with a bromoacetylated GLP-1 receptor agonist to form the anti-GIPR antibody-GLP-1 receptor agonist conjugate.

22. The method of claim 21, wherein the at least one cysteine residue of the heavy chain is at the amino acid position relative to position E275 of SEQ ID NO: 152.

23. A method for preparing an anti-GIPR antibody-GLP-1 receptor agonist conjugate, the method comprising the steps of:

a) obtaining an anti-GIPR antibody comprising two light chains and two heavy chains, wherein each light chain comprises a complementarity determining region 1 (LCDR1), a LCDR2, and LCDR3 of SEQ ID NOs: 156-158, respectively, and each heavy chain comprises a complementary determining region 1 (HCDR1), a HCDR2, and a HCDR3 of SEQ ID NOs: 162-164, respectively;

b) exposing the anti-GIPR antibody to cysteamine, wherein the cysteamine forms a mixed-disulfide bond with a cysteine residue in each heavy chain of the anti-GIPR antibody;

c) contacting the anti-GIPR antibody, after step b), with trisodium triphenylphosphine-3, 3',3'''-trisulfonate to reduce the mixed-disulfide bond to form a reduced anti-GIPR antibody;

d) contacting the reduced anti-GIPR antibody with an oxidizing agent to form an oxidized anti-GIPR antibody; and e) contacting the oxidized anti-GIPR antibody with a bromoacetylated GLP-1 receptor agonist of SEQ ID NO: 129 C-terminally linked to a peptide linker of SEQ ID NO: 29, to form the anti-GIPR antibody-GLP-1 receptor agonist conjugate.

24. The method of claim 23, wherein the cysteine residue in each heavy chain is at the amino acid position relative to position E275 of SEQ ID NO: 152.

* * * * *